(12) United States Patent
Koya et al.

(10) Patent No.: US 6,800,660 B2
(45) Date of Patent: Oct. 5, 2004

(54) TAXOL ENHANCER COMPOUNDS

(75) Inventors: Keizo Koya, Brookline, MA (US); Lijun Sun, Harvard, MA (US); Shoujun Chen, Billerica, MA (US); Noriaki Tatsuta, Lexington, MA (US); Yaming Wu, Lexington, MA (US); Mitsunori Ono, Lexington, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 66 days.

(21) Appl. No.: 10/193,075

(22) Filed: Jul. 10, 2002

(65) Prior Publication Data

US 2003/0119914 A1 Jun. 26, 2003

Related U.S. Application Data

(60) Provisional application No. 60/304,252, filed on Jul. 10, 2001, and provisional application No. 60/361,946, filed on Mar. 6, 2002.

(51) Int. Cl.$^7$ .................... A61K 31/16; C07C 241/00
(52) U.S. Cl. .................. 514/614; 514/615; 564/148; 564/149
(58) Field of Search .................. 514/614, 615; 564/148, 149

(56) References Cited

U.S. PATENT DOCUMENTS 4,012,360 A * 3/1977 Schwarzenbach et al. .. 524/193

(List continued on next page.)

FOREIGN PATENT DOCUMENTS

| WO | WO 94/10995 | 5/1994 |
| WO | WO 99/34796 | 7/1999 |

OTHER PUBLICATIONS

Stalteri, M.A., et al., "Site–specific conjugation and labelling of prostate antibody 7E11C5.3 (CYT–351) with technetium–99m," *European Journal of Nuclear Medicine* 24 (6) :651–654, (1997).

(List continued on next page.)

*Primary Examiner*—Deborah C. Lambkin
(74) *Attorney, Agent, or Firm*—Hamilton, Brook, Smith & Reynolds, P.C.

(57) ABSTRACT

Disclosed is a compound represented by the Structural Formula (I):

$$R_1 \underset{\underset{S}{\|}}{C} - N(R_3) - N(R_5) - C(=Z) - Y - C(=Z) - N(R_6) - N(R_4) - \underset{\underset{S}{\|}}{C} R_2 \quad (I)$$

Y is a covalent bond, a phenylene group or a substituted or unsubstituted straight chained hydrocarbyl group. In addition, Y, taken together with both >C=Z groups to which it is bonded, is a substituted or unsubstituted aromatic group. Preferably, Y is a covalent bond or —C(R$_7$R$_8$)—.

R$_1$ and R$_2$ are independently an aryl group or a substituted aryl group, R$_3$ and R$_4$ are independently —H, an aliphatic group, a substituted aliphatic group, an aryl group or a substituted aryl group.

R$_5$–R$_6$ are independently —H, an aliphatic group, a substituted aliphatic group, an aryl group or a substituted aryl group.

R$_7$ and R$_8$ are each independently —H, an aliphatic or substituted aliphatic group, or R$_7$ is —H and R$_8$ is a substituted or unsubstituted aryl group, or, R$_7$ and R$_8$, taken together, are a C2–C6 substituted or unsubstituted alkylene group.

Z is =O or =S.

Also disclosed are pharmaceutical compositions comprising the compound of the present invention and a pharmaceutically acceptable carrier or diluent.

Also disclosed is a method of treating a subject with cancer by administering to the subject a compound of Structural Formula (I) in combination with taxol or an analog of taxol.

117 Claims, 26 Drawing Sheets

Fig 1. Average Tumor Volume

U.S. PATENT DOCUMENTS

| | | | | |
|---|---|---|---|---|
| 6,172,108 B1 | * | 1/2001 | Vega et al. | 514/485 |
| 6,235,787 B1 | * | 5/2001 | Broadhurst et al. | 514/614 |
| 6,435,787 B1 | * | 8/2002 | John | 410/119 |
| 6,703,426 B1 | * | 3/2004 | Miles et al. | 514/614 |

OTHER PUBLICATIONS

Twomey, D., "Anticancer Agents–IX. Derivatives of Pyridine, Pyridazine and Phthalazine," *Proceedings of the Royal Irish Academy*, vol. 74, Sect. B:37–52, (1974).

Chuyguk, V. A. and Nemazanyj A.G., "Mesoionic Methine Dyes from Biquaternary Salts of Dihetarylmethanes—1,3, 4–Oxa(thia)diazoles and 1,2,4–Triazoles Derivatives," *Ukr. Khim. Zhurn.* 48:520 (1984).

"Remarks" paper as submitted by applicant's attorney.

* cited by examiner

TAXOL ENHANCER COMPOUNDS

RELATED APPLICATIONS

This application claims the benefit of U.S. Provisional Application No. 60/304,252, filed Jul. 10, 2001, and U.S. Provisional Application No. 60/361,946, filed Mar. 6, 2002. The entire teachings of these two applications are incorporated herein by reference.

BACKGROUND OF THE INVENTION

Many new drugs are now available to be used by oncologists in treating patients with cancer. Often, tumors are more responsive to treatment when anti-cancer drugs are administered in combination to the patient than when the same drugs are administered individually and sequentially. One advantage of this approach is that the anti-cancer agents often act synergistically because the tumors cells are attacked simultaneously with agents having multiple modes of action. Thus, it is often possible to achieve more rapid reductions in tumor size by administering these drugs in combination. Another advantage of combination chemotherapy is that tumors are more likely to be eradicated completely and are less likely to develop resistance to the anti-cancer drugs being used to treat the patient.

One serious limitation of combination chemotherapy is that anti-cancer agents generally have severe side effects, even when administered individually. For example, the well known anti-cancer agent taxol causes neutroperia, neuropathy, mucositis, anemia, thrombocytopenia, bradycardia, diarrhea and nausea. Unfortunately, the toxicity of anti-cancer agents is generally additive when the drugs are administered in combination. As result, certain types of anti-cancer drugs are generally not combined. The combined toxic side-effects of those anti-cancer drugs that are administered simultaneously can place severe limitations on the quantities that can be used in combination. Often, it is not possible to use enough of the combination therapy to achieve the desired synergistic effects. Therefore, there is an urgent need for agents which can enhance the desirable tumor attacking properties of anti-cancer agents without further increasing their undesirable side-effects.

SUMMARY OF THE INVENTION

It has now been found that certain bis[thio-hydrazide amide] compounds significantly enhance the anti-cancer activity of taxol. For example, Compound (1) was used in combination with taxol (Paclitaxel) to treat tumors induced in nude mice from the human breast tumor cell line MDA-435. The tumor volume was about five fold less after 24 days of treatment in mice which had been administered 5 mg/kg of taxol and 25 mg/kg of Compound (1) than in mice which had only been administered 5 mg/kg of taxol or in mice which had only been administered 50 mg/kg of Compound (1) (Example 13). These results are shown graphically in FIG. 1. The structure of Compound (1) is shown below:

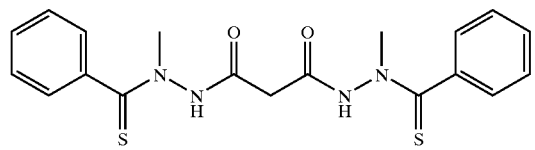

Compound (1)

It has also been found that these bis[thio-hydrazide amide] compounds have minimal toxic side effects. For example, the mice treated with taxol and Compound (1) showed little if any weight loss over the treatment period (see FIG. 2). Based on these results, novel compounds which enhance the anti-cancer activity of taxol, pharmaceutical compositions comprising these compounds and methods of treating a subject with cancer are disclosed herein.

One embodiment of the present invention is a compound represented by the Structural Formula (I):

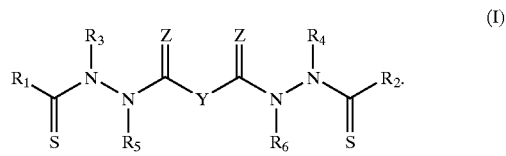

(I)

Y is a covalent bond, a phenylene group or a substituted or unsubstituted straight chained hydrocarbyl group. In addition, Y, taken together with both >C=Z groups to which it is bonded, is a substituted or unsubstituted aromatic group. Preferably, Y is a covalent bond or —C($R_7R_8$)—.

$R_1$ and $R_2$ are independently an aryl group or a substituted aryl group, $R_3$ and $R_4$ are independently —H, an aliphatic group, a substituted aliphatic group, an aryl group or a substituted aryl group.

$R_5$–$R_6$ are independently —H, an aliphatic group, a substituted aliphatic group, an aryl group or a substituted aryl group.

$R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2–C6 substituted or unsubstituted alkylene group.

Z is =O or =S.

In one aspect, $R_1$ and $R_2$ in the compound represented by Structural Formula (I) are not both phenyl when Y is —C($R_7R_8$)—, $R_3$ and $R_4$ are both phenyl and $R_5$–$R_8$ are all —H.

Another embodiment of the present invention is a pharmaceutical composition comprising a pharmaceutically acceptable carrier or diluent and a compound represented by Structural Formula (I). Preferably, the pharmaceutical composition comprises an effective concentration of the compound.

Yet another embodiment of the present invention is a method of treating a subject with cancer. The method comprises administering to the subject an effective amount of taxol or a taxol analog and an effective amount of a compound represented by Structural Formula (I).

The disclosed compounds increase the anti-cancer activity of taxol and taxol analogs. In addition, these compounds have minimal toxic side-effects. Consequently, it is possible to increase the effectiveness of taxol and analogs thereof when used in combination with the disclosed compounds, even when approaching the highest tolerated doses of taxol. Thus, it is expected that combination therapy with the compounds of the present invention will provide improved clinical outcomes for patients with cancers that are being treated with taxol. By co-administering the disclosed compounds with taxol, it is also possible to achieve the same therapeutic effectiveness previously achieved with higher doses of taxol, thereby reducing the side-effects and improving the quality of life for the patient.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
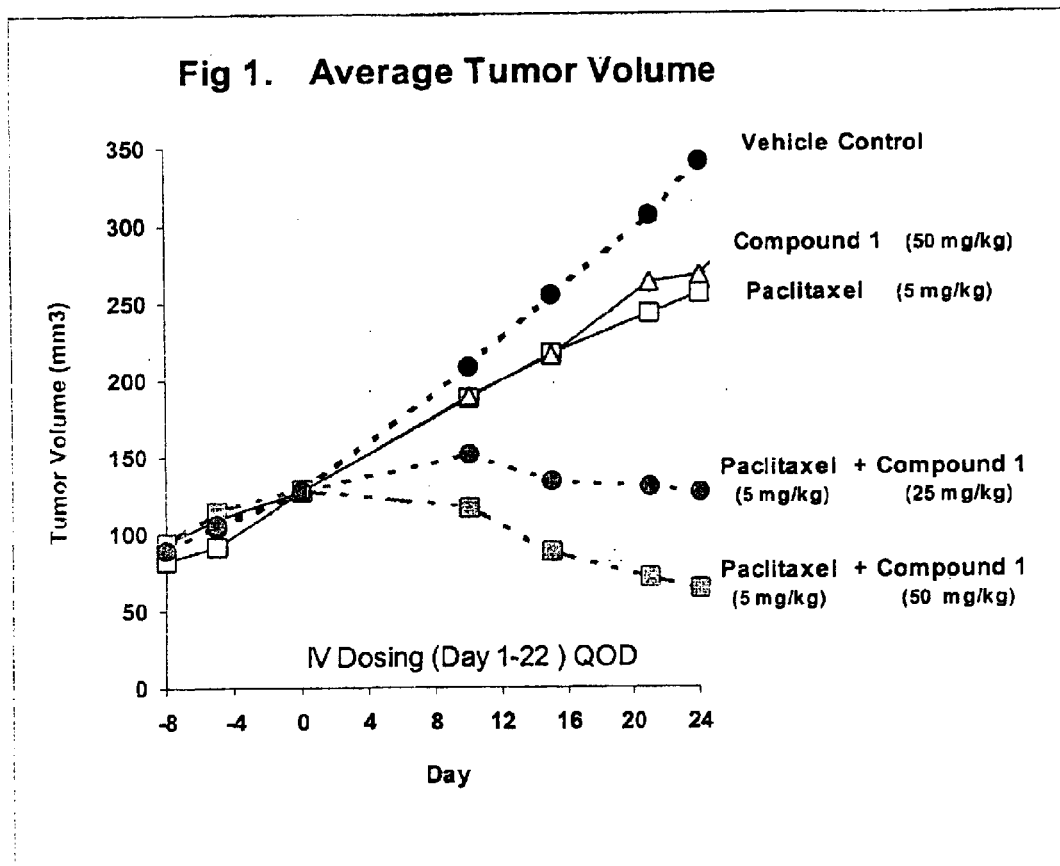
FIG. 1 is a graph showing the average tumor volume in milliliters over time (in days) in nude mice treated with vehicle; Compound (1) (50 mg/kg); Paclitaxel (5 mg/kg); Compound (1) (25 mg/kg) and Paclitaxel (5 mg/kg); or Compound (1) (50 mg/kg) and Paclitaxel (5 mg/kg). The tumors were generated from the human breast tumor cell line MDA-435.

In a first preferred embodiment, Y in Structural Formula (I), taken together with both >C=Z groups to which it is bonded, is a substituted or unsubstituted arylene group and the compound is represented by Structural Formula (II):

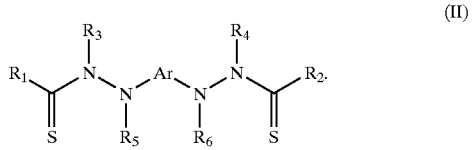

(II)

$R_1$–$R_6$ in Structural Formula (II) are as described in Structural Formula (I). Ar is a substituted or unsubstituted arylene group. Preferably, Ar is a nitrogen-containing heteroarylene group. Examples are shown below:

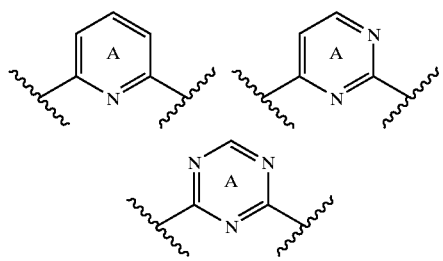

Ring A is substituted or unsubstituted.

In a second preferred embodiment, Y in Structural Formula (I) is a covalent bond or a substituted or unsubstituted straight chained hydrocarbyl group. $R_7$ and $R_8$ are as described for Structural Formula (I). Preferably, Y is a covalent bond, —C($R_7R_8$)—, —(CH$_2$CH$_2$)—, trans-(CH=CH)—, cis-(CH=CH)—, —(CC)— or a 1,4-phenylene group. Even more preferably, Y is a covalent bond or —C($R_7R_8$)—.

In a third preferred embodiment, Y in Structural Formula (I) is a covalent bond or —C($R_7R_8$)— and the compound of the present invention is represented by Structural Formula (III):

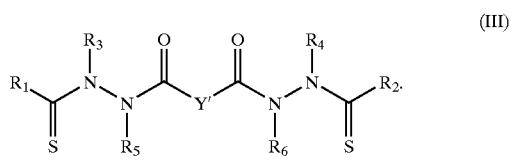

(III)

$R_1$–$R_8$ are as described for Structural Formula (1). Y' is a covalent bond or —C($R_7R_8$)—. Preferably, $R_7$ and $R_8$ are both methyl; $R_7$ and $R_8$, taken together, are propylene or butylene; or $R_7$ is —H and $R_8$ is lower alkyl (preferably methyl), thienyl, phenyl, benzyl, or amino.

In a more preferred embodiment, $R_5$–$R_8$ in Structural Formula (III) are —H and the compound is represented by Structural Formula (IV):

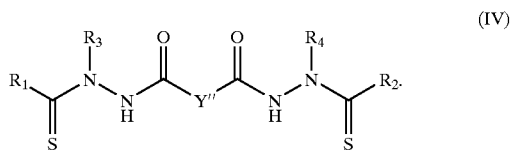

(IV)

$R_1$–$R_4$ in Structural Formula (IV) are as described in Structural Formula (I). Y'' is a covalent bond or —CH$_2$—.

In a first example of a compound represented by Structural Formula (IV), $R_3$ and $R_4$ are both a substituted or unsubstituted aliphatic group, preferably both a substituted or unsubstituted lower alkyl group and more preferably both a methyl group or ethyl. When $R_3$ and $R_4$ in Structural Formula (IV) are both a substituted or unsubstituted aliphatic group, then $R_1$ and $R_2$ are preferably both a substituted or unsubstituted aryl group (e.g., a substituted or unsubstituted heteroaryl group, a substituted or unsubstituted phenyl group, or a phenyl group with at least one substituent other than an aliphatic group).

In a second example of a compound represented by Structural Formula (IV), $R_3$ and $R_4$ are both a substituted or unsubstituted heteroaryl group. When $R_3$ and $R_4$ in Structural Formula (IV) are both a substituted or unsubstituted heteroaryl group, then $R_1$ and $R_2$ are preferably both: 1) a substituted or unsubstituted phenyl group; or 2) a substituted or unsubstituted heteroaryl group.

In a third example of a compound represented by Structural Formula (IV), $R_3$ and $R_4$ are both a substituted or unsubstituted phenyl group (e.g., a phenyl group substituted with at least one group other than an aliphatic group). When $R_3$ and $R_4$ in Structural Formula (IV) are both a substituted or unsubstituted phenyl group, then R and $R_2$ are preferably both: 1) a substituted or unsubstituted phenyl group; or 2) a substituted or unsubstituted heteroaryl group.

In a fourth example of a compound represented by Structural Formula (IV), $R_1$ and $R_2$ are both a substituted or unsubstituted aryl group (e.g., a substituted or unsubstituted heteroaryl group, a substituted or unsubstituted phenyl group or a phenyl group substituted with at least one group other than an aliphatic group). More preferably, $R_3$ and $R_4$ are both methyl and the remainder of the variables are as described above.

In a fourth preferred embodiment, the compound of the present invention is represented by Structural Formula (III), wherein at least one of $R_1$–$R_4$ is a heteroaryl group, a substituted heteroaryl group, or a phenyl group substituted with at least one group other than an aliphatic group. Preferably, $R_5$–$R_8$ are all —H.

The following are specific examples of compounds represented by Structural Formula (IV): $R_1$ and $R_2$ are both phenyl, and $R_3$ and $R_4$ are both o-$CH_3$-phenyl; $R_1$ and $R_2$ are both o-$CH_3C(O)O$-phenyl, and $R_3$ and $R_4$ are phenyl; $R_1$ and $R_2$ are both phenyl, and $R_3$ and $R_4$ are both methyl; $R_1$ and $R_2$ are both phenyl, and $R_3$ and $R_4$ are both ethyl; $R_1$ and $R_2$ are both phenyl, and $R_3$ and $R_4$ are both n-propyl; $R_1$ and $R_2$ are both p-cyanophenyl, and $R_3$ and $R_4$ are both methyl; $R_1$ and $R_2$ are both p-nitro phenyl, and $R_3$ and $R_4$ are both methyl; $R_1$ and $R_2$ are both 2,5-dimethoxyphenyl, and $R_3$ and $R_4$ are both methyl; $R_1$ and $R_2$ are both phenyl, and $R_3$ and $R_4$ are both n-butyl; $R_1$ and $R_2$ are both p-chlorophenyl, and $R_3$ and $R_4$ are both methyl; $R_1$ and $R_2$ are both 3-nitrophenyl, and $R_3$ and $R_4$ are both methyl; $R_1$ and $R_2$ are both 3-cyanophenyl, and $R_3$ and $R_4$ are both methyl; $R_1$ and $R_2$ are both 3-fluorophenyl, and $R_3$ and $R_4$ are both methyl; $R_1$ and $R_2$ are both 2-furanyl, and $R_3$ and $R_4$ are both phenyl; $R_1$ and $R_2$ are both 2-methoxyphenyl, and $R_3$ and $R_4$ are both methyl; $R_1$ and $R_2$ are both 3-methoxyphenyl, and $R_3$ and $R_4$ are both methyl; $R_1$ and $R_2$ are both 2,3-dimethoxyphenyl, and $R_3$ and $R_4$ are both methyl; $R_1$ and $R_2$ are both 2-methoxy-5-chlorophenyl, and $R_3$ and $R_4$ are both ethyl; $R_1$ and $R_2$ are both 2,5-difluorophenyl, and $R_3$ and $R_4$ are both methyl; $R_1$ and $R_2$ are both 2,5-dichlorophenyl, and $R_3$ and $R_4$ are both methyl; $R_1$ and $R_2$ are both 2,5-dimethylphenyl, and $R_3$ and $R_4$ are both methyl; $R_1$ and $R_2$ are both 2-methoxy-5-chlorophenyl, and $R_3$ and $R_4$ are both methyl; $R_1$ and $R_2$ are both 3,6-dimethoxyphenyl, and $R_3$ and $R_4$ are both methyl; $R_1$ and $R_2$ are both phenyl, and $R_3$ and $R_4$ are both 2-ethylphenyl; $R_1$ and $R_2$ are both 2-methyl-5-pyridyl, and $R_3$ and $R_4$ are both methyl; or $R_1$ is phenyl; $R_2$ is 2,5-dimethoxyphenyl, and $R_3$ and $R_4$ are both methyl.

In a fifth preferred embodiment, Y in Structural Formula (I) is —$C(R_7R_8)$— and $R_5$ and $R_6$ are both —H. When Y is a covalent bond or —$CR_7R_8$— and $R_5$ and $R_6$ are both —H, the compound of the present invention is represented by Structural Formula (V):

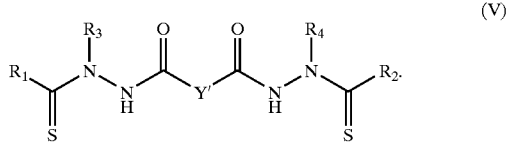

(V)

$R_1$–$R_4$, $R_7$ and $R_8$ are as described for Structural Formula (I) and Y' is a covalent bond or —$CR_7R_8$—. $R_7$ and $R_8$ are the same or different. Preferably, $R_7$ and $R_8$ are both methyl; $R_7$ and $R_8$, taken together, are propylene or butylene; or $R_7$ is —H and $R_8$ is lower alkyl (preferably methyl), thienyl, phenyl or benzyl.

In one example of a compound represented by Structural Formula (V), $R_1$ and $R_2$ are both aryl or substituted aryl groups and $R_3$ and $R_4$ are both a lower alkyl group or a substituted lower alkyl group; preferably, $R_1$ and $R_2$ are both aryl or substituted aryl groups, $R_3$ and $R_4$ are both methyl or ethyl, $R_7$ is —H and $R_8$ is —H or methyl. In another example of a compound represented by Structural Formula (V), $R_1$ and $R_2$ are both phenyl or substituted phenyl and $R_3$ and $R_4$ are both methyl, ethyl, phenyl, or thienyl. When $R_1$ and $R_2$ are both phenyl or substituted phenyl and $R_3$ and $R_4$ are both methyl, ethyl, phenyl, or thienyl, then preferably $R_7$ and $R_8$, taken together, are propylene or butylenes. In yet another example of a compound represented by Structural Formula (V), Y' is a covalent bond or —$CR_7R_8$—; $R_1$ and $R_2$ are both a substituted or unsubstituted aryl group; $R_3$ and $R_4$ are both —H, methyl or ethyl; and $R_7$ is —H and $R_8$ is —H or methyl.

The following are specific examples of compounds represented by Structural Formula (V): $R_1$ and $R_2$ are both phenyl; $R_3$ and $R_4$ are both methyl; $R_7$ is —H, and $R_8$ is ethyl; $R_1$ and $R_2$ are both phenyl; $R_3$ and $R_4$ are both phenyl, and $R_7$ and $R_8$ are both methyl; $R_1$ and $R_2$ are both 2-thienyl; $R_3$ and $R_4$ are both phenyl, and $R_7$ and $R_8$ are both methyl; $R_1$ and $R_2$ are both 4-cyanophenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is benzyl; $R_1$ and $R_2$ are both phenyl; $R_3$ and $R_4$ are both methyl; $R_7$ is —H, and $R_8$ is ethyl; $R_1$ and $R_2$ are both phenyl; $R_3$ and $R_4$ are both ethyl; $R_7$ is —H, and $R_8$ is n-butyl; $R_1$ and $R_2$ are both 2,5-dimethoxyphenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is iso-propyl; $R_1$ and $R_2$ are both 3-nitrophenyl; $R_3$ and $R_4$ are both methyl; $R_7$ is —H, and $R_8$ is methyl; $R^1$ and $R_2$ are both 4-chlorophenyl; $R_3$ and $R_4$ are both methyl; $R_7$ is —H, and $R_8$ is methyl; $R_1$ and $R_2$ are both phenyl; $R_3$ and $R_4$ are both methyl; $R_7$ is —H, and $R_8$ is 3-thienyl; $R_1$ and $R_2$ are both phenyl; $R_3$ and $R_4$ are both methyl, and $R_7$ and $R_8$, taken together, are propylene; $R_1$ and $R_2$ are both 2,3-dimethoxyphenyl; $R_3$ and $R_4$ are both methyl; $R_7$ is —H, and $R_8$ is methyl; $R_1$ and $R_2$ are both 2-chloro-5-methoxy phenyl; $R_3$ and $R_4$ are both methyl; $R_7$ is —H, and $R_8$ is methyl; $R_1$ and $R_2$ are both 2,5-difluorophenyl; $R_3$ and $R_4$ are both methyl; $R_7$ is —H, and $R_8$ is methyl; $R_1$ and $R_2$ are both 2,5-dichlorophenyl; $R_3$ and $R_4$ are both methyl; $R_7$ is —H, and $R_8$ is methyl; $R_1$ and $R_2$ are both 2,6-dimethoxyphenyl; $R_3$ and $R_4$ are both methyl; $R_7$ is —H, and $R_8$ is methyl; $R_1$ and $R_2$ are both 2,5-dimethylphenyl; $R_3$ and $R_4$ are both methyl; $R_7$ is —H, and $R_8$ is methyl; $R_1$ and $R_2$ are both 2,5-dimethoxyphenyl; $R_3$ and $R_4$ are both ethyl; $R_7$ is —H, and $R_8$ is methyl, and R and $R_2$ are both 2,5-diethoxyphenyl; $R_3$ and $R_4$ are both methyl; $R_7$ is —H, and $R_8$ is methyl.

In a sixth preferred embodiment, Y in Structural Formula (I) is a covalent bond or —$CH_2$—. When Y is a covalent bond or —$CH_2$—, the compound of the present invention is represented by Structural Formula (VI):

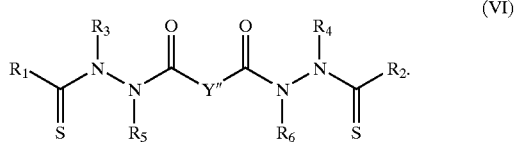

(VI)

$R_1$–$R_6$ in Structural Formula (VI) are as described for Structural Formula (I). $R_5$ and $R_6$ are the same or different. Y" is a covalent bond or —$CH_2$—.

In one example of a compound represented by Structural Formula (VI), $R_5$ and $R_6$ are both a lower alkyl group (preferably methyl) or a phenyl group. When $R_5$ and $R_6$ are both a lower alkyl group or a phenyl group, then $R_1$ and $R_2$ are preferably both phenyl or substituted phenyl and $R_3$ and $R_4$ are preferably both a lower alkyl group.

The following are more specific examples of compounds of the present invention: $R_1$ and $R_2$ are both phenyl, $R_3$ $R_4$ are both phenyl, $R_5$ and $R_6$ are both methyl, and $R_7$ and $R_8$ are both —H; $R_1$ and $R_2$ are both phenyl, $R_3$ and $R_4$ are both phenyl, $R_5$ and $R_6$ are both n-hexyl, and $R_7$ and $R_8$ are both —H; $R_1$ and $R_2$ are both phenyl, $R_3$ and $R_4$ are both methyl, $R_5$ and $R_6$ are both methyl, and $R_7$ and $R_8$ are both —H; $R_1$ and $R_2$ are both phenyl, $R_3$ and $R_4$ are both methyl, $R_5$ and $R_6$ are both methyl, and $R_7$ is —H and R is methyl; $R_1$ and $R_2$ are both phenyl, $R_3$ and $R_4$ are both —H, $R_5$ and $R_6$ are both phenyl, $R_7$ is —H, and $R_8$ is methyl; $R_1$ and $R_2$ are both 4-chlorophenyl, $R_3$ and $R_4$ are both methyl, $R_5$ and $R_6$ are both methyl, and $R_7$ and $R_8$ are both —H.

In Structural Formulas (I)–(VI), $R_1$ and $R_2$ are the same or different; and/or $R_3$ and $R_4$ are the same or different. Preferably, $R_1$ and $R_2$ are the same, and $R_3$ and $R_4$ are the same.

A "straight chained hydrocarbyl group" is an alkylene group, i.e., —$(CH_2)_x$—, with one or more (preferably one) methylene groups optionally replaced with a linkage group. x is a positive integer (e.g., between 1 and about 10), preferably between 1 and about 6 and more preferably 1 or 2. A "linkage group" refers to a functional group which replaces a methylene in a straight chained hydrocarbyl. Examples of suitable linkage groups include a ketone (—C(O)—), alkene, alkyne, phenylene, ether (—O—), thioether (—S—), or amine [—N($R^a$)]—, wherein $R^a$ is defined below. A preferred linkage group is —C($R_7R_8$)—, wherein $R_7$ and $R_8$ are defined above. Suitable substituents for an alkylene group and a hydrocarbaryl group are those which do not substantially interfere with the reactions described herein. $R_7$ and $R_8$ are preferred substituents for an alkylene or hydrocarbyl group.

An aliphatic group is a straight chained, branched or cyclic non-aromatic hydrocarbon which is completely saturated or which contains one or more units of unsaturation. Typically, a straight chained or branched aliphatic group has from 1 to about 20 carbon atoms, preferably from 1 to about 10, and a cyclic aliphatic group has from 3 to about 10 carbon atoms, preferably from 3 to about 8. An aliphatic group is preferably a straight chained or branched alkyl group, e.g, methyl, ethyl, n-propyl, iso-propyl, n-butyl, sec-butyl, tert-butyl, pentyl, hexyl, pentyl or octyl, or a cycloalkyl group with 3 to about 8 carbon atoms. A C1–C20 straight chained or branched alkyl group or a C3–C8 cyclic alkyl group is also referred to as a "lower alkyl" group.

Aromatic groups include carbocyclic aromatic groups such as phenyl, naphthyl, and anthracyl, and heteroaryl groups such as imidazolyl, thienyl, furanyl, pyridyl, pyrimidy, pyranyl, pyrazolyl, pyrroyl, pyrazinyl, thiazole, oxazolyl, and tetrazole.

Aromatic groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazole, benzooxazole, benzimidazole, quinolinyl, isoquinolinyl and isoindolyl.

The term "arylene" refers to an aryl group which is connected to the remainder of the molecule by two other bonds. By way of example, the structure of a 1,4-phenylene group is shown below:

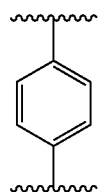

Substituents for an arylene group are as described below for an aryl group.

Non-aromatic heterocyclic rings are non-aromatic carbocyclic rings which include one or more heteroatoms such as nitrogen, oxygen or sulfur in the ring. The ring can be five, six, seven or eight-membered. Examples include tetrahydrofuranyl, tetrahyrothiophenyl, morpholino, thiomorpholino, pyrrolidinyl, piperazinyl, piperidinyl, and thiazolidinyl.

The terms "lower alkoxy", "lower acyl", "(lower alkoxy) methyl" and "(lower alkyl)thiomethyl" mean to —O-(lower alkyl), —C(O)-(lower alkyl), —$CH_2$—O-(lower alkyl) and —$CH_2$—S-(lower alkyl), respectively. The terms "substituted lower alkoxy" and "substituted lower acyl" mean —O-(substituted lower alkyl) and —C(O)-(substituted lower alkyl), respectively.

Suitable substituents on an aliphatic group, non—aromatic heterocyclic group, benzylic or aryl group (carbocyclic and heteroaryl) are those which do not substantially interfere with the ability of the disclosed compounds to enhance the anti—cancer activity of taxol and analogs thereof. A substituent substantially interferes with the ability of a disclosed compound to enhance anti—cancer activity when the enhancement is reduced by more than about 50% in a compound with the substituent compared with a compound without the substituent. Examples of suitable substituents include —OH, halogen (—Br, —Cl, —I and —F), —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —CON$(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR_c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—N$(R^aR^b)$, —$NR^dH$—C(=NH)—$NH_2$, —$NR^d$—C(=NH)—$NHR^a$, —$NR^d$—C(=NHH)—N$(R^aR^b)$, —$NR^d$—C(=$NR^c$)—$NH_2$, —$NR^d$—C(=$NR^c$)—$NHR^a$, —$NR^d$—C(=$NR^c$)—N$(R^aR^b)$, —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, C$R^c$=$R^aR^b$, —C$R^c$=$CHR^a$, —$CR^c$=$CR^aR^b$, —$CCR^a$—SH, —$SO_kR^a$(k is 0, 1 or 2) and —NH—C(=NH)—$NH_2$. $R^a$–$R^d$ are each independently an aliphatic, substituted aliphatic, benzyl, substituted benzyl, aromatic or substituted aromatic group, preferably an alkyl, benzylic or aryl group. In addition, [[—$NR^aR^d$]]—N$(R^aR^b)$, taken together, can also form a substituted or unsubstituted non-aromatic heterocyclic group. A non-aromatic heterocyclic group, benzylic group or aryl group can also have an aliphatic or substituted aliphatic group as a substituent. A substituted aliphatic group can also have a non-aromatic heterocyclic ring, a substituted a non-aromatic heterocyclic ring, benzyl, substituted benzyl, aryl or substituted aryl group as a substituent. A substituted aliphatic, non-aromatic heterocyclic group, substituted aryl, or substituted benzyl group can have more than one substituent.

Also included in the present invention are pharmaceutically acceptable salts of the compounds described herein. The compound of the present invention which possess a sufficiently acidic, a sufficiently basic, or both functional groups, and accordingly can react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

Figure 4:
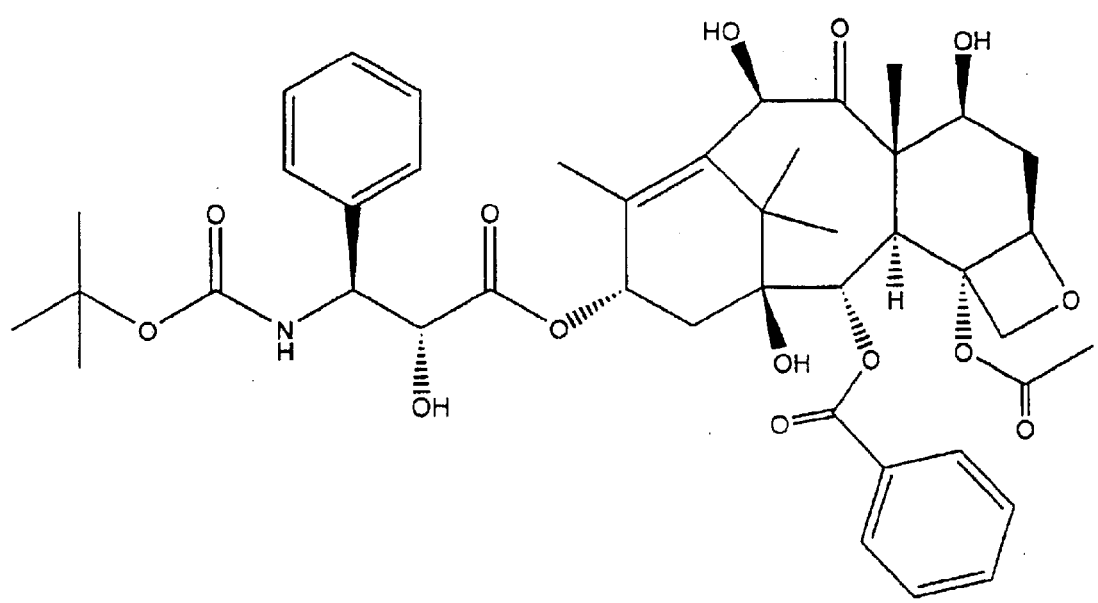
FIG. 4 is the structure of taxotere (Docetaxel)
Figure 5:
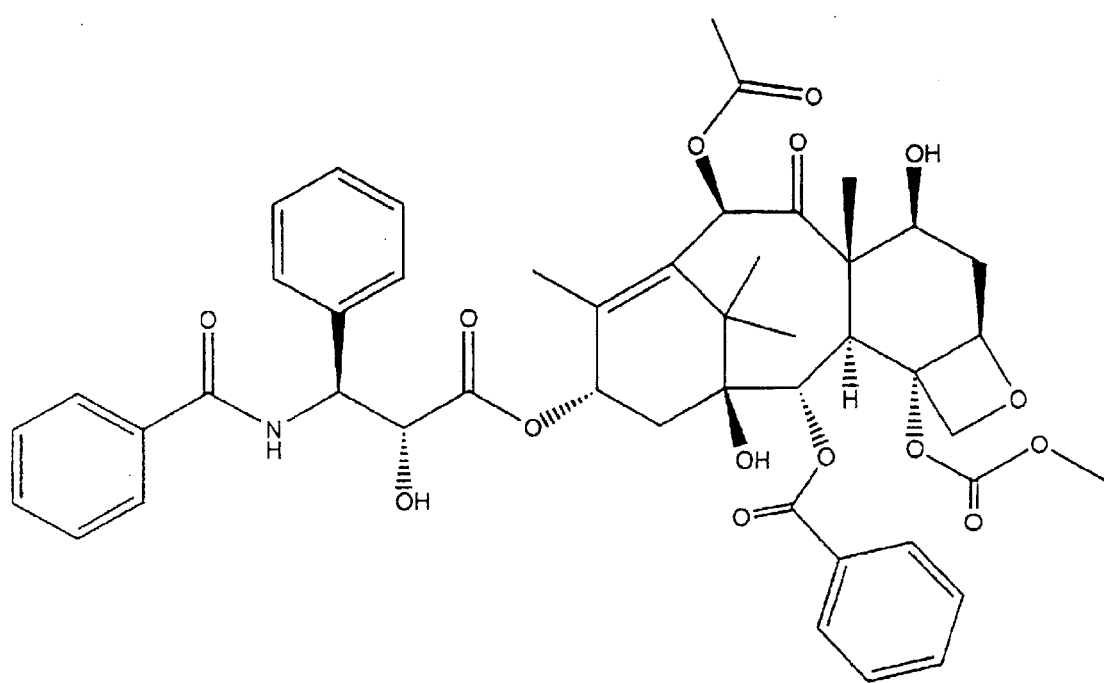
FIGS. 5–25 are each the structure of a taxol analog.
Figure 6:
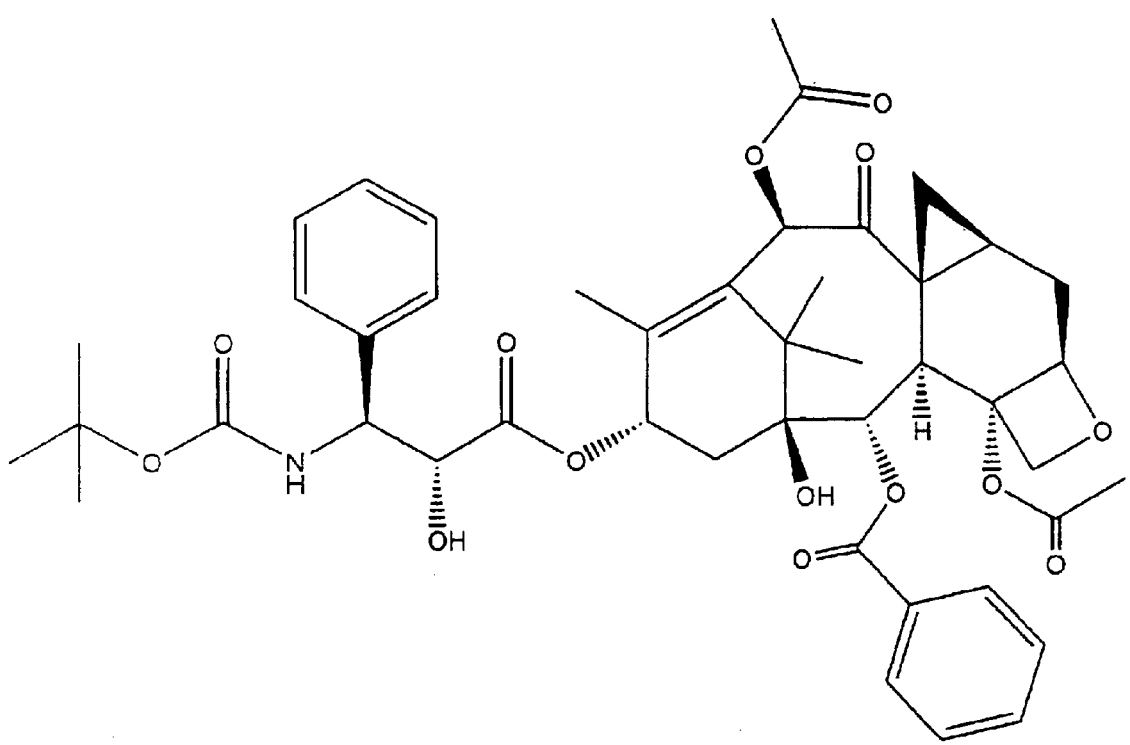
Figure 7:
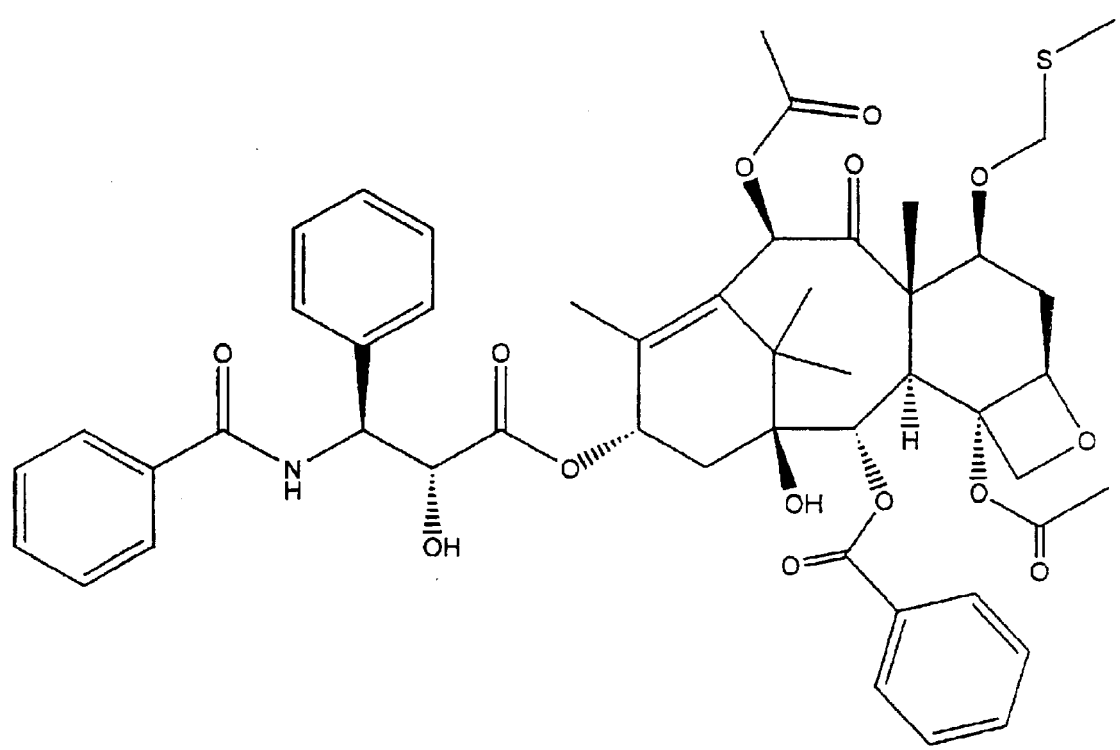
Figure 8:
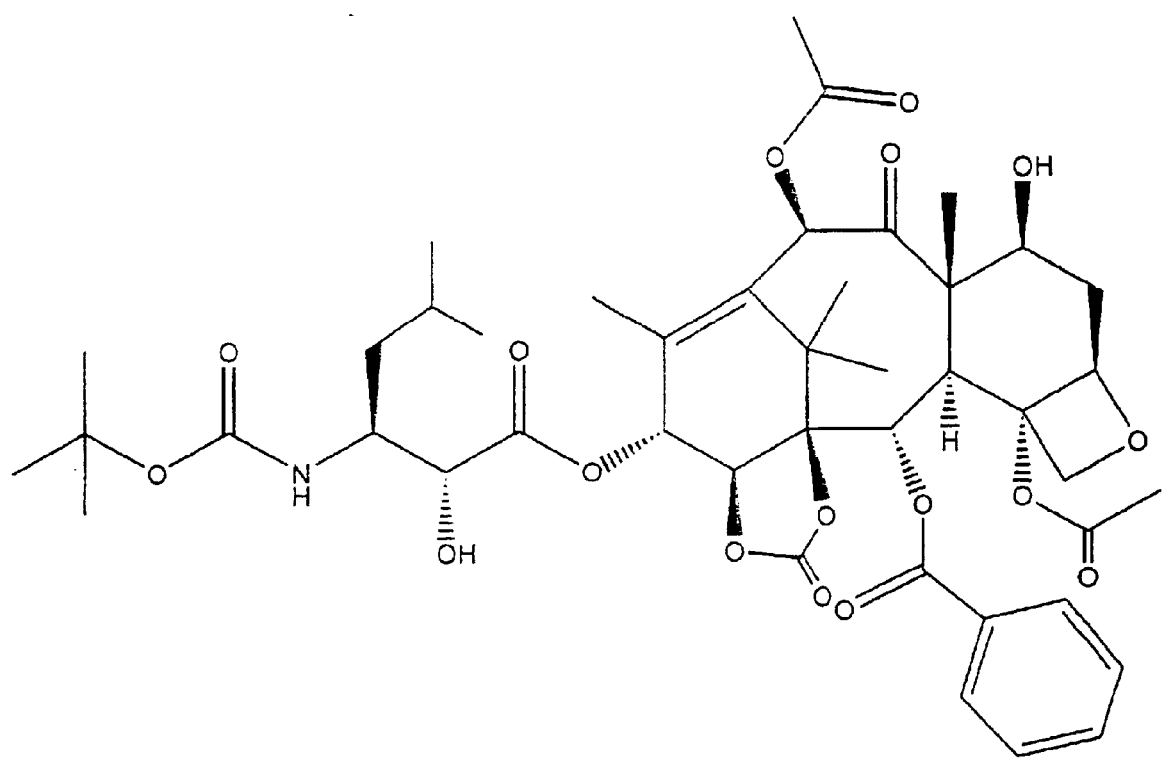
Figure 9:
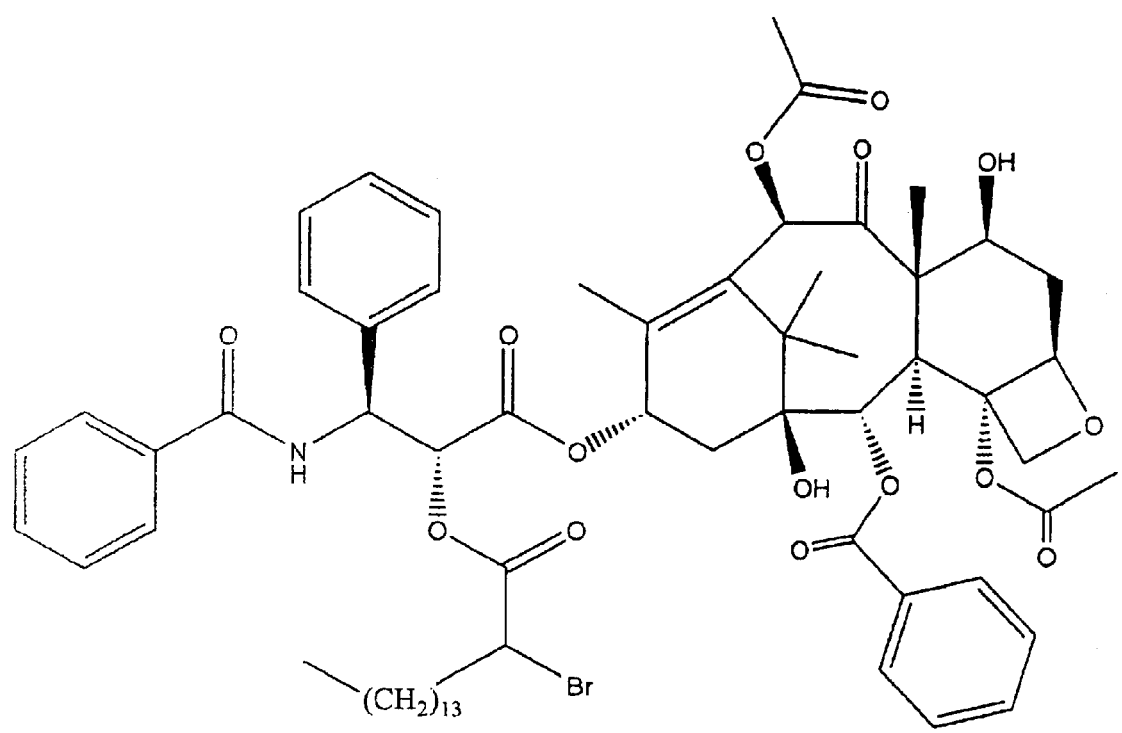
Figure 10:
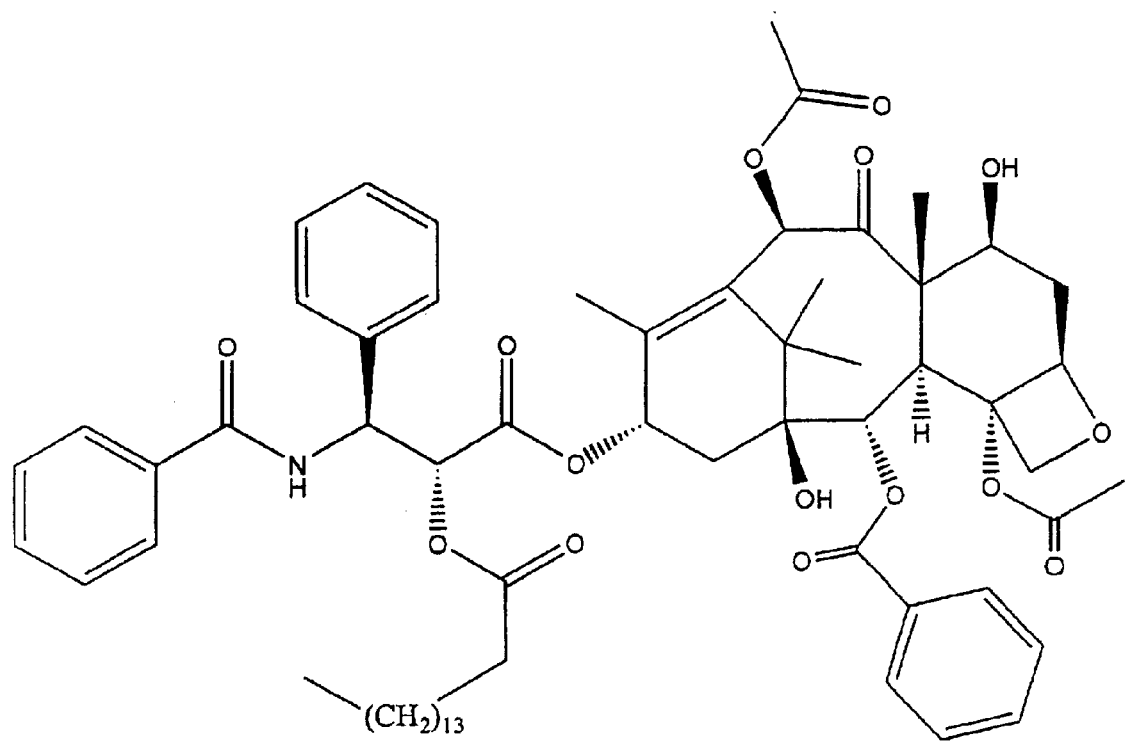
Figure 11:
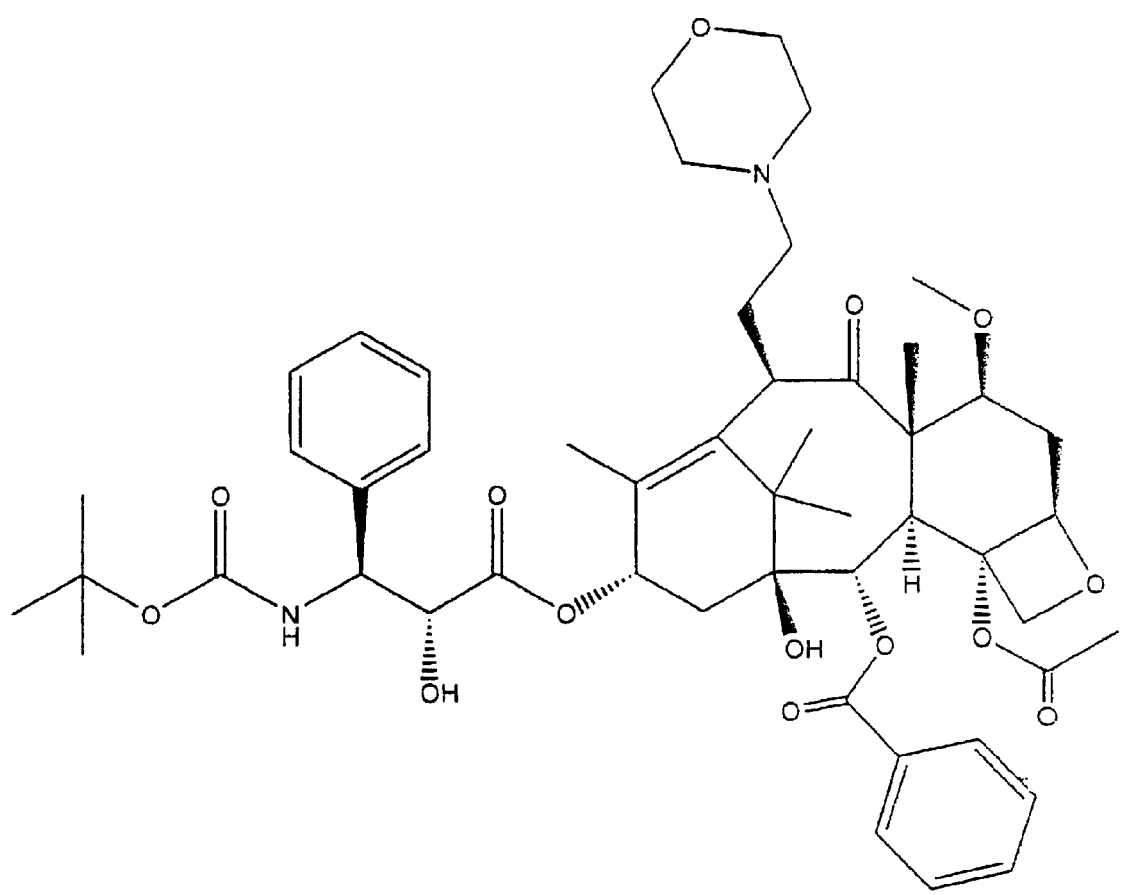
Figure 12:
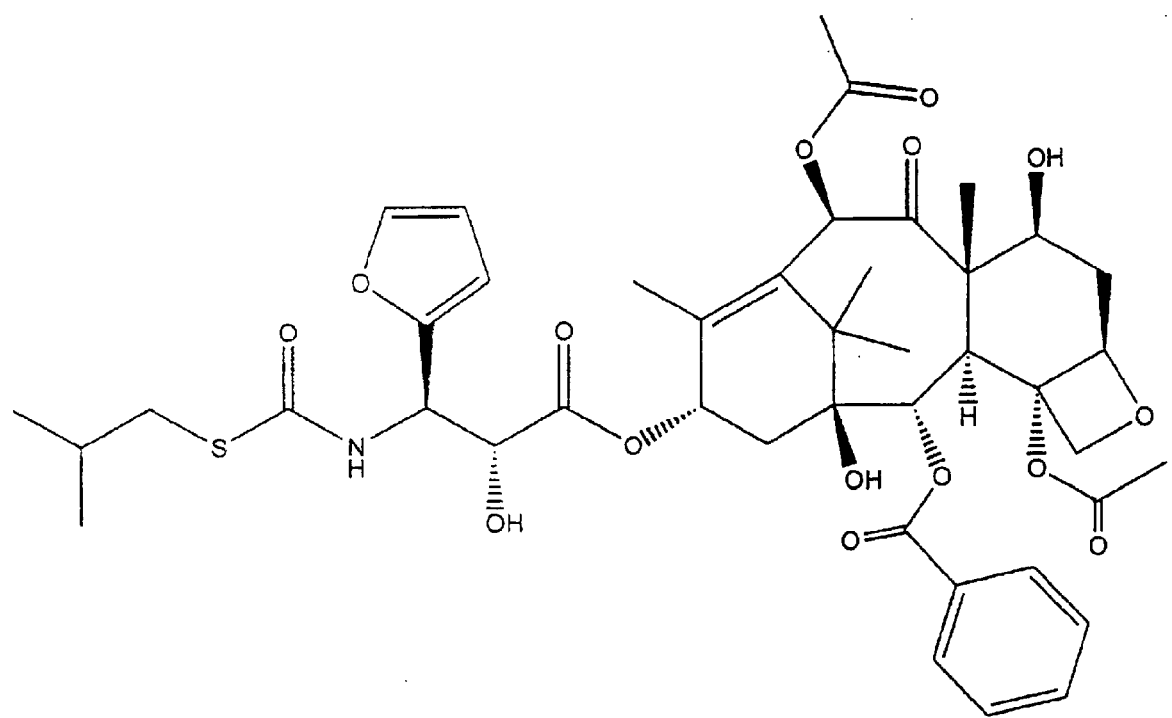
Figure 13:
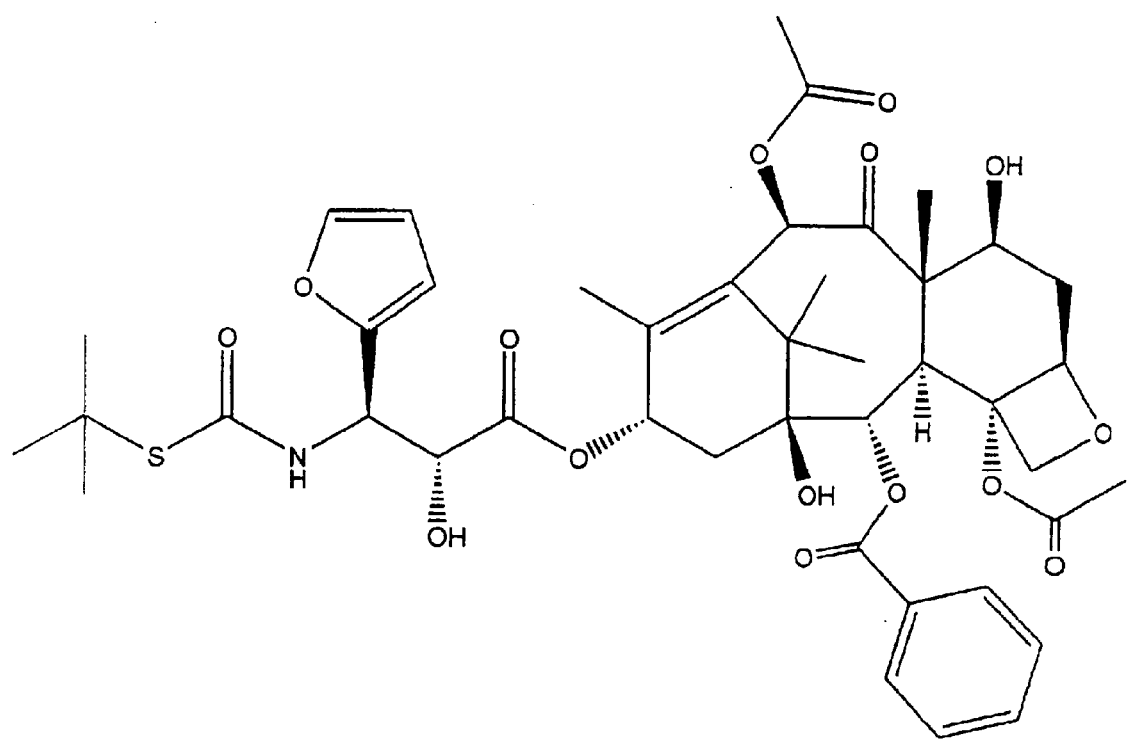
Figure 14:
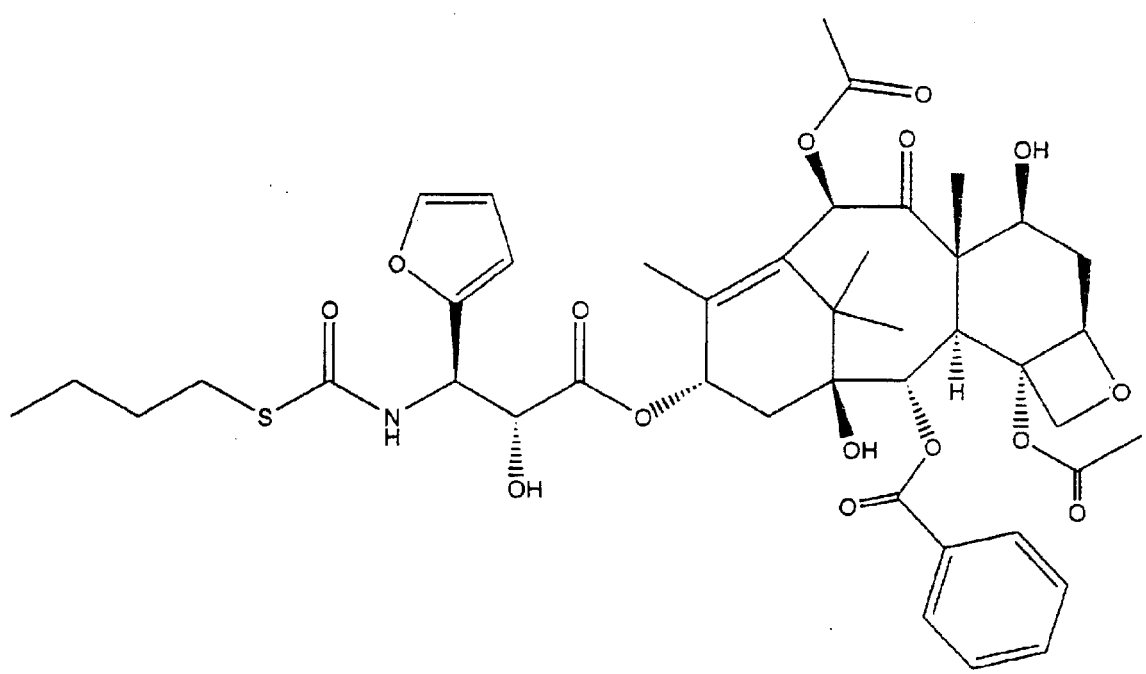
Figure 15:
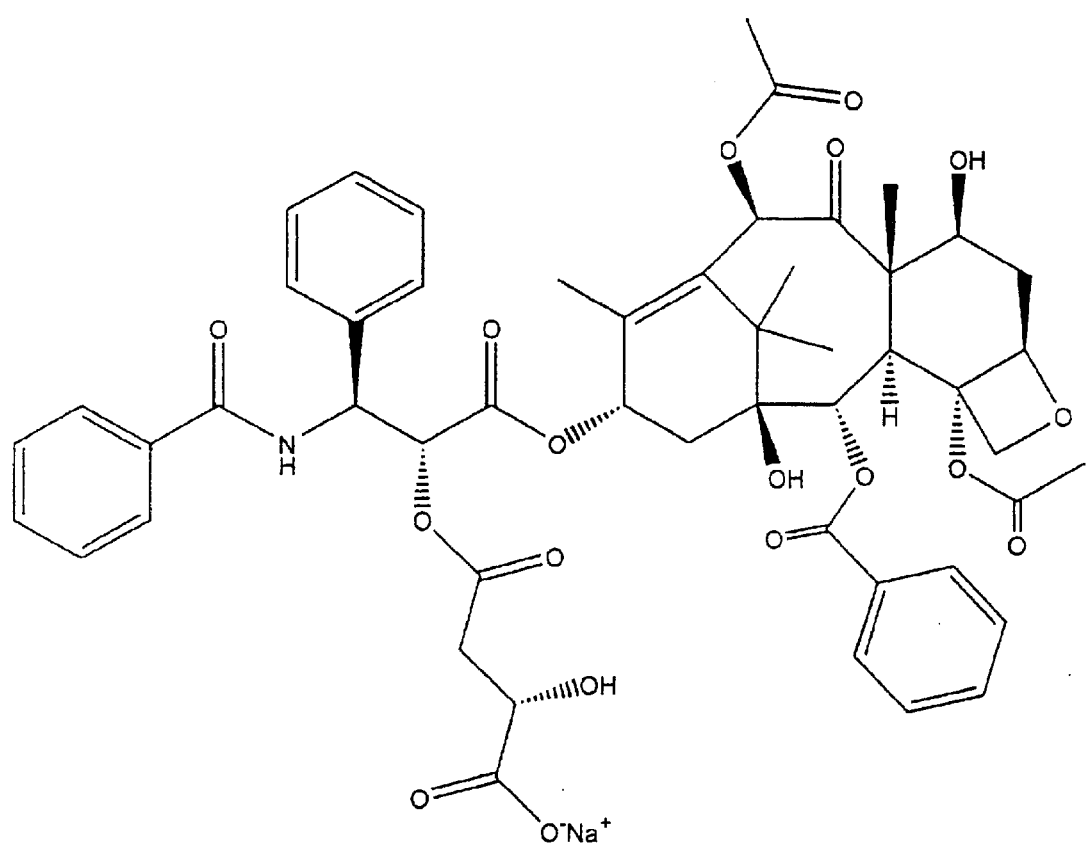
Figure 16:
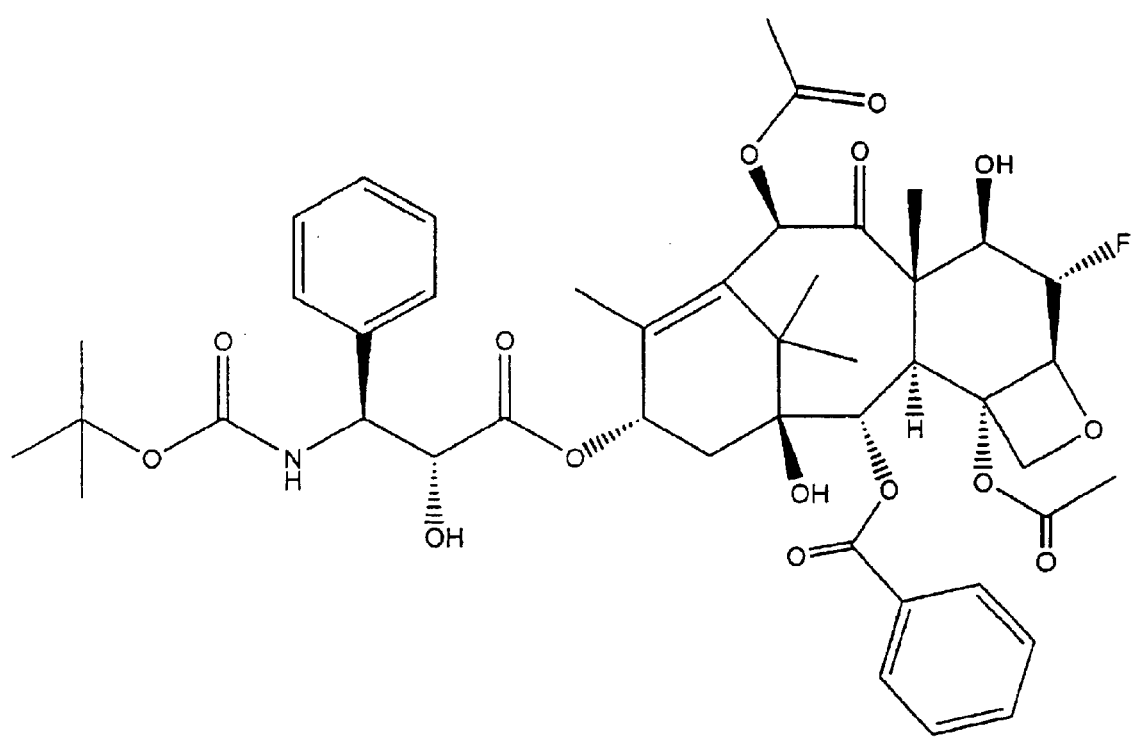
Figure 17:
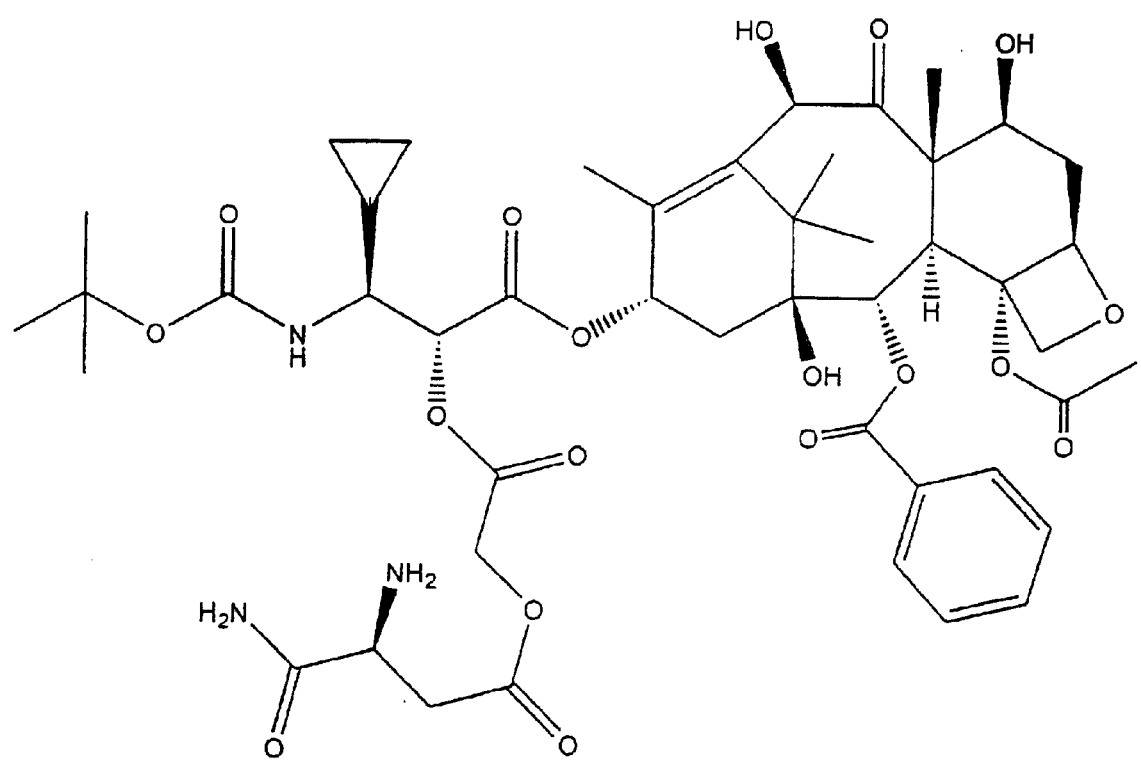
Figure 18:
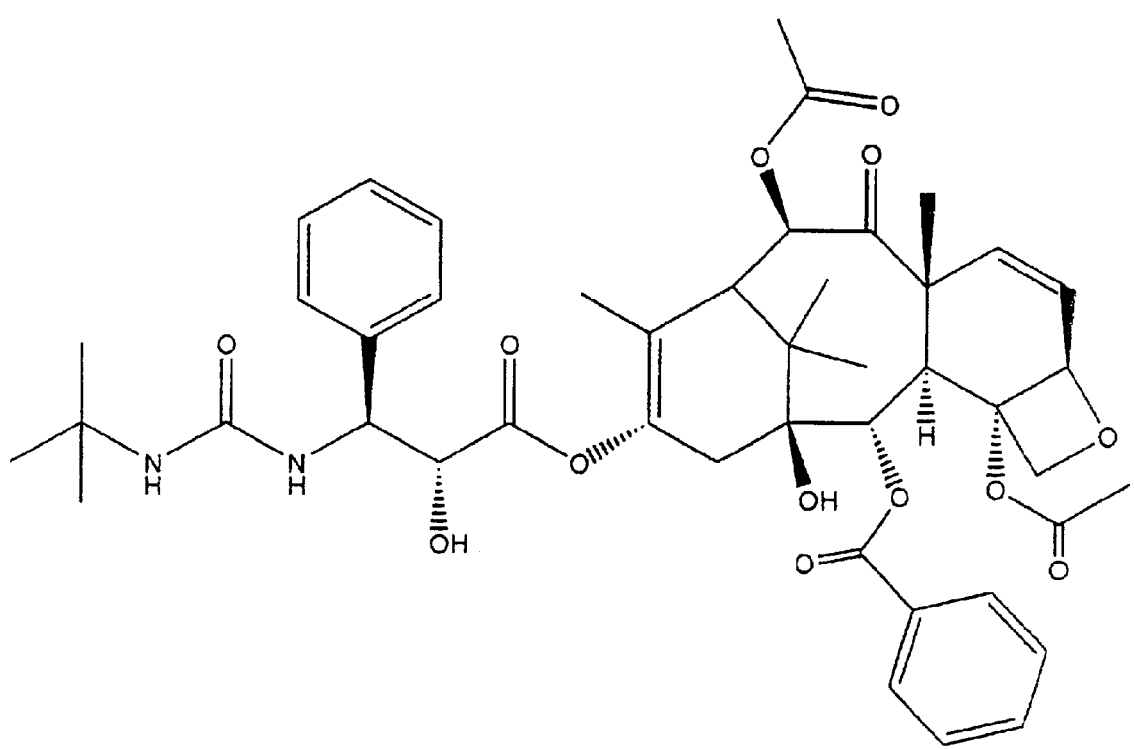
Figure 19:
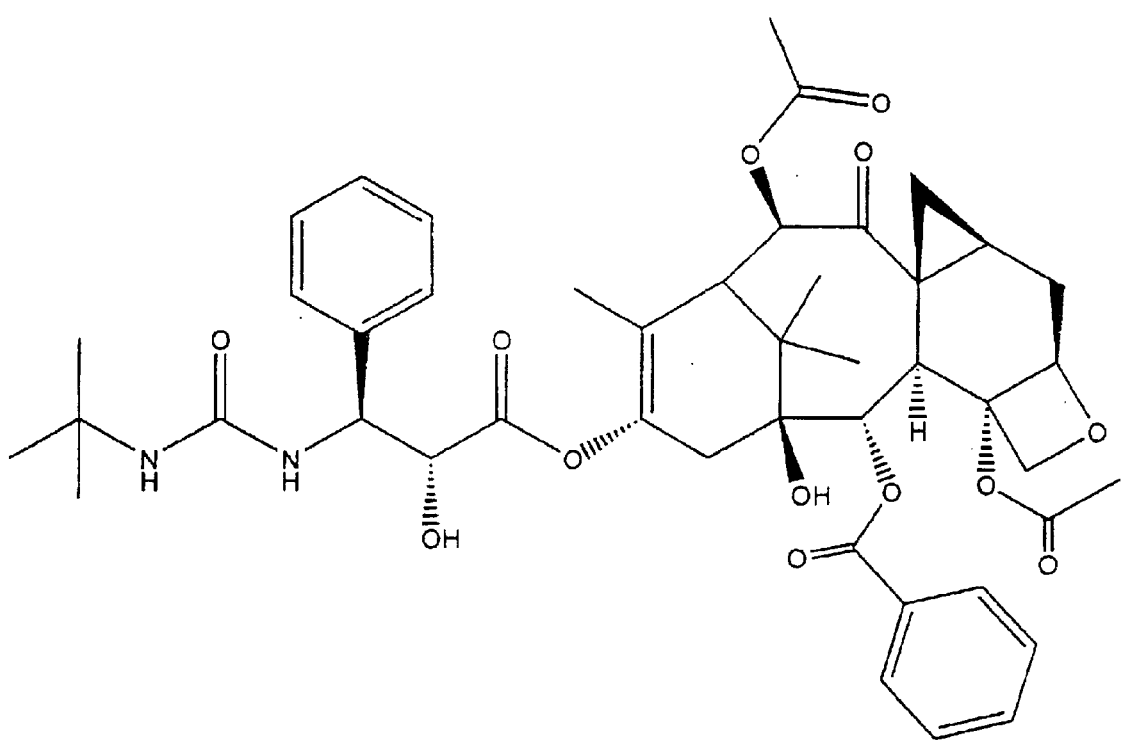
Figure 20:
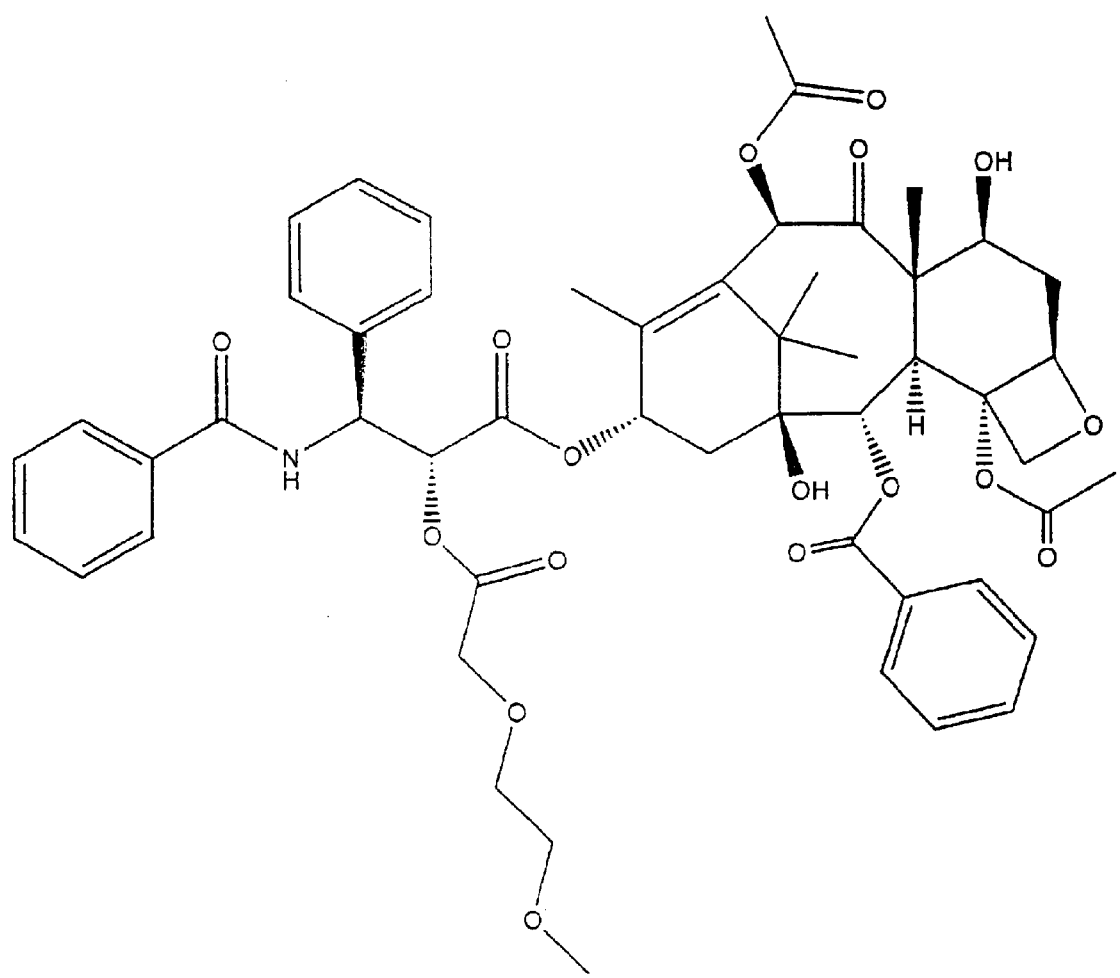
Figure 21:
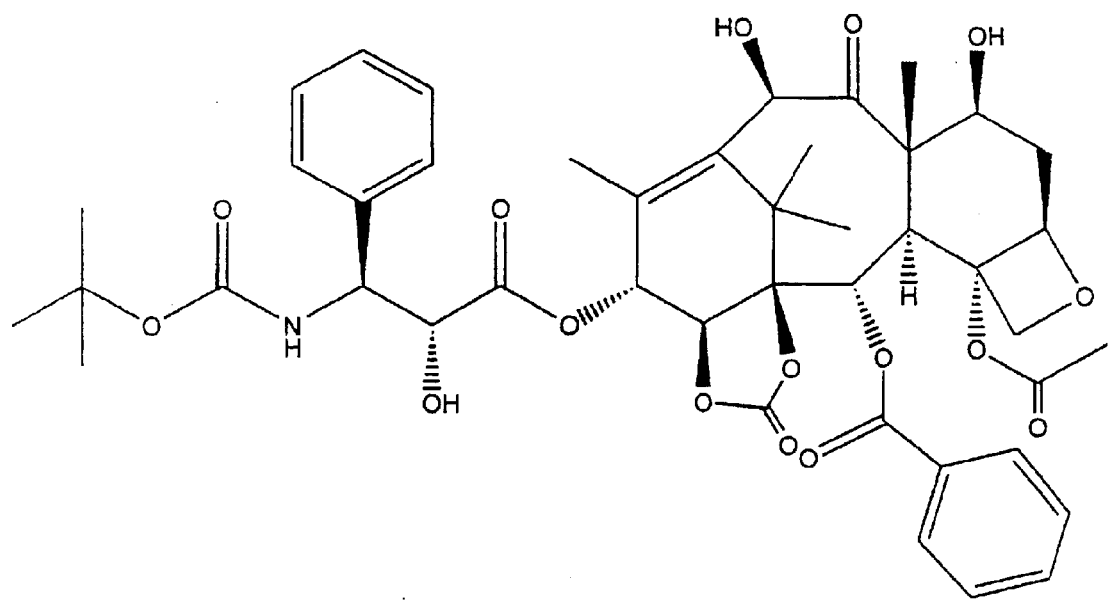
Figure 22:
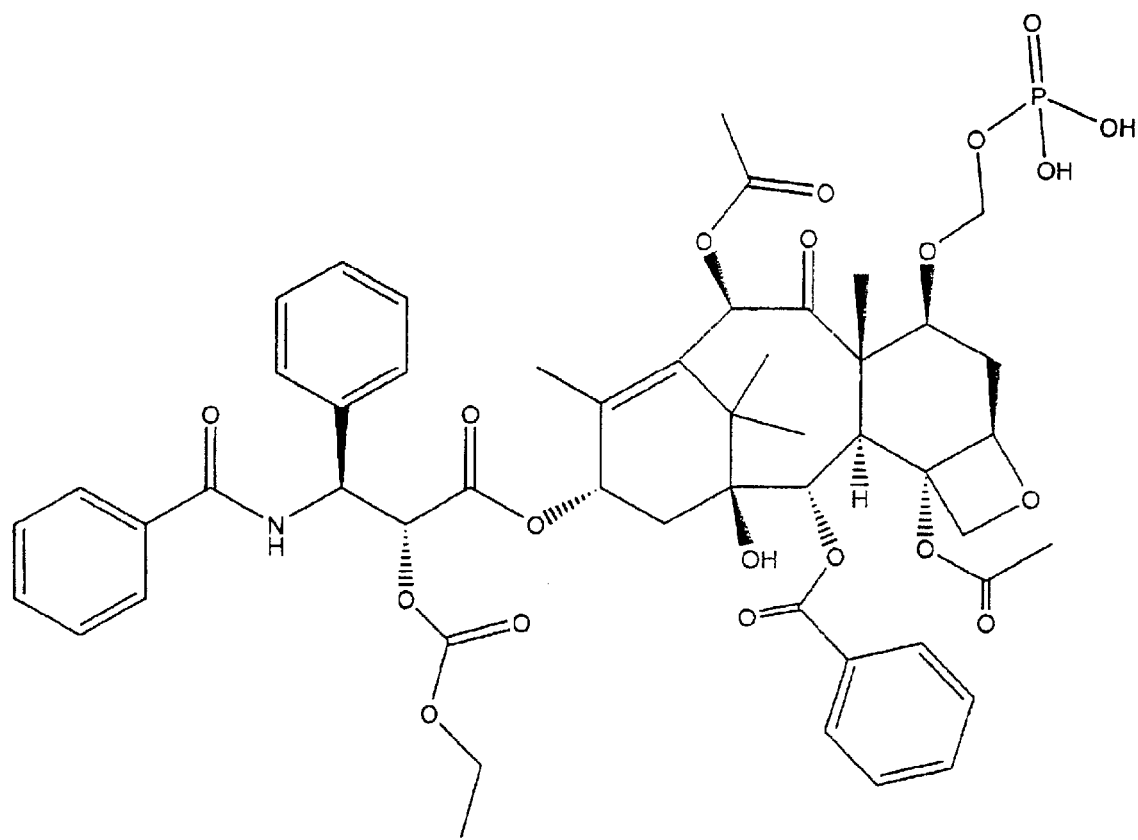
Figure 23:
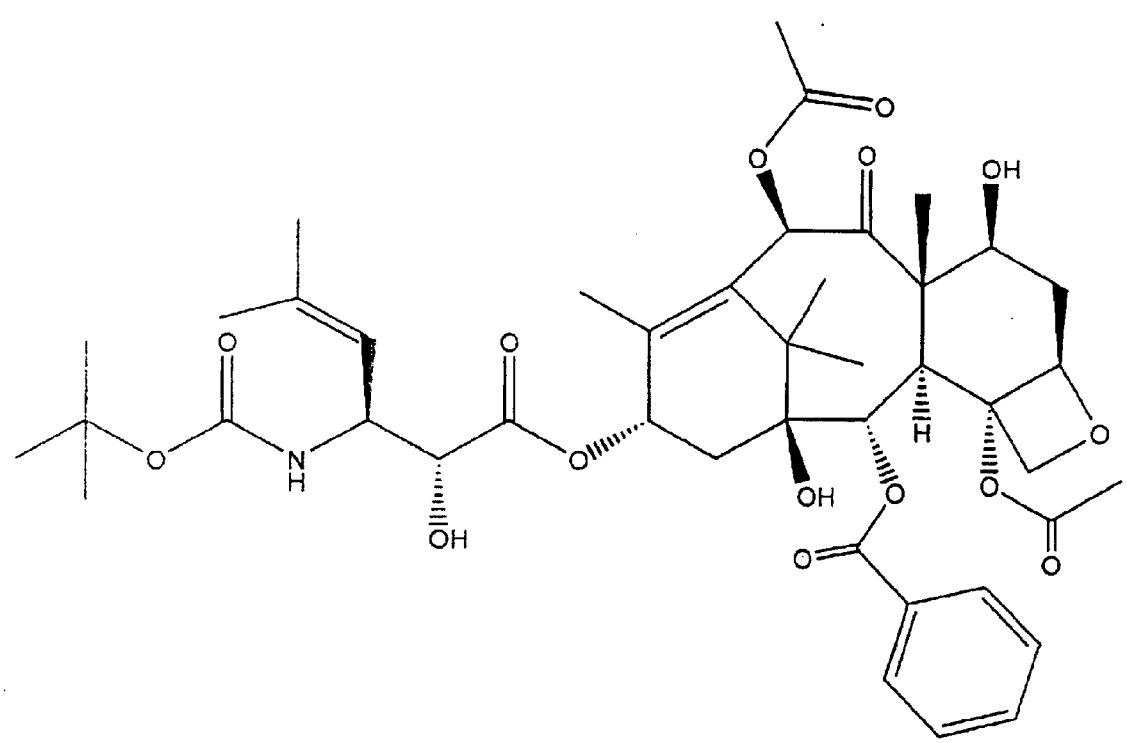
Figure 24:
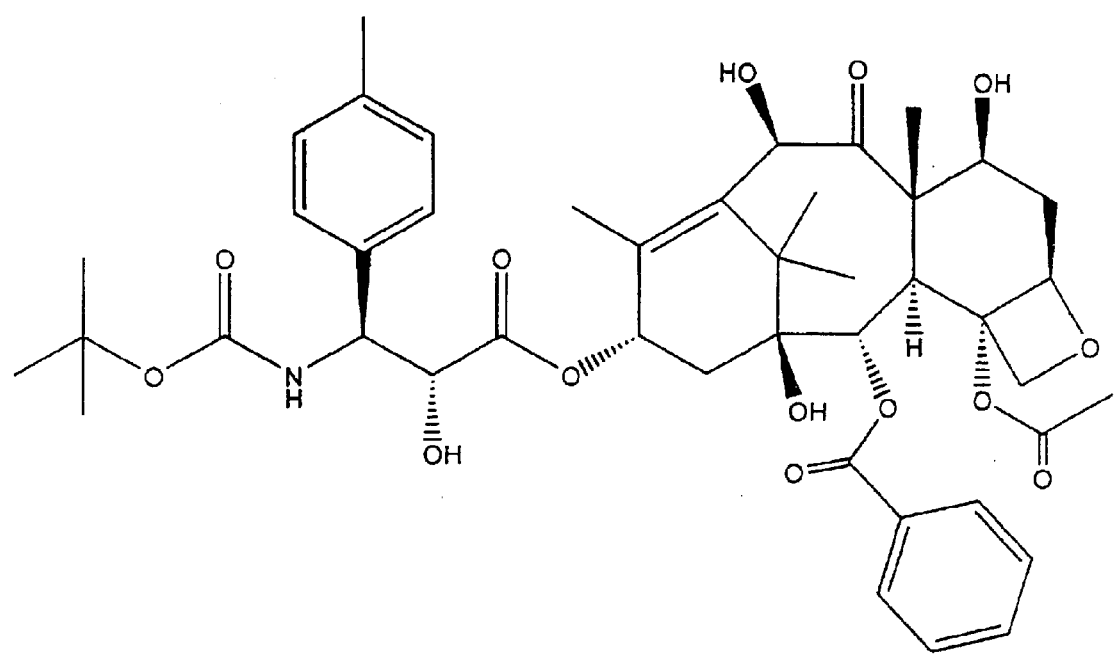
Figure 25:
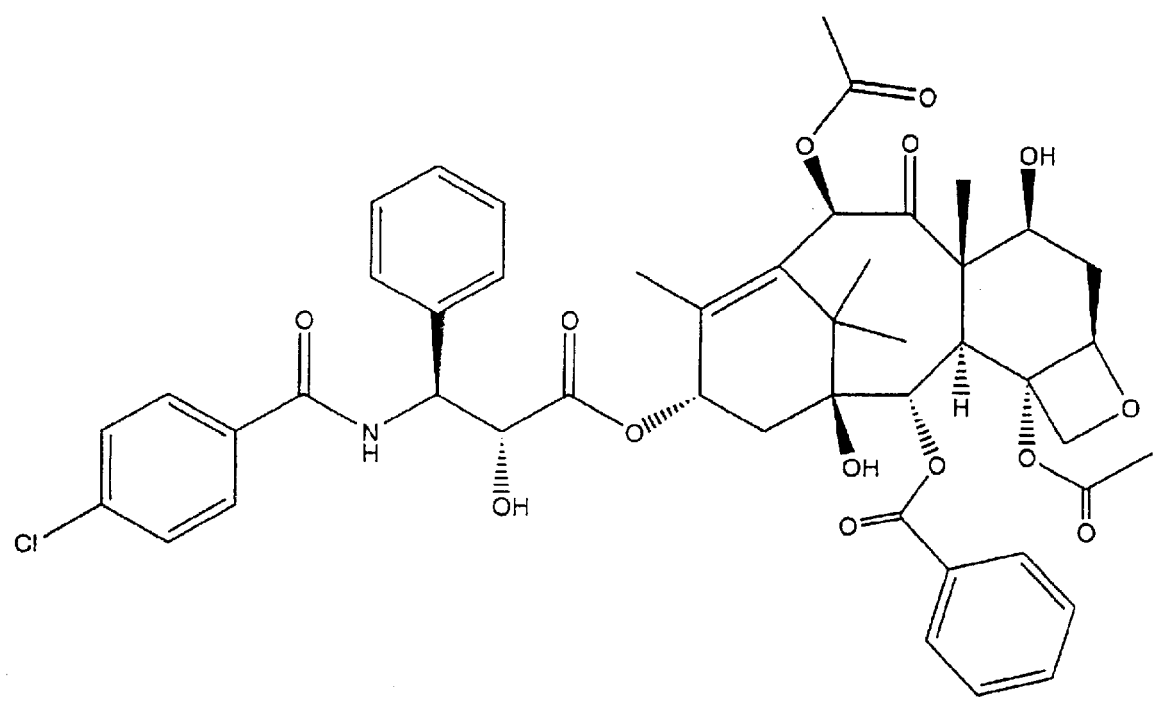

Taxol, also referred to as "Paclitaxel", is a well-known anti-cancer drug which acts by inhibiting microtubule formation. Many analogs of taxol are known, including taxotere, the structure of which is shown in FIG. 4. Taxotere is also referred to as " "Docetaxol". The structure of other taxol analogs are shown in FIGS. 5–25. These compounds have the basic taxane skeleton as a common structure feature and have also been shown to have the ability to arrest cells in the G2-M phases due to stabilized microtubules. Thus, it is apparent from FIGS. 5–25 that a wide variety of substituents can decorate the taxane skeleton without adversely affecting biological activity. It is also apparent that zero, one or both of the cyclohexane rings of a taxol analog can have a double bond at the indicated positions. For clarity purposes, the basic taxane skelton is shown below in Structural Formula (VII):

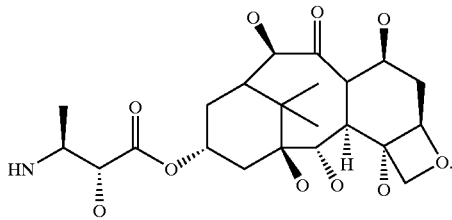

(VII)

Double bonds have been omitted from the cyclohexane rings in the taxane skeleton represented by Structural Formula (VII). It is to be understood that the basic taxane skeleton can include zero or one double bond in one or both cyclohexane rings, as indicated in FIGS. 5–25 and Structural Formulas (VIII) and (IX) below. A number of atoms have also omitted from Structural Formula (VII) to indicate sites in which structural variation commonly occurs among taxol analogs. For example, substitution on the taxane skeleton with simply an oxygen atom indicates that hydroxyl, acyl, alkoxy or other oxygen-bearing substituent is commonly found at the site. It is to be understood that these and other substitutions on the taxane skeleton can also be made without losing the ability to enhance and stabilize microtubule formation. Thus, the term "taxol analog" is defined herein to mean a compound which has the basic taxol skeleton and which promotes disassembly of microtubules.

Typically, the taxol analogs used herein are represented by Structural Formula (VIII) or (IX):

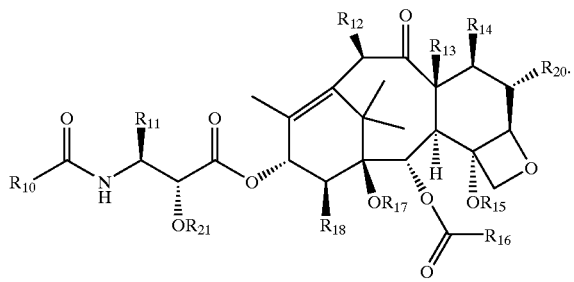

(VIII)

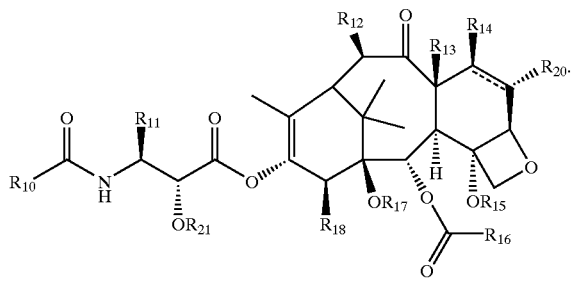

(IX)

$R_{10}$ is a lower alkyl group, a substituted lower alkyl group, a phenyl group, a substituted phenyl group, $-SR_{19}$, $-NHR_{19}$ or $-OR_{19}$.

$R_{11}$ is a lower alkyl group, a substituted lower alkyl group, an aryl group or a substituted aryl group.

$R_{12}$ is $-H$, $-OH$, lower alkyl, substituted lower alkyl, lower alkoxy, substituted lower alkoxy, $-O-C(O)$-(lower alkyl), $-O-C(O)$-(substituted lower alkyl), $-O-CH_2-$ O-(lower alkyl) $-S-CH_2-O$-(lower alkyl).

$R_{13}$ is $-H$, $-CH_3$, or, taken together with $R_{14}$, $-CH_2-$.

$R_{14}$ is $-H$, $-OH$, lower alkoxy, $-O-C(O)$-(lower alkyl), substituted lower alkoxy, $-O-C(O)$-(substituted lower alkyl), $-O-CH_2-O-P(O)(OH)_2$, $-O-CH_2-O$-(lower alkyl), $-O-CH_2-S$-(lower alkyl) or, taken together with $R_{20}$, a double bond.

$R_{15}$ $-H$, lower acyl, lower alkyl, substituted lower alkyl, alkoxymethyl, alkthiomethyl, $-OC(O)-O$(lower alkyl), $-OC(O)-O$(substituted lower alkyl), $-OC(O)-NH$ (lower alkyl) or $-OC(O)-NH$(substituted lower alkyl).

$R_{16}$ is phenyl or substituted phenyl.

$R_{17}$ is $-H$, lower acyl, substituted lower acyl, lower alkyl, substituted, lower alkyl, (lower alkoxy)methyl or (lower alkyl)thiomethyl.

$R_{18}$ $-H$, $-CH_3$ or, taken together with $R_{17}$ and the carbon atoms to which R and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is $-H$ or a halogen.

$R_{21}$ is $-H$, lower alkyl, substituted lower alkyl, lower acyl or substituted lower acyl.

Preferably, the variables in Structural Formulas (VIII) and (IX) are defined as follows: $R_{10}$ is phenyl, tert-butoxy, $-S-CH_2-CH-(CH_3)_2$, $-S-CH(CH_3)_3$, $-S-(CH_2)_3CH_3$, $-O-CH(CH_3)_3$, $-NH-CH(CH_3)_3$, $-CH=C(CH_3)_2$ orpara-chlorophenyl; $R_1$ is phenyl, $(CH_3)_2CHCH_2-$, -2-furanyl, cyclopropyl orpara-toluyl; $R_{12}$ is $-H$, $-OH$, $CH_3CO-$ or $-(CH_2)_2-N$-morpholino; $R_{13}$ is methyl, or, $R_{13}$ and $R_{14}$, taken together, are $-CH_2-$;

$R_{14}$ is —H, —$CH_2SCH_3$ or —$CH_2$—O—P(O)(OH)$_2$; $R_{15}$ is $CH_3CO$—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Figure 26:
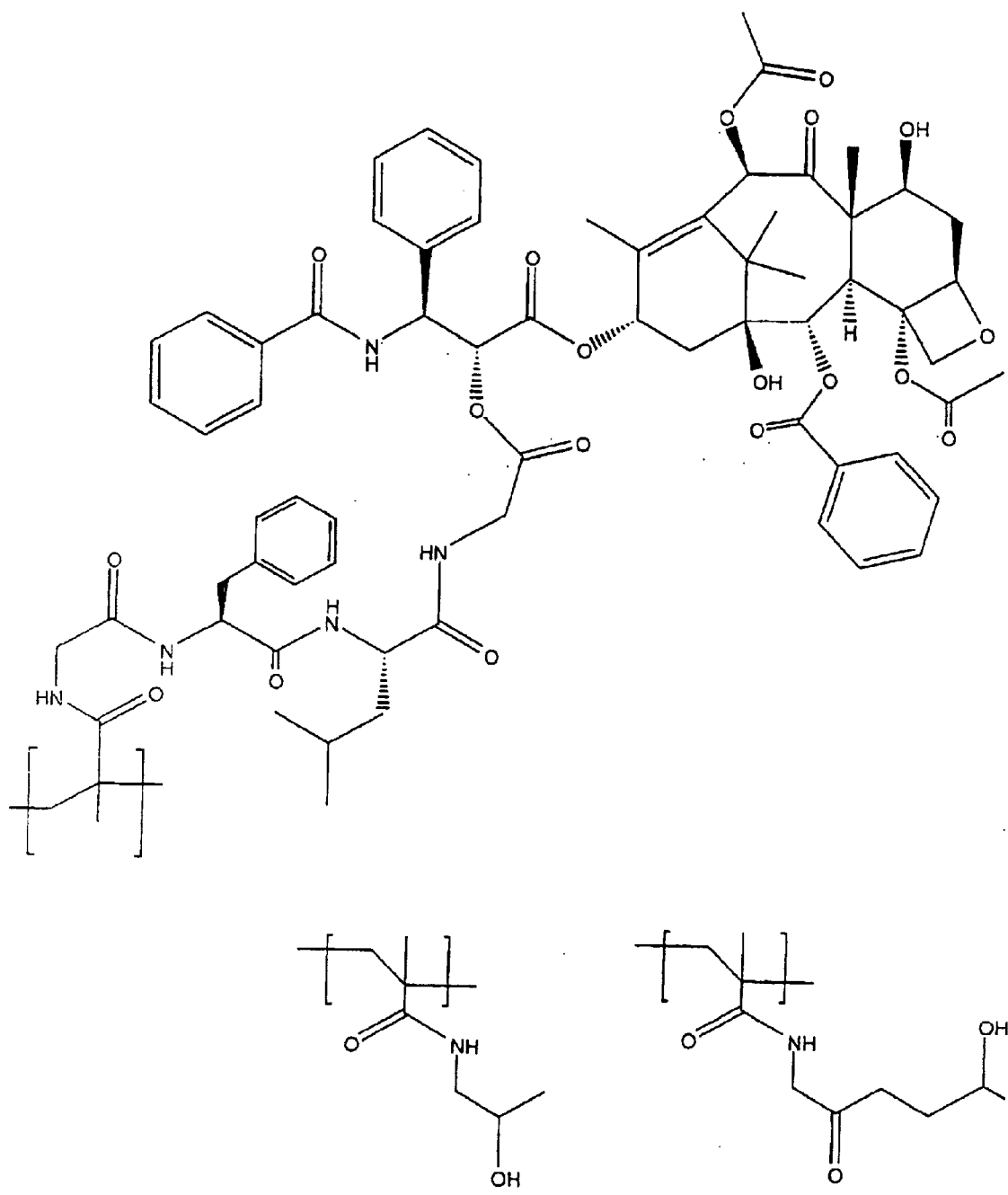
FIG. 26 is the structure of a polymer comprising a taxol analog group pendent from the polymer backbone. The polymer is a terpolymer of the three monomer units shown.

A taxol analog can also be bonded to or be pendent from a pharmaceutically acceptable polymer, such as a polyacrylamide. One example of a polymer of this type is shown in FIG. 26. The term "taxol analog", as it is used herein, includes such polymers.

The disclosed compounds are enhancers of the anti-cancer activity of taxol and taxol analogs. A compound enhances the anti-cancer activity of taxol or a taxol analog when the activity of taxol or the taxol analog is greater when administered in combination with the compound than when administered alone. The degree of the increase in activity depends upon the amount of compound administered. The compounds of the present invention can therefore be used in combination with taxol or taxol analogs to treat subjects with cancers. Examples include colon cancer, pancreatic cancer, melanoma, renal cancer, sarcoma, breast cancer, ovarian cancer, lung cancer. stomach cancer, bladder cancer and cervical cancer.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In order to achieve an enhancement of the anti-cancer activity of taxol and taxol analogs, an effective amount of a compound of the present invention and an effective amount of taxol or analog of taxol are administered to the subject. With respect to taxol or an analog of taxol, an "effective amount" is a quantity in which anti-cancer effects are normally achieved. With respect to a compound of the present invention, an "effective amount" is the quantity in which a greater anti-cancer effect is achieved when the compound is co-administered with taxol or a taxol analog compared with when taxol or the taxol analog is administered alone. The compound and taxol (or taxol analog) can be co-administered to the subject as part of the same pharmaceutical composition or, alternatively, as separate pharmaceutical compositions. When administered as separate pharmaceutical compositions, the compound or the present invention and taxol (or taxol analog) can be administered simultaneously or at different times, provided that the enhancing effect of the compound is retained.

The amount of compound and taxol (or taxol analog) administered to the subject will depend on the type and severity of the disease or condition and on the characteristics of the subject, such as general health, age, sex, body weight and tolerance to drugs. It will also depend on the degree, severity and type of cancer. The skilled artisan will be able to determine appropriate dosages depending on these and other factors. Effective dosages for taxol and taxol analog are well known and typically range from between about 1 mg/mm$^2$ per day and about 1000 mg/mm$^2$ per day, preferably between about 10 mg/mm$^2$ per day and about 500 mg/mm$^2$ per day. Effective amounts of a compound of the present invention typically range between about 1 mg/mm$^2$ per day and about 10 grams/mm$^2$ per day, and preferably between 10 mg/mm$^2$ per day and about 5 grams/mm$^2$.

The disclosed compounds are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds can also be administered orally (e.g., dietary), topically, by inhalation (e.g., intrabronchial, intranasal, oral inhalation or intranasal drops), or rectally, depending on the type of cancer to be treated. Oral or parenteral administration are preferred modes of administration. Suitable routes of administration of taxol and taxol analogs are well known in the art and include by parenteral administration, as described above for the compounds of the present invention. Suitable routes of administration for taxol and analogs thereof are well known and include inter alia parenteral and oral administration.

The disclosed compounds can be administered to the subject in conjunction with an acceptable pharmaceutical carrier as part of a pharmaceutical composition for treatment of cancer. Formulation of the compound to be administered will vary according to the route of administration selected (e.g., solution, emulsion, capsule). Suitable pharmaceutical carriers may contain inert ingredients which do not interact with the compound. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrasn) are known in the art (Baker, et al., "Controlled Release of Biological Active Agents", John Wiley and Sons, 1986). Suitable formulations for taxol and taxol analogs are well known in the art.

The disclosed compounds can be prepared according to methods described in Examples 1–12 and also according to methods described in the co-pending US Provisional Application entitled SYNTHESIS OF TAXOL ENHANCERS U.S. Provisional Application No. 60/304,318, filed Jul. 10, 2001. The entire teachings of this application are incorporated herein by reference.

The present invention is illustrated by the following examples, which are not intended to be limiting in any way.

EXEMPLIFICATION

Example 1

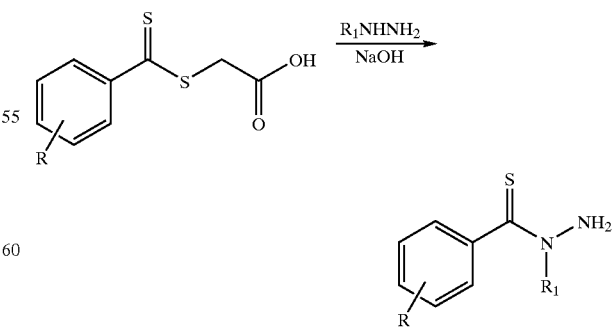

Preparation of Thiobenzoic acid N-methylhydrazide: Thiobenzoic acid N-methylhydrazide were prepared in 88% yield by slight modification of the prior art (Acta Chem.

Scand. 1961, 1087–1096); $^1$H NMR (CDCl$_3$) δ 3.3 (s, 3H), 6.0 (s, 2H), 7.3–7.4 (m, 5H); ESMS calcd (C$_8$H$_{10}$N$_2$S): 166.1; found: 167.1 (M+H)$^+$.

Example 2

Preparation of Thiobenzoic acid N-methylhydrazide: Bromobenzene (1.6 g, 10 mmol) was added into 25 ml anhydrous THF solution containing magnesium powder (0.3 g, 12.5 mmol), and refluxed for 2 hr. After it was cooled, the clear reaction solution was added into carbon disulfide (1 ml, 16.8 mmol) at 0° C., and stirred for 30 min at rt. The resulting mixture was then added into methylhydrazine (1.6 ml, 30 mmol) at 0° C., and stirred for another 2 hours. To this solution was added water (15 ml) and extracted with EtOAc (30 ml×3). The organic solution was concentrated to minimum volume, and subjected to silica gel column chromatography (eluant: 1:3–1:1 ethyl acetate: hexanes) to give thiobenzoic acid N-methyl hydrazide (0.72 g, total yield: 48%). $^1$H NMR (CDCl$_3$) δ 3.3 (s, 3H), 6.0 (s, 2H), 7.3–7.4 (m, 5H); ESMS calcd (C$_8$H$_{10}$N$_2$S): 166.1; found: 167.1 (M+H)$^+$.

Example 3

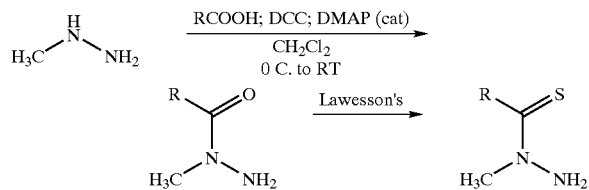

Preparation of 2,5-Dimethoxythiobenzoic acid N-methylhydrazine: DCC (4.5 g, 21.8 mmol) was added in one portion to a solution of 2,5-dimethoxybenzoic acid (3.6 g, 20 mol), methylhydrazine (1.2 ml, 23 mmol) and DMAP (30 mg, cat.) in CH$_2$Cl$_2$ (60 ml) cooled in an ice bath. The reaction mixture was stirred overnight at room temperature. The slurry was cooled at –20° C. for 1 h and filtered. The CH$_2$Cl$_2$ solution was evaporated and the residue was dried in vacuum. The resulting crude product was dissolved in toluene (50 ml). To this solution was added Lawesson's reagent (5.8 g, 14 mmol). The mixture was refluxed for 40 min, cooled to room temperature, and directly subjected to silica gel column chromatography (eluent: 25% to 35% ethyl acetate in hexanes) to give the 2,5-dimethoxythiobenzoic acid N-methylhydrazide (3.7 g, yield: 82%) as off-white solid. $^1$H NMR (300 MHz, CDCl$_3$): δ 6.88–6.80(m, 3H), 5.46 (s, 2H), 3.84(s, 3H), 3.82 (s, 3H), 3.28(s, 3H).

Example 4

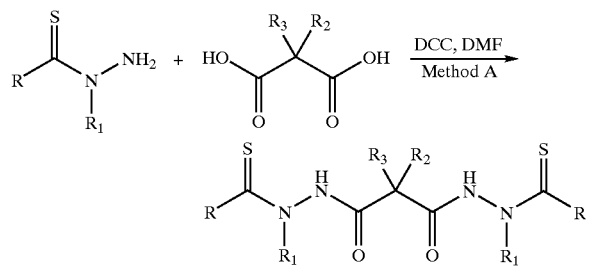

Preparation of N-Malonyl-bis[N'-methyl-N'-(thiobenzoyl) hydrazide]: To a stirred solution of thiobenzoic acid N-methylhydrazide (0.166 g, 10 mmol), HOBt.H$_2$O (0.15 g, 11 mmol) and malonic acid (0.052 g, 5 mmol) in DMF (2 mL) was added DCC (0.22 g, 10.7 mmol) at 0° C. The resultant suspension was stirred at 0° C. for 1 h and at room temperature for 3 h. Precipitated material was filtered off and washed with EtOAc (3×15 mL). Combined filtrate and washings was washed successively with H$_2$O (2×20 mL), 5% citric acid (20 mL), H$_2$O (20 mL), Saturated NaHCO$_3$ (20 mL) and brine (20 mL). After being dried over Na$_2$SO$_4$, the solvent was removed under reduced pressure to afford the crude product as a yellow solid, which was washed with warm EtOAc. 0.16 g (yield 80%) of pure product was obtained as a yellow powder. Rf 0.3 (Hexane/EtOAc 1:1 v/v); $^1$H NMR (CDCl$_3$) δ 3.1–3.8 (m, 6H), 3.4 (s, 2H), 7.1–7.45 (m, 10H), 9.5–10.5 (m, 1H) ppm; ESMS calcd (C$_{19}$H$_{20}$N$_4$O$_2$S$_2$): 400.1; found: 399.1 (M–H)$^+$.

Preparation of N-(2-Methylmalonyl-bis {N'-methyl-N'-[(2, 5-dimethoxy)thiobenzoyl]hhydrazide]:

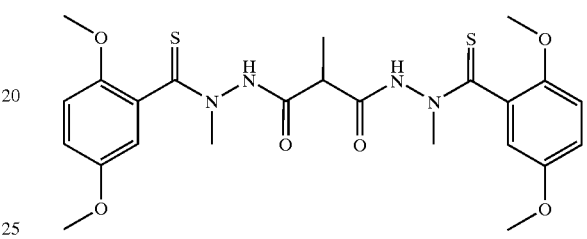

DCC (4 g, 19 mmol) was added to a solution of 2,5-dimethoxythiobenzoic acid N-methylhydrazide (3.7 g, 16.4 mmol) and 2-methylmalonic acid (2 g, 17 mmol) in DMF (20 ml) with stirring at 0° C. The reaction mixture was stirred for 1 h at room temperature. The slurry was cooled at –20° C. for 1 h and filtered. The filtrate was diluted with EtOAc (300 ml), washed with water (50 ml×3), dried with Na$_2$SO$_4$. The EtOAc solution was concentrated to minimum volume, and subjected to silica gel column chromatography (eluent: 1:4 to 2:1, ethyl acetate: hexanes) to give the title compound (3.5 g, 80%) as yellow powder. $^1$H NMR (CDCl$_3$) δ 10.12–9.14 (2H), 7.12–6.81 (m, 6H), 4.01–3.78 (m, 6H), 3.75–3.22(m, 6H), 2.82–2.62(m, 1H), 1.12–0.11 (m,3H); ESMS cacld (C$_{24}$H$_{30}$N$_4$O$_6$S$_2$):534.16; found: 535.1 (M+H).

Example 5

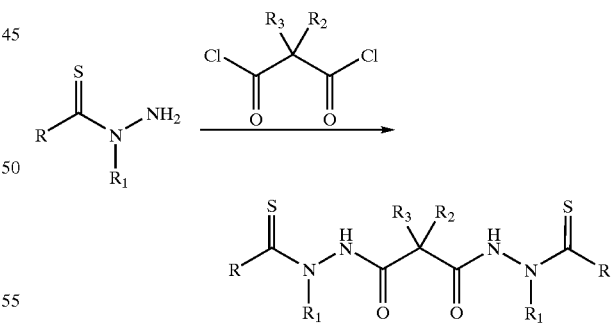

Preparation of N-Malonyl-bis[N'-methyl-N'-(thiobenzoyl) hydrazide]: To a solution of thiobenzoic acid N-methylhydrazine (10 g) stirred at 0 C were added subsequently triethylamine (8.5 mL) and malonyl dichloride (3.05 mL). The reaction mixture was stirred for 10 min, washed with water (3×50 mL), dried over sodium sulfate and concentrated. Purification by recrystallization from methylene dichloride (35 mL) gave the product as light yellow crystals (9.0 g, 75%) which was identical to the product obtained in Example 6.

Example 6

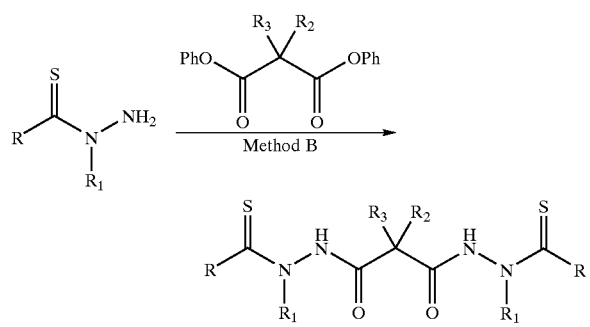

Preparation of N-Malonyl-bis[N'-methyl-N'-(thiobenzoyl) hydrazide]: A stirred solution of thiobenzoic acid N-methylhydrazide (1.66 g, 10 mmol) and diphenyl malonate (1.30 g, 5.08 mmol) in dry THF (100 mL) was heated to reflux for 72 h. Volatile components were then removed under reduced pressure. The crude product was purified by column chromatography on silica gel using a mixture of hexane and EtOAc as eluant (gradient from 4:1 v/v to 1:1 v/v). 1.07 g (51% yield) of pure product N-malonyl-bis[N'-methyl-N'-(thiobenzoyl)hydrazide] was obtained as a yellow powder. Physical property was identical to that obtained in Example 5.

Example 7

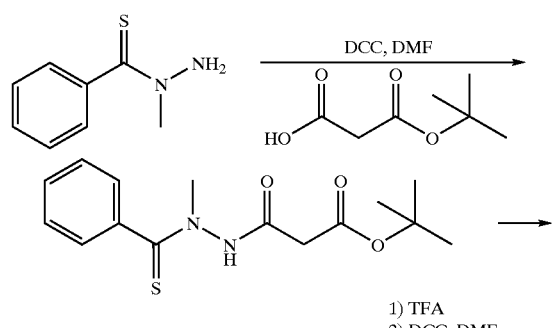

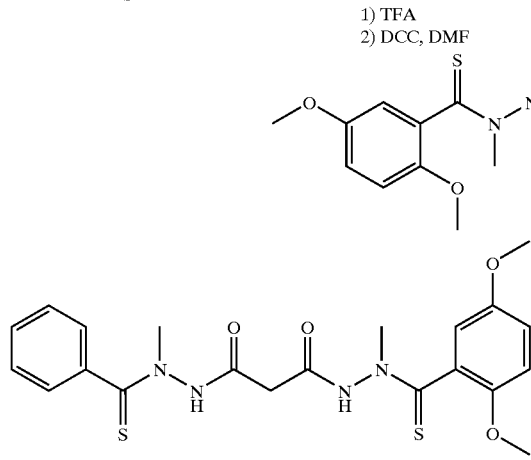

A slurry of thiobenzoic acid N-methylhydrazide (1.0 g, 6 mmol), mono-tert-butyl malonate (1.0 mL, 6 mmol), HOBt.H$_2$O (0.98 g, 7.2 mmol), and DCC (1.34 g, 6.5 mmol) in DMF (5 mL) was stirred at 0° C. for 3 h and then at room temperature for 3 h. Precipitated material was filtered off and washed with EtOAc (3×20 mL). Combined filtrate and washings was washed successively with H$_2$O (2×20 mL), 5% citric acid (20 mL), H$_2$O (20 mL), Saturated NaHCO$_3$ (20 mL) and brine (20 mL). After being dried over Na$_2$SO$_4$, the solvent was removed under reduced pressure to afford the crude product as a solid, which was washed with Et$_2$O. 0.94 g (yield 51%) of pure product N'-Methyl-N'-thiobenzoyl-hydrazinocarbonyl)-acetic acid tert-butyl ester was obtained as a yellow powder. $^1$H NMR (CDCl$_3$) δ 1.6–1.7 (ds, 9H), 3.1–4.1 (in, 5H), 7.3–7.7 (in, 5H), 9.7–10.3 (ds, 1H) ppm; ESMS calcd (C$_{15}$H$_{20}$N$_2$O$_3$S): 308; found: 307 (M−H)$^+$.

A solution of N'-methyl-N'-thiobenzoyl-hydrazinocarbonyl)-acetic acid tert-butyl ester (0.19 g, 0.6 mmol) and TFA (0.12 mL, 1.6 mmol) in dry DCM (10 mL) was stirred at 10° C.–15° C. for 12 h (reaction was monitored by TLC). Volatile components were removed under reduced pressure (bath temperature below 5° C.). After being dried in vacuo, DMF (3 mL) was added followed by the addition of DCC (0.13 g, 0.6 mmol), HOBt.H$_2$O (93 mg, 0.7 mmol) and thio-2,5-dimethoxybenzoic acid N-methylhydrazide (0.13 g, 0.57 mmol). The resultant solution was stirred at 0° C. for half an hour and then at room temperature for 3 h. Precipitated material was filtered off and washed with EtOAc (3×10 mL). Combined filtrate and washings was washed successively with H$_2$O (2×10 mL), 5% citric acid (10 mL), H$_2$O (10 mL), Saturated NaHCO$_3$ (20 mL) and brine (20 mL). After being dried over Na$_2$SO$_4$, the solvent was removed under reduced pressure to afford the crude product as an oil, which was purified by SGC (4:1 hexane/EA to 2:1 EtOAc/Hexane). 0.14 g (yield 53%) of pure product was obtained as a yellow powder. $^1$H NMR (CDCl$_3$) δ 3.1–3.9 (m, 18H), 6.7–7.4 (m,9H) ppm; ESMS calcd (C$_{21}$H$_{24}$N$_4$O$_4$S2): 460.1; found: 461.1 (M+H)$^+$.

Example 8

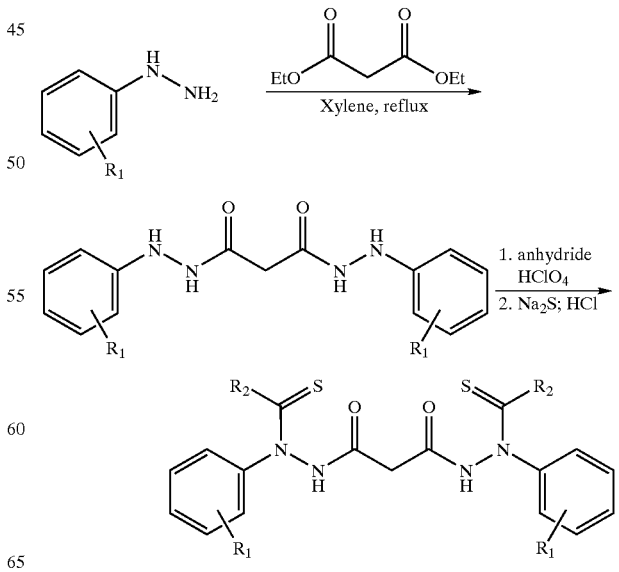

Preparation of N—N-malonyl-bis[N'-phenyl-N'-(thiobenzoyl)hydrazide]

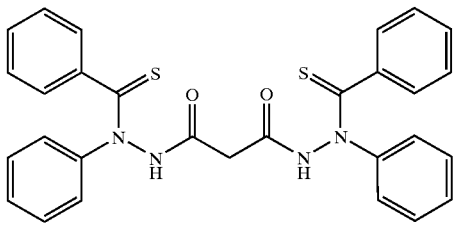

A mixture of phenylhydrazine (30 mL) and ethyl malonate (in xylene (150 mL) was heated to reflux overnight. The reaction was cooled to room temperature. The precipitates were collected via filtration and washed with ethanol to give N-malonyl-bis(N'-phenylhydrazide) as a white solid (14 g). The hydrazide (3.4 g) was suspended in benzoic anhydride (50 g) with warning. To it was added dropwise perchloric acid (57% in water, 3 mL). The reaction mixture turned to clear solution initially and then quickly solidified. After standing at room temperature for 1 h, ether (50 mL) was added. The resulting slurry was filtered and washed with ether (2×00 mL) to give the perchlorate salts as a white solid (5.7 g). The salts were taken into acetone and added as a slurry over 5 min to Na$_2$S (0.6 M in water, 90 mL) stirred at room temperature. After 30 min, the reaction was acidified with HCl(c) to afford a yellow slurry. The solid was collected via filtration and washed with water (20 mL) and ether (2×25 mL) to give N-malonyl-bis[N'-phenyl-N'-(thiobenzoyl)hydrazide] as an off-white solid (3.6 g). $^1$H NMR (CDCl$_3$): δ 7.2 (m, 20H); 3.5 (br s, 2H). MS calcd for C$_{29}$H$_{24}$N$_4$O$_2$S$_2$: 524.13: Found: 525.1 (M+H).

Example 9

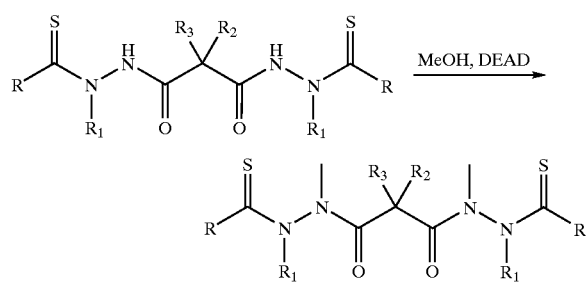

Preparation of N-Malonyl-bisrN-methyl-N'-phenyl-N'-(thiobenzoyl)hydrazide]

To a stirred solution of N-malonyl-bis[N'-phenyl-N'-(thiobenzoyl)hydrazide] (180 mg, 0.34 mmol), MeOH (22 uL) and triphenylphosphine (200 mg, 0.64 mmol) in dry THF(10 mL) was added a solution of DEAD (0.12 mL) in THF (3 mL) dropwise. The resultant orange solution was stirred at room temperature for 12 h. After removal of the volatile components, the crude product was purified by SGC (3:1 Hexane/EtOAc) to afford 98 mg (52% yield) of the title compound as syrup. $^1$H NMR (CDCl$_3$) δ 3.3–4.5 (m, 8H), 7.1–7.8 (m, 20H) ppm; ESMS calcd (C$_{31}$H$_{28}$N$_4$O$_2$S$_2$): 552; found: 551 (M–H)$^+$.

Example 10

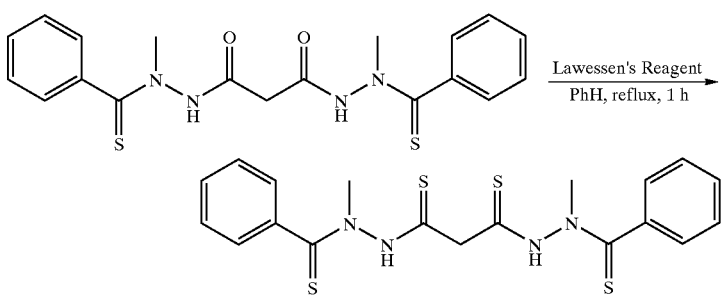

A stirred mixture of N-malonyl-bis[N'-phenyl-N'-(thioacetyl)hydrazide) starting material (0.1 g, 0.25 mmol) and Lawesson's reagent (0.15 g, 0.37 mmol) in dry benzene (20 mL) was heated to reflux for 1 h. After being cooled to room temperature, the mixture was 25 filtered through a layer of silica gel, washed with THF (2×15 mL). The filtrate and washings were combined and concentrated under reduced pressure. Flush column chromatography on silica gel (hexane to 4:1 hexane/EtOAc to 2:1 hexane/EtOAc) afforded N-bisthiomalonyl-bis[N'-phenyl-N'-(thioacetyl) hydrazide as a clear syrup (16 mg, 15%). $^1$H NMR (CDCl$_3$) δ 3.80–3.95 (m, 8H), 7.02–7.30 9m, 10H). ESMS calcd (C$_{19}$H$_{20}$N$_4$S$_4$): 432.06; found: 433.0 (M+H)$^+$.

Example 11

The compounds shown below were prepared by the procedures described above. Analytical data is provided for these compounds.

$^1$H NMR (CDCl$_3$) δ 3.1–3.8 (m, 6H), 3.4 (s, 2H), 7.1–7.45 (m, 10H), 9.5–10.5 (m, 1H) ppm; ESMS calcd (C$_{19}$H$_{20}$N$_4$O$_2$S$_2$): 400.1; found: 399.1 (M–H)$^+$.

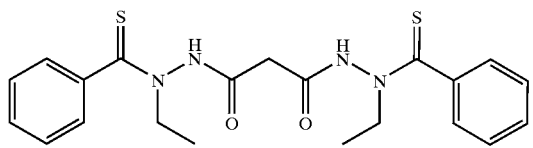

$^1$H NMR (CDCl$_3$) δ 1.0–1.35 (m, 6H), 3.0–4.3 (m, 6H), 7.05–7.40 (m, 10H), 9.1–10.1 (m, 2H); ESMS cacld (C$_{21}$H$_{24}$N$_4$O$_2$S$_2$): 428.8; found: 427 (M–H)$^+$. Anal Calc For C$_{21}$H$_{24}$N$_4$O$_2$S$_2$ (428.13) C, 58.85; H, 5.64; N, 13.07; S, 14.96. Found: C, 58.73; H, 5.62; N, 12.97; S, 14.96.

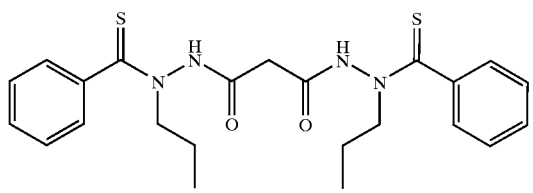

$^1$H NMR (CDCl$_3$) δ 0.7–1.0 (m, 6H), 1.4–1.9 (m, 4H), 3.1–4.2 (m, 6H), 7.1–7.4 (m, 10H), 8.9–10.2 (m, 2H) ppm; ESMS (C$_{23}$H$_{28}$N$_4$O$_2$S$_2$): 456.1; found: 455.1 (M–H)$^+$.

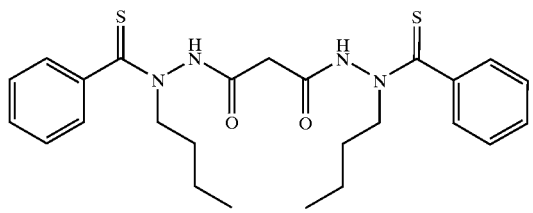

mp 141–143° C.; $^1$H NMR (CDCl$_3$) δ 0.6–1.05 (m, 6H), 1.1–1.9 (m, 8H), 3.0–4.2 (m, 6H), 7.0–7.35 (m, 10H), 8.9–11 (ms, 2H). ESMS (C$_{25}$H$_{32}$N$_4$O$_2$S$_2$): 484.2; found: 483.1 (M–H)$^+$. Anal Calc For C$_{25}$H$_{32}$N$_4$O$_2$S$_2$ (484.2) C, 61.95; H, 6.65; N, 11.56; S, 13.23. Found: C, 61.98; H, 6.52; N, 11.26; S, 13.16.

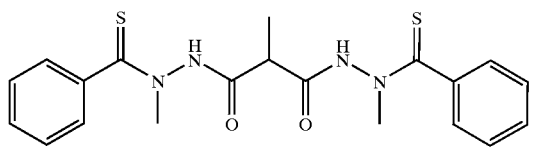

$^1$H NMR (DMSO-d$_6$) δ 0.4–0.9 (dd, 3H, J=7), 2.7 (q, 1H), 3.1–3.6 (m, 6H), 7.1–7.5 (m, 110H), 10.9 (br, 2H) ppm; ESMS (C$_{20}$H$_{22}$N$_4$O$_2$S$_2$): 414; found: 413 (M–H)$^+$.

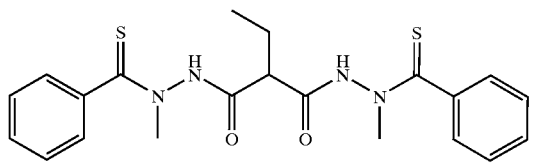

$^1$H NMR (CDCl$_3$) δ 0.5 (t, 3H, J=7), 1.1–1.6 (m, 2H), 2.7 (t, 11H, J=7), 3.1–3.3 (m, 6H), 7.0–7.3 (m, 10H), 10.25 (s, 2H) ppm; MS (C$_{21}$H$_{24}$N$_4$O$_2$S$_2$): 428.1; found: 427.1 (M–H)$^+$.

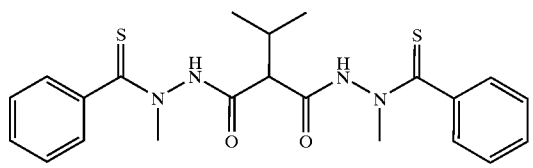

$^1$H NMR (CDCl$_3$) δ 0.5 (d, 6H, J=7), 0.9–1.2 (m, 1H), 3.0–41 (m, 7H), 7.1–7.4(m, 10H), 10.3 (s, 2H) ppm; ESMS (C$_{22}$H$_{26}$N$_4$O$_2$S$_2$): 442.1; found: 441.1 (M–H)$^+$.

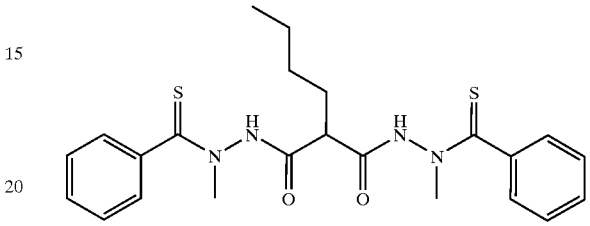

$^1$H NMR (CDCl$_3$) δ 0.4–1.3 (m, 5H), 1.5–1.8 (m, 2H), 3.0–3.7 (m, 6H), 7.1–7.5 (m, 10H), 11 (s, 2H) ppm; ESMS (C$_{23}$H$_{28}$N$_4$O$_2$S$_2$): 456.1; found: 455.1 (M–H)$^+$.

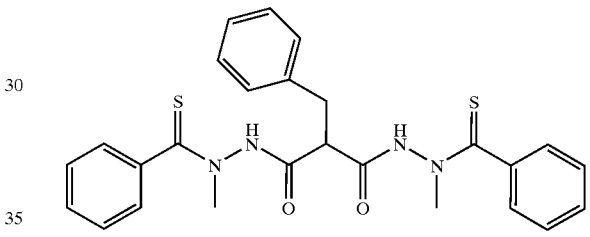

$^1$H NMR (CDCl$_3$) δ 2.1 (d, 2H, J=7), 2.9 (t, 1H, J=7), 3.1–3.5 (m, 6H), 6.8–7.4 (m, 15H), 11 (s, 2H) ppm; ESMS (C$_{26}$H$_{26}$N$_4$O$_2$S$_2$): 490.1; found: 489.1 (M–H)$^+$.

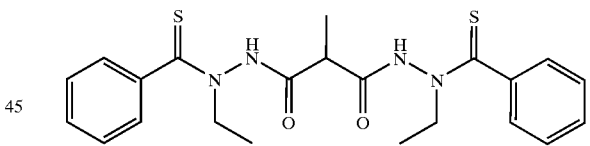

$^1$HNMR (CDCl$_3$) δ 0.4 (d, 3H, J=7), 1.0–1.4 (m, 6H), 2.75 (q, 1H), 3.0–4.3 (m, 4H), 7.1–7.4 (m, 10H), 10.6 (s, 2H); ESMS Calc For (C$_{22}$H$_{26}$N$_4$O$_2$S$_2$): 442.1; found: 441.1 (M–H)$^+$; Anal Calc For C$_{22}$H$_{26}$N$_4$O$_2$S$_2$ (442.15) C, 59.70; H, 5.92; N, 12.66; S, 14.49. Found: C, 59.64; H, 5.92; N, 12.59; S, 14.47.

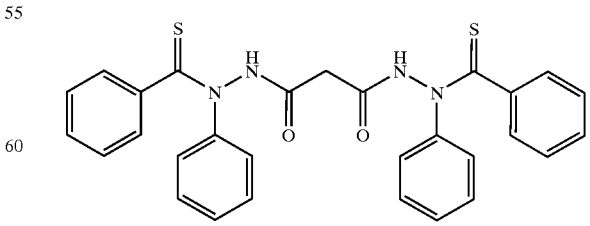

$^1$H NMR (DMSO-d$_6$) δ 3.20 (br, 2H), 7.1–7.6 (m, 20H), 11.5 (s, 2H) ppm; ESMS calcd (C$_{29}$H$_{24}$N$_4$O$_2$S2): 524.1; found: 523.1 (M–H)$^+$.

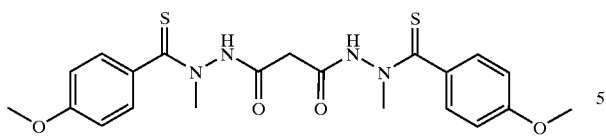

¹H NMR (CDCl₃) δ 3.0–4.3 (m, 14H), 6.6–7.5 (m, 8H), 10.4 (s, 2H) ppm; ESMS calcd (C₂₁H₂₄N₄O₂S₂): 460.2; found: 461.2 (M+H)⁺.

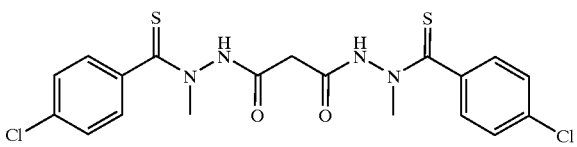

¹H NMR (CDCl₃) δ 2.65–3.60 (m, 8H), 7.2–7.4 (m, 8H), 11.1 (br, 2H); ESMS calcd (C₁₉H₁₈Cl₂N₄O₂S₂): 468.0; found: 467.9 (M–H)⁺.

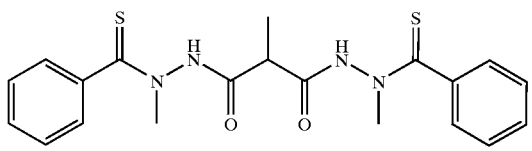

¹H NMR (CDCl₃) δ 0.4 (d, 3H, J=7), 2.7 (q, 1H, J=7), 3.0–3.8 (m, 6H), 7.2–8.2 (m, 8H), 10.5–10.7 (ms, 2H) ppm; ESMS calcd (C₂₀H₂₀Cl₂N₄O₂S₂): 482.0; found: 481.0 (M–H)⁺.

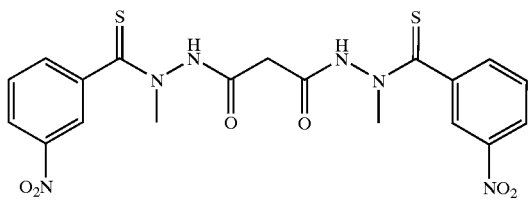

¹H NMR (CDCl₃) δ 2.9–3.8 (m, 6H), 7.3–7.7 (m, 4H), 8.0–8.3 (m, 4H), 10.9 (s, 2H); ESMS calcd (C₁₉H₁₈N₆O₆S₂): 490.0; found: 489.0 (M–H)⁺.

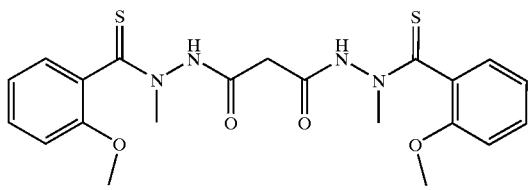

¹H NMR (CDCl₃) δ 3.1–3.9 (m, 14H), 6.7–7.8 (m, 8H), 9.0–10 (m, 2H) ppm; ESMS calcd (C₂₁H₂₄N₄O₄S₂): 460.1; found: 459.1 (M–H)⁺.

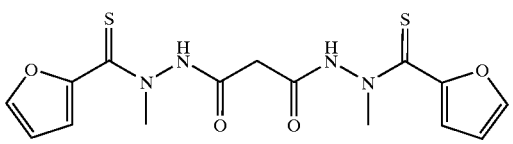

(SBR-11-5032): ¹H NMR (CDCl₃) δ 3.0–3.9 (m, 14H), 6.7–7.3 (m, 8H), 9.0–10 (m, 2H) ppm; ESMS calcd (C₂₁H₂₄N₄O₄S₂): 460.1; found: 459.1 (M–H)⁺.

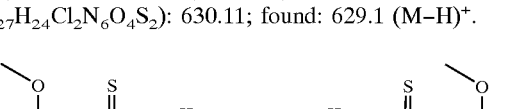

¹H NMR (acetone-d₆) δ 3.5 (s, 2H), 6.45 (d, 2H, J=5), 6.9 (d, 2H, J=5), 7.2–7.6 (m, 12H), 10.6 (s, 2H) ppm; ESMS calcd (C₂₅H₂₀N₄O₄S₂): 504.1; found: 503.1 (M–H)⁺.

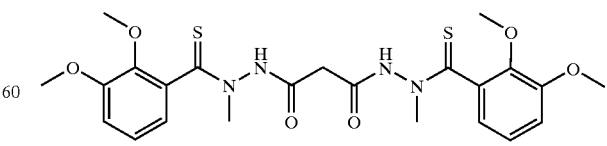

¹H NMR (DMSO-d₆) δ 2.60 (s, 6H), 3.05 (s, 6H), 3.40 (s, 2H), 7.15–7.50 (m, 8H) ppm; ESMS calcd (C₂₇H₂₄Cl₂N₆O₄S₂): 630.11; found: 629.1 (M–H)⁺.

¹H NMR (CDCl₃) δ 10.06–8.82 (2H), 7.16–6.81(m,6H), 4.01–3.81(m, 6H), 3.78–3.11(m,6H), 2.81–2.58(m,2H): ESMS cacld (C₂₃H₂₈N₄O₆S₂): 520.15; found: 521 (M+H).

¹H NMR (CDCl₃) δ 10.38–9.01 (2H), 7.12–6.82 (m, 6H), 3.92–3.78(m, 12H), 3.75–3.06(m, 6H), 2.61–2.51 (m, 2H); ESMS cacld (C₂₃H₂₈N₄O₆S₂): 520.15; found: 521 (M+H).

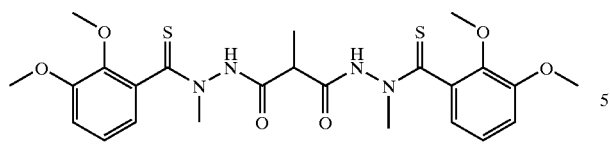

¹H NMR (CDCl₃) δ 9.45–8.63 (2H), 7.18–6.81 (m, 6H), 4.01–3.80(m, 6H), 3.78–3.24(m, 6H), 2.62–2.50(m, 1H), 1.74–0.11 (m, 3H); ESMS cacld (C₂₄H₃₀N₄O₆S₂):534.16; found: 535 (M+H).

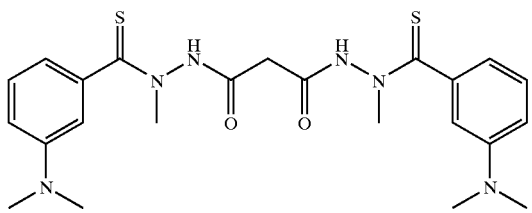

¹H NMR (CDCl₃) δ 10.19–8.61 (2H), 7.26–6.52(m, 6H), 3.81–3.08(m, 8H), 3.01–2.88(m, 12H). ESMS cacld (C₂₃H₃₀N₆O₂S₂): 486.19; found: 487 (M+H).

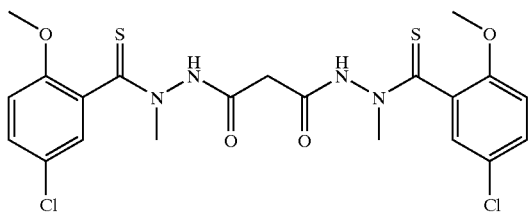

¹H NMR (CDCl₃) δ 9.92–8.80 (2H), 7.41–6.72 (m, 6H), 4.01–3.81(m,6H), 3.80–3.15 (m,6H), 2.76–2.42(m, 2H); ESMS cacld (C₂₁H₂₂Cl₂N₄O₄S₂):528.05; found: 529(M+H).

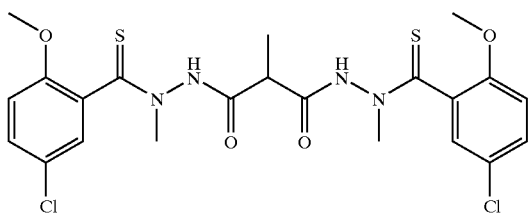

¹H NMR (CDCl₃) δ 10.21–9.02(2H), 7.60–6.81 (m, 6H), 4.14–3.88(m, 6H), 3.87–3.18 (m,6H), 2.84–2.65(m, 1H), 1.10–0.16 (m, 3H); ESMS cacld (C₂₂H₂₄Cl₂N₄O₄S₂): 542.06; found: 543(M+H).

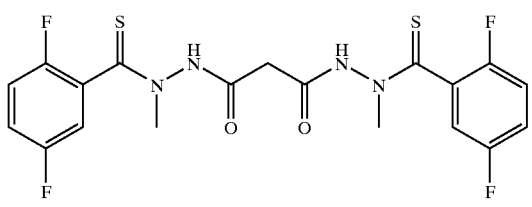

¹H NMR (CDCl₃) δ 10.02–9.20 (2H), 7.63–7.01 (m, 6H), 4.21–3.22(m, 6H), 1.88–1.36 (m, 2H); ESMS cacld (C₁₉H₁₆F₄N₄O₂S₂): 472.07; found: 473 (M+H).

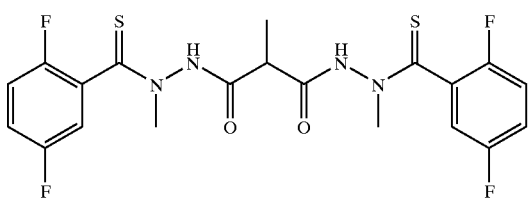

¹H NMR (CDCl₃) δ 7.93–7.61 (2H), 7.40–6.92 (m, 6H), 3.98–3.41 (m, 6H), 2.19–0.93 (m, 4H); ESMS cacld (C₂₀H₁₈F₄N₄O₂S₂): 486.08; found: 487 (M+H).

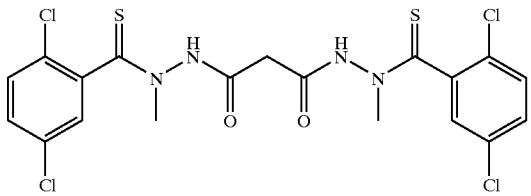

¹H NMR (CDCl₃) δ 10.12–9.21(2H), 7.67–7.23 (m, 6H), 3.94–3.22 (m, 6H), 2.01–1.21 (m, 2H); ESMS cacld (C₁₉H₁₆Cl₄N₄O₂S2): 535.95; found: 537(M+H).

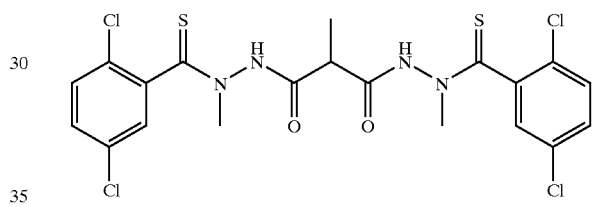

¹H NMR (CDCl₃) δ 7.78–7.23 (2H), 4.56–3.10 (m, 6H), 2.34–1.12 (m, 4H); ESMS cacld (C₂₀H₁₈Cl₄N₄O₂S₂): 549.96; found: 551 (M+H).

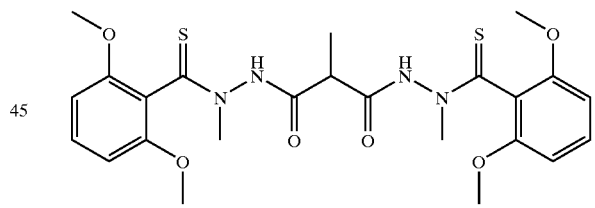

¹H NMR (CDCl₃) δ 9.92–9.01 (2H), 7.38–7.15 (m,3H), 6.66–6.51 (m,3H), 3.98–3.75 (m,12H), 3.72–3.21(m,6H), 2.01–0.42 (m, 4H); ESMS cacld (C₂₄H₃₀N₄O₆S₂):534.16; found: 535 (M+H).

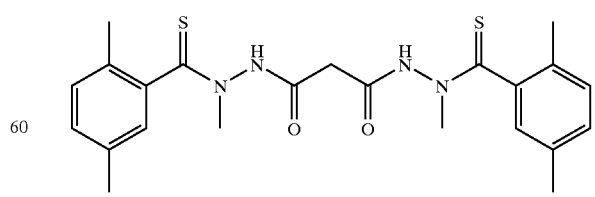

¹H NMR (CDCl₃) δ 10.51–9.82 (2H), 7.42–6.80 (m, 6H), 3.92–3.04(m, 6H), 2.60–1.21 (m, 14H); ESMS cacld (C₂₃H₂₈N₄O₂S₂): 456.17; found: 457(M+H).

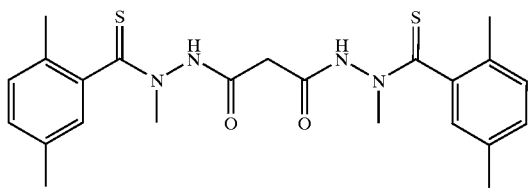

¹H NMR (CDCl₃) δ 10.51–8.82 (2H), 7.11–6.89 (m, 6H), 3.81–3.02 (m, 6H), 2.40–1.02 (m, 16H); ESMS cacld ($C_{24}H_{30}N_4O_2S_2$): 470.18; found: 471(M+H).

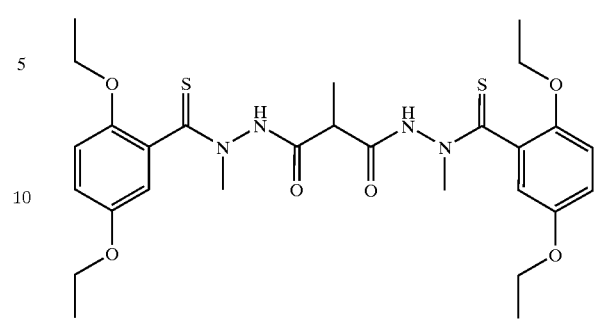

¹H NMR (CDCl₃) δ 9.81–8.79 (2H), 7.01–6.64 (m, 6H), 4.21–3.81(m, 8H), 3.80–3.22 (m, 6H), 1.54–1.20 (m, 13H), 1.01–0.16 (m, 3H); ESMS cacld ($C_{28}H_{38}N_4O_6S_2$): 590.22; found: 591(M+H).

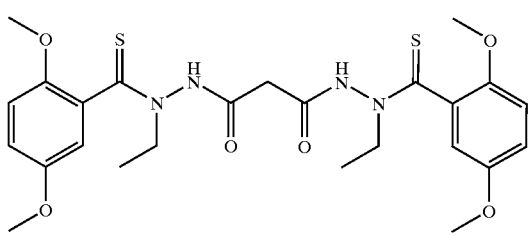

¹H NMR (CDCl₃) δ 9.86–8.42 (2H), 7.01–6.6 (m, 6H), 4.18–3.51 (m, 16H), 3.22–2.26 (2H), 1.40–1.04 (m, 6H); ESMS cacld ($C_{25}H_{32}N_4O_6S_2$):548.18; found: 547 (M–H).

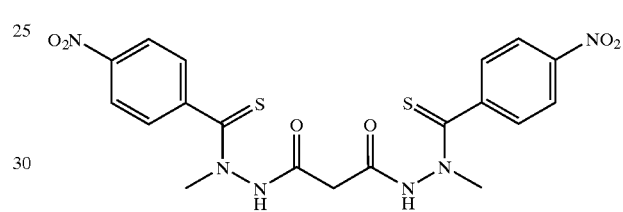

¹H NMR (DMSO-d₆): δ 8.25 (d, J=8.1 Hz, 4H), 7.50 (d, J=8.1 Hz, 4H), 3.7–3.3 (m, 8H); ESMS cacld for $C_{19}H_{18}N_6O_6S_2$: 490.1; Found: 489.0 (M–H).

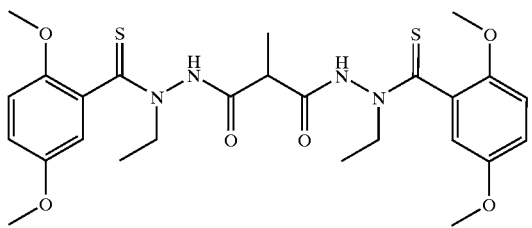

¹H NMR (CDCl₃) δ 9.99–8.41 (2H), 7.01–6.68 (m, 6H), 4.18–3.56 (m, 16H), 1.40–0.02 (m, 10H); ESMS cacld ($C_{26}H_{34}N_4O_6S_2$): 562.19; found: 561(M–H).

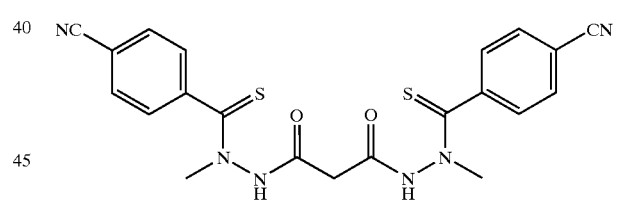

¹H NMR (CDCl₃): δ 10.25 (m, 2H), 7.7–7.4 (m, 8H), 3.7 (m, 2H), 3.35 (m, 6H); ESMS cacld for $C_{21}H_{18}N_6O_2S_2$: 450.1; Found: 449.0 (M–H).

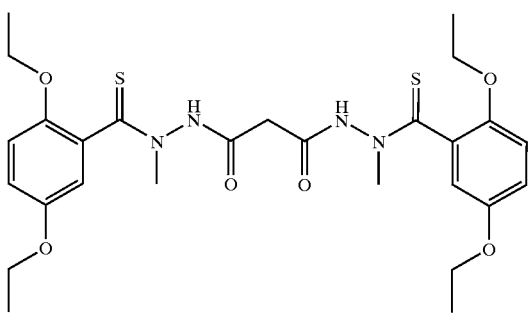

¹H NMR (CDCl₃) δ 10.12–8.82 (2H), 7.03–6.62 (m, 6H), 4.21–3.87 (m, 8H), 3.84–3.01(m, 6H), 2.71–2.42 (m, 2H), 1.56–1.21 (m, 12H); ESMS cacld ($C_{27}H_{36}N_4O_6S_2$): 576.21; found: 577(M+H).

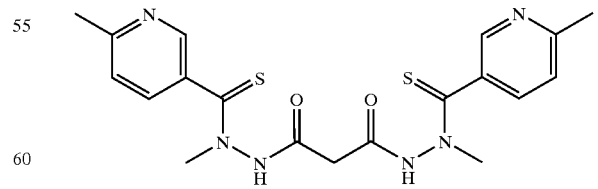

¹H NMR (CDCl₃): δ 8.2 (s, 2H), 7.7–7.5 (m, 4H), 3.7–3.4 (m, 8H), 2.9–2.8 (m, 6H); ESMS cacld for $C_{19}H_{22}N_6O_2S_2$: 430.1; Found: 431.1 (M+H).

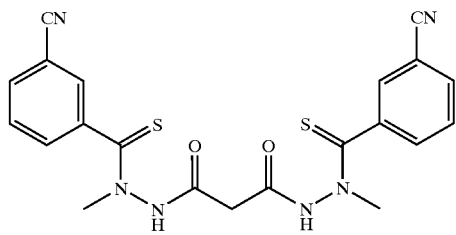

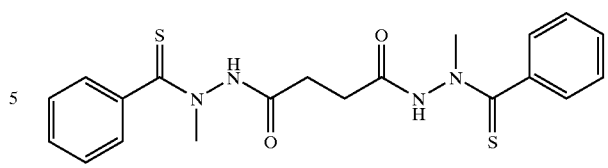

¹H NMR (CHCl₃) δ 9.48–8.55 (2H), 7.56–7.20(m, 10H), 3.80–3.31(m, 6H), 2.88–2.22(m, 4H). ESMS cacld (C₂₀H₂₂N₄O₂S₂): 414.12; found: 415.1 (M+H).

¹H NMR (CDCl₃): δ 10.0–9.2 (m, 2H), 7.9–7.45 (m, 8H), 4.0–3.4 (m, 8H); ESMS cacld for C₂₁H₁₈N₆O₂S₂: 450.1; Found: 451.0 (M+H).

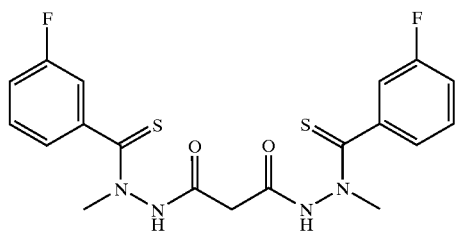

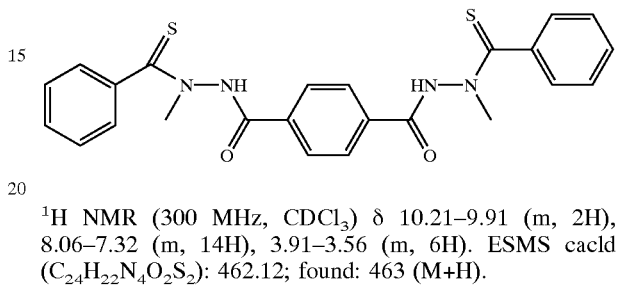

¹H NMR (300 MHz, CDCl₃) δ 10.21–9.91 (m, 2H), 8.06–7.32 (m, 14H), 3.91–3.56 (m, 6H). ESMS cacld (C₂₄H₂₂N₄O₂S₂): 462.12; found: 463 (M+H).

¹H NMR (CDCl₃): δ 10.1–9.4 (2H), 7.5–7.2 (m, 8H), 3.9–3.3 (m, 8H); ESMS cacld for C₁₉H₁₈F₂N₄O₂S₂: 436.1; Found: 437.1 (M+H1).

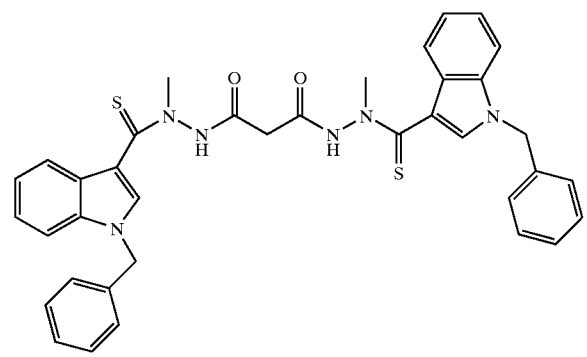

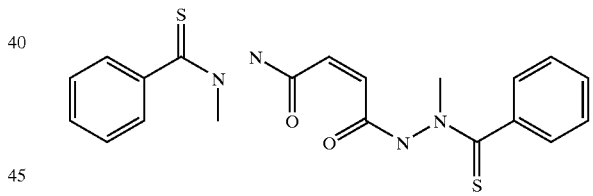

¹H NMR (300 MHz, DMSO-d₆) δ 11.60–11.40 (m, 2H), 7.48–6.46 (m, 12H), 3.64–3.3.30(m, 6H). ESMS cacld (C₂₀H₂₀N₄O₂S₂): 412.10; found: 413 (M+H).

¹H NMR (CDCl₃): δ 3.3 (s, 2H), 3.6 (s, 6H), 5.25 (s, 4H), 7.05–7.3 (m, 16H), 7.6 (s, 2H), 7.9 (d, 2H, J=6), 10.56 (s, 2H) ppm; ESMS calcd (C₃₇H₃₄N₆O₂S₂): 658.2; found: 659.2 (M+H)⁺.

¹H NMR (300 MHz, CDCl₃) δ 7.58–7.20 (m, 12H), 3.68–3.20 (m, 6H). ESMS cacld (C₂₀H₂₀N₄O₂S₂): 412.10; found: 413 (M+H).

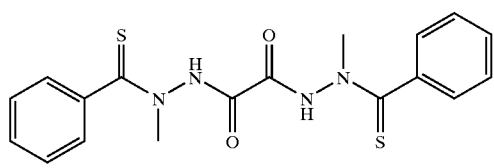

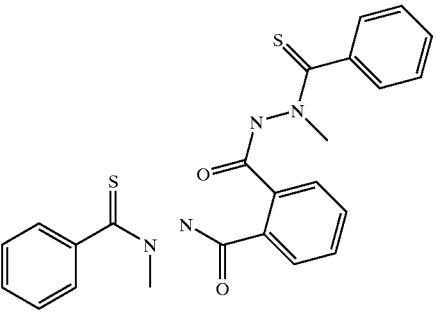

¹HNMR (DMSO) δ 11.98 (2H), 7.44–7.12 (m, 10H), 3.69–3.14(s, 6H). ESMS cacld (C₁₈H₁₈N₄O₂S₂): 386.09: found: 387.1 (M+H).

¹H NMR (300 MHz, CDCl₃): δ 9.65–8.70 (2H), 8.01–7.21 (m, 14H), 3.84–3.40(m, 6H). ESMS cacld (C₂₄H₂₂N₄O₂S₂): 462.12: found: 463 (M+H).

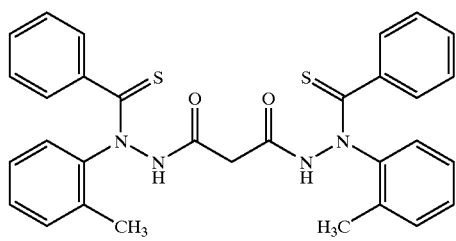

¹H NMR (CDCl₃): δ 7.2 (m, 18H); 3.5 (br s, 2H); 2.4 (br s, 6H). MS calcd for $C_{31}H_{28}N_4O_2S_2$: 552.2: Found: 553.2 (M+H).

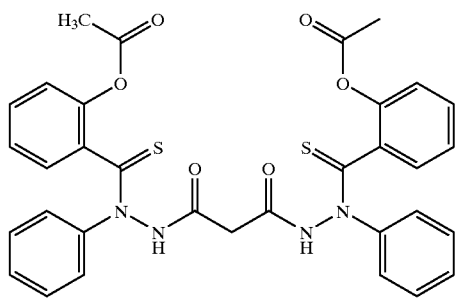

¹H NMR (CDCl₃): δ 7.5 (br s, 18H), 3.4 (br s, 2H), 2.45 (s, 6H). ESMS cacld for $C_{33}H_{28}N_4O_6S_2$: 640.1; Found 641.1 (M+H).

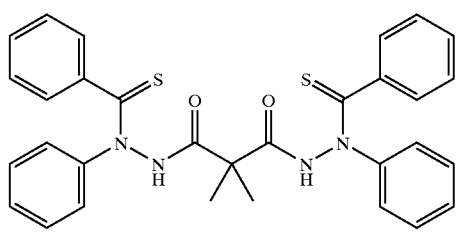

¹H NMR (CDCl₃-D₂O): δ 7.45–7.15 (m, 20H), 1.6 (br s, 6H). ESMS cacld for $C_{31}H_{28}N_4O_2S_2$: 552.2; Found: 553.2 (M+H).

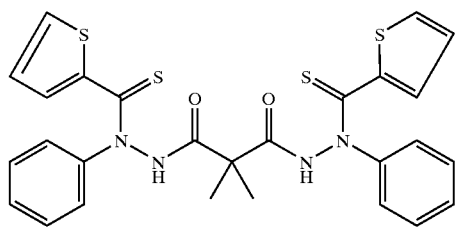

¹H NMR (DMSO-d₆): δ 11.3 (s, 2H), 7.75 (d, J=6.0 Hz, 2H), 7.5–7.4 (m, 12H); 6.9 (m, 2H); ESMS cacld for $C_{27}H_{24}N_4O_2S_4$: 564.1; Found: 565.2 (M+H).

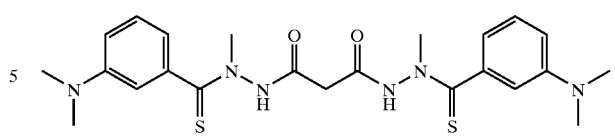

¹H NMR (300 MHz, CDCl₃): δ 10.18–8.60 (m, 2H), 7.26–6.46 (m, 8H), 3.80–3.02(m, 6H), 3.00–2.80(m, 12H). 1.78–1.56(m, 2H). ESMS cacld($C_{23}H_{30}N_4O_2S_2$):486.19; found: 487 (M+H).

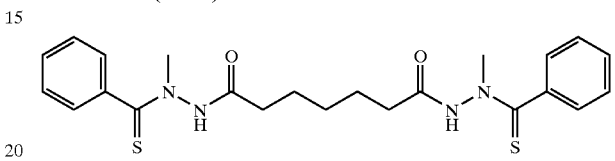

¹H NMR (300 MHz, DMSO): δ 10.90–10.81 (m, 2H), 7.50–7.21 (m, 10H), 3.78–3.36(m, 6H), 2.64–0.50(m, 10H). ESMS cacld($C_{20}H_{28}N_4O_2S_2$): 456.17; found: 457 (M+H).

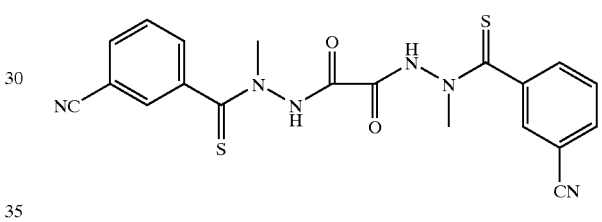

¹H NMR (300 MHz, CDCl₃): δ 10.00–9.71 (m, 2H), 7.72–7.21(m, 8H), 3.80–3.26(m, 6H). ESMS cacld ($C_{20}H_{16}N_6O_2S_2$):436.08; found: 437 (M+H).

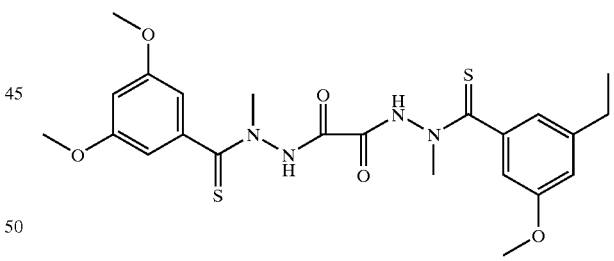

¹H NMR (300 MHz, CDCl₃): δ 10.60–9.41 (m, 2H), 7.15–6.23(m, 6H), 3.89–3.28(m, 6H), 3.76(S, 12H). ESMS cacld($C_{22}H_{28}N_4O_6S_2$):506.13; found:507 (M+H).

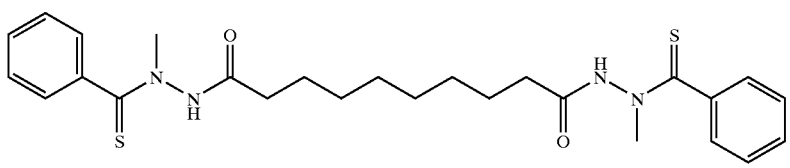

$^1$H NMR (300 MHz, DMSO): δ 7.40–7.12 (m, 10H), 3.70–2.80(m, 6H), 1.84–0.72(m, 16H). ESMS cacld (C$_{26}$H$_{34}$N$_4$O$_2$S$_2$):498.21; found: 499 (M+H).

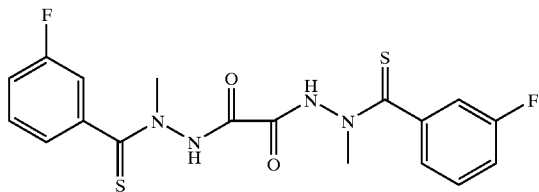

$^1$H NMR (300 MHz, CDCl$_3$): δ 10.42–9.53 (m, 2H), 7.55–6.87(m, 8H), 3.99–3.28(m, 6H), ESMS cacld (C$_{18}$H$_{10}$N$_4$F$_2$O$_2$S$_2$): 422.07; found: 423 (M+H).

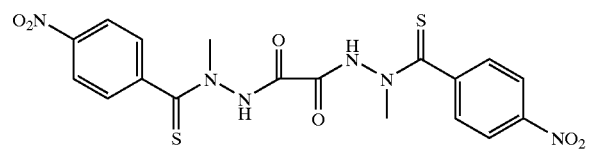

$^1$H NMR (300 MHz, DMSO): δ 12.08 (br. 2H), 8.27–7.24 (m, 8H), 3.70–3.15(m, 6H). ESMS cacld(C$_{18}$H$_{16}$N$_6$O$_6$S$_2$) :476.06; found: 477 (M+H).

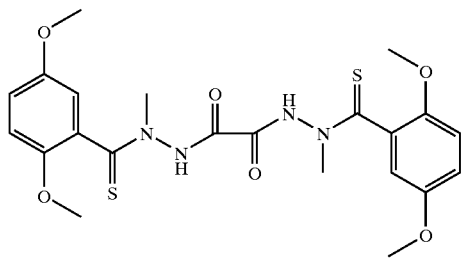

$^1$H NMR (300 MHz, CDCl$_3$): δ 10.12–9.83 (m, 2H), 7.15–6.63(m, 6H), 3.99–2.91(m, 6H), ESMS cacld (C$_{22}$H$_{26}$N$_4$O$_6$S$_2$):506.13; found: 507 (M+H).

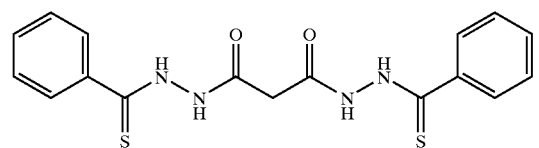

$^1$H NMR (300 MHz, DMSO): δ 11.12–10.54 (m, 2H), 8.27–7.18 (m, 10H), 4.26–3.72(m, 2H), 3.37–3.18(m, 2H). ESMS cacld(C$_{17}$H$_{16}$N$_4$O$_2$S$_2$):372.07; found: 371 (M-H).

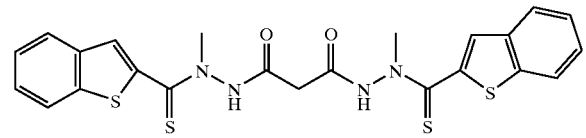

$^1$H NMR (300 MHz, DMSO): δ 11.52 (br, 2H), 7.95–7.33 (m, 10H), 3.42–3.22(m, 6H), 2.48(m, 2H). ESMS cacld (C$_{23}$H$_{20}$N$_4$O$_2$S$_4$):512.05; found: 513 (M+H).

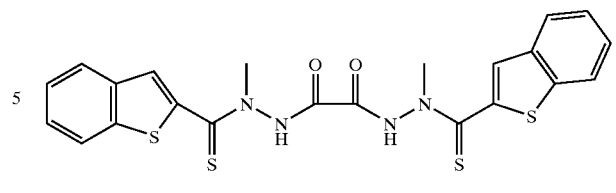

$^1$H NMR (300 MHz, CDCl$_3$): δ 7.81–7.28(m, 8H), 3.82(s, 6H). ESMS cacld(C$_{22}$H$_{18}$N$_4$O$_2$S$_4$):498.03; found: 499 (M+H).

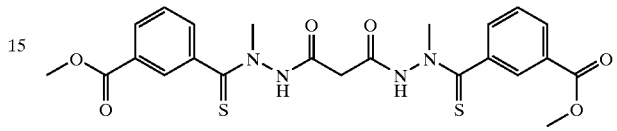

$^1$H NMR (300 MHz, CDCl$_3$): δ 10.02–9.11 (m, 2H), 8.16–7.28(m, 8H), 3.99–3.08(m, 6H), 2.90–1.20(m, 2H). ESMS cacld(C$_{23}$H$_{24}$N$_4$O$_6$S$_2$):516.11; found: 517 (M+H).

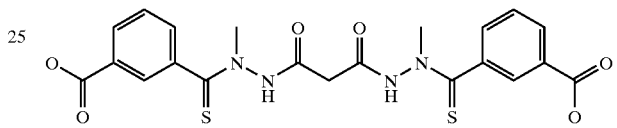

$^1$H NMR (300 MHz, DMSO) δ 7.99 (m, 8H), 8.16–7.28(m, 8H), 3.80–3.14(m, 6H), 1.80–1.21(m, 2H). ESMS cacld (C$_{21}$H$_{20}$N$_4$O$_6$S$_2$):488.08; found: 487 (M-H).

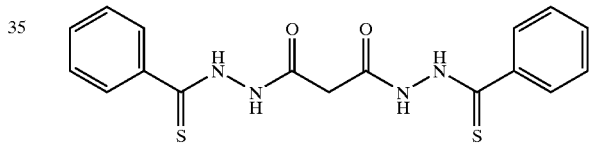

$^1$H NMR (300 MHz, CDCl$_3$): δ 10.82–10.55 (m, 2H), 7.91–7.29(m, 10H), 3.64–3.11(m, 6H), 1.90–1.40(m, 2H). ESMS cacld(C$_{19}$H$_{20}$N$_4$O$_2$S$_2$):400.19; found: 399 (M-H).

Example 12

Compound (1) Enhances the Anti-Cancer Activity of Paclitaxel in vivo General Procedure of in vivo Anti-Tumor Study The in vivo anti-cancer enhancing effect of novel compounds was assessed in tumor bearing mice using the tumor growth inhibition assay. Tumor cells were implanted by injection of a tumor cell suspension subcutaneously in the flank of a mouse. Treatment of the tumor with an experimental compound and Paclitaxel begun after the tumor had been established (volume was about 100 mm$^3$). Animal then begun a multiple injection schedule where the compound and Paclitaxel were given by IV route of administration. Tumors were measured two times a week. During the course of this assay, animals were monitored daily for signs of toxicity including body weight loss.

Procedure

A supplemented media was prepared from 50% DMEM/ Dulbecco Modified Eagle Medium (High Glucose), 50% RPMI 1640, 10% FBS/Fetal Bovine Serum (Hybridoma Tested; Sterile Filtered), 1% L-Glutamine, 1% Penicillin-Streptomycin, 1% MEM Sodium Pyruvate and 1% MEM Non-Essential Amino Acids. FBS was obtained from Sigma Chemical Co. and other ingredients were obtained from Invitrogen Life Technologies, USA). The supplemental Media was warmed to 37° C. and 50 ml of media was added to a 175 cm tissue culture flask.

The cells used in the assay were MDA-435 Human Breast Carcinoma from the American Type Culture Collection. 1 vial of MDA-435 cells from the liquid nitrogen frozen cell stock was removed. The frozen vial of cells was immediately placed into a 37° C. water bath and gently swirled until thawed. The freeze-vial was wiped with 70% ethanol and cells were immediately pipetted into the 175 cm$^2$ tissue culture flask containing supplemented media. The cells were incubated overnight and the media was removed and replaced with fresh supplemented media the next day. The flask was incubated until flask became about 90% confluent. This took anywhere from 5–7 days.

The flask was washed with 10 ml of sterile room temperature phosphate buffered saline (PBS). The cells were trypsinized by adding 5 ml of warmed Trypsin-EDTA (Invitrogen) to the flask of cells. The cells were then incubated for 2–3 minutes at 37° C. until cells begun to detach from the surface of the flask. An equal volume of supplemented media (5 ml) was added to the flask. All the cells were collected into 50 ml tube, and centrifuged at 1000 RPM for 5 minutes at 20° C. The supernatant was aspirated and the cell pellet was resuspended in 10 ml of supplemented media and the cells were counted. 1–3 million cells/flask were seeded into 5–7 tissue culture flasks (175 cm$^2$). Each flask contained 50 ml of supplemented media. The flasks were incubated until about 90% confluent. The passaging of the cells was repeated until enough cells have been grown for tumor implantation.

The above procedure for trypsinizing and centrifuging the cells were followed. The supernatant was aspirated and the cell pellet was resuspended in 10 ml of sterile PBS and the cells were counted. The cells were centrifuged and then resuspended with appropriate volume of sterile PBS for injection of correct number of cells needed for tumor implantation. In the case of MDA-435, 100 million cells were suspended with 2.0 ml of sterile PBS to a final concentration of 50 million cells/ml in order to inject 5 million cells in 0.1 ml/mouse.

Mice (CD-1 nu/nu) were obtained from Charles River Laboratories: nomenclature: Crl:CD-1-nuBR, Age: 6–8 weeks. The mice were allowed to acclimate for 1 week prior to their being used in an experimental procedure.

Implantation of the MDA-435 tumor cell suspension took place into the corpus adiposum of the female CD-1 nu/nu mouse. This fat body is located in the ventral abdominal viscera of the mouse. Tumor cells were implanted subsutaneously into the fat body located in the right quadrant of the abdomen at the juncture of the os coxae (pelvic bone) and the os femoris (femur). 5 million MDA-435 cells in 0.1 ml of sterile PBS were injected using 27 G (½ inch) needle. MDA-435 tumors developed 2–3 weeks after implantation.

Compound stock solutions were prepared by dissolving the compound in cell-culture-grade DMSO (dimethyl sulfoxide) at the desired concentration. This stock solution in DMSO was sonicated in an ultrasonic water bath until all the powder dissolved.

The Formulation Solvent was prepared as follows: 20% of Cremophore RH40 (Polyoxyl 40 Hydrogenated Castor Oil obtained from BASF corp.) in water was prepared by first heating 100% Cremophore RH40 in a water bath at 50–60° C. until it liquefied and became clear. 10 ml of the 100% Cremophore RH40 aliquoted into a conical centrifuge tube containing 40 ml of sterile water (1:5 dilution of Cremophore RH40). The 20% Cremophore RH40 solution was reheated until it became clear again, and mixed by inverting the tube several times. This 20% Cremophore RH40 solution was stored at room temperature, and was kept for up to 3 months.

Preparation of Dosing Solution for Compound Administration: The compound stock solution was diluted 1:10 with 20% Cremophore RH40: 1) 2.0 ml of 10 mg/ml dosing solution of Compound (1) was prepared by diluting 100 mg/ml Compound Stock solution with 1.8 ml of 20% Cremophore RH40 water solution; and 2) a dosoing solution comprising 2.0 ml of 1 mg/ml of Paclitaxel (obtained from Sigma Chemical Co.) and 5 mg/ml of Compound (1) was obtained by mixing 0.1 ml of Compound 1 DMSO stock solution (50 mg/ml) and 0.1 ml of Paclitaxel DMSO stock solution (10 mg/ml) and diluting with 1.8 ml of 20% Cremophore RH40 water solution. The final formulatior for the dosing solution was 10% DMSO, 18% Cremophore RH40 and 72% water.

The Dosing Solution (Dosing Volume: 0.01 ml/gram=10 ml/kg) was injected intravenously into the mice bearing MDA-435 human breast tumor.

| Group | Compounds | PROTOCOL (Dose) |
|---|---|---|
| 1 | Vehicle Only | |
| 2 | Paclitaxel | (5 mg/kg) |
| 3 | Compound (1) | (50 mg/kg) |
| 4 | Paclitaxel | (5 mg/kg) + Compound (1) (25 mg/kg) |
| 5 | Paclitaxel | (5 mg/kg) + Compound (1) (50 mg/kg) |

Figure 2:
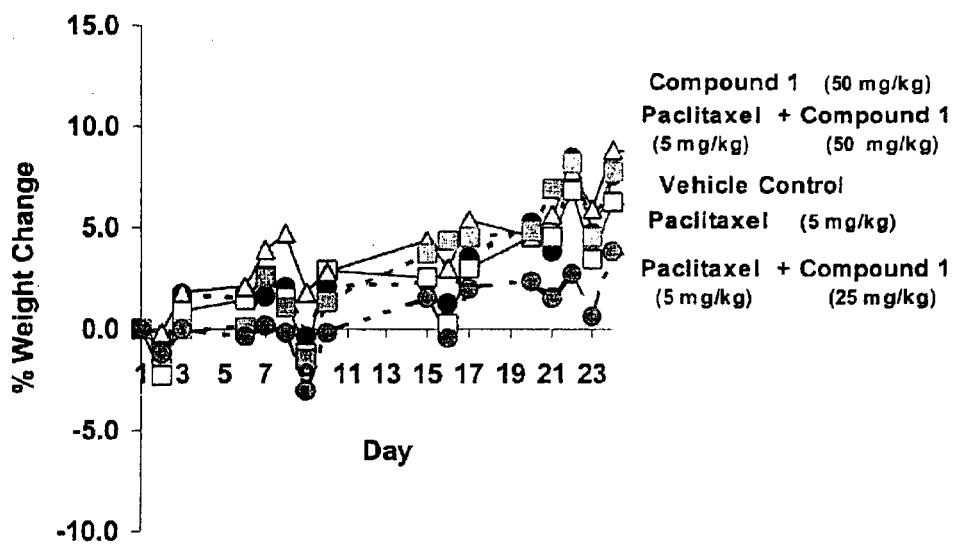
FIG. 2 is a graph showing the percent weight change over time in nude mice treated with vehicle; Compound (1) (50 mg/kg); Paclitaxel (5 mg/kg); Compound (1) (25 mg/kg) and Paclitaxel (5 mg/kg); or Compound (1) (50 mg/kg) and Paclitaxel (5 mg/kg). The mice were being treated for tumors generated from the human breast tumor cell line MDA-435.
Figure 3:
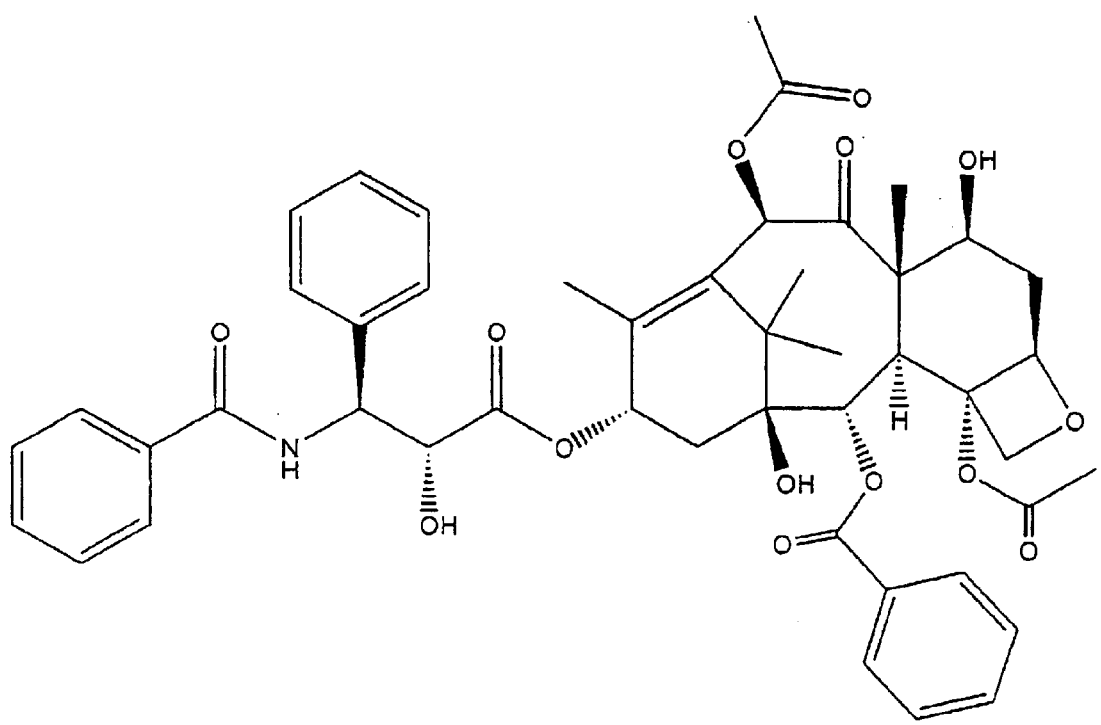
FIG. 3 is the structure of taxol (Paclitaxel)

Dosing Schedule: 3 times a week (Monday, Wednesday, Friday) for 3 weeks 5 mice were used for each group Results FIG. 1 shows the effects of Compound (1) on enhancing anti-tumor activity of Paclitaxel (Taxol). As can be seen from FIG. 1, Compound (1) significantly enhanced anti-tumor activity of Paclitaxel on human breast tumor MDA-435 in nude mice. FIG. 2 shows the effects of Compound (1) and Paclitaxel on the body weight of nude mice bearing MDA-435 human breast tumor. As can be seen from FIG. 2, Compound (1) significantly enhanced anti-tumor activity of Paclitaxel without increasing toxicity.

Example 13

Compounds (1) and (2) Enhance the Anticancer Activity of Paclitaxel in vivo

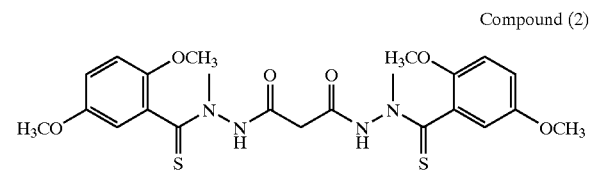

Compound (2)

The protocol described in Example 12 was used to test Compounds (1) and (2) for their ability to enhance the anti-cancer activity of paclitaxel in mice, except as modified as described below.

PROTOCOL

| Group | Compounds | (Dose) |
|---|---|---|
| 1 | Vehicle Only | |
| 2 | Paclitaxel | (2 mg/kg) |
| 3 | Paclitaxel | (5 mg/kg) |
| 4 | Compound (1) | (80 mg/kg) |
| 5 | Compound (2) | (80 mg/kg) |
| 6 | Paclitaxel | (2 mg/kg) + Compound (1) (80 mg/kg) |
| 7 | Paclitaxel | (5 mg/kg) + Compound (1) (80 mg/kg) |
| 8 | Paclitaxel | (2 mg/kg) + Compound (2) (80 mg/kg) |
| 9 | Paclitaxel | (5 mg/kg) + Compound (2) (80 mg/kg) |

Dosing Schedule: 3 times a week (Monday, Wednesday, Friday) for 3 weeks 5 mice were used for each group.

RESULTS

| Group | Average Tumor Volume (mm³) on Day 23 | % Tumor Growth |
|---|---|---|
| 1 | 301.3 | 100 |
| 2 | 259.8 | 86 |
| 3 | 164.8 | 55 |
| 4 | 270.0 | 90 |
| 5 | 305.8 | 101 |
| 6 | 193.3 | 64 |
| 7 | 106.2 | 35 |
| 8 | 148.4 | 49 |
| 9 | 60.6 | 20 |

Compounds (1) and (2) significantly enhanced anti-tumor activity of Paclitaxel at both of 2 mg/kg and 5 mg/kg without increasing toxicity.

Example 14

Compound (1) Enhances the Anticancer Activity of Paclitaxel in vivo

The protocol described in Example 12 was used to test Compound (1) for its ability to enhance the anti-cancer activity of paclitaxel in mice, except modified as described below.

PROTOCOL

| Group | Compounds | (Dose) |
|---|---|---|
| 1 | Vehicle Only | |
| 2 | Paclitaxel | (10 mg/kg) |
| 3 | Compound (1) | (50 mg/kg) |
| 4 | Paclitaxel | (10 mg/kg) + Compound (1) (25 mg/kg) |

Dosing Schedule:
3 times a week (Monday, Wednesday, Friday) for 3 weeks
5 mice were used for each group

RESULTS

| Group | Average Tumor Volume [mm³] | % Tumor Growth Inhibition on Day 48 |
|---|---|---|
| 1 | 752.2 | — |
| 2 | 105.4 | 86% |
| 3 | 754.9 | 0% |
| 4 | 0.59 | >99.9% |

When 10 mg/kg of Paclitaxel was used, significant anti-tumor activity was observed. However, after drug treatment (Day 1–20) terminated, the tumor started growing to become 105 mm³ volume on Day 43. On the other hand, average tumor volume after treatment of Paclitaxel (10 mg/kg) plus Compound (1) (25 mg/kg) was only 0.59 mm³ with more than 99.9% tumor growth inhibition.

Example 15

Compounds (3)–(5) Enhance the Anticancer Activity of Paclitaxel in vivo

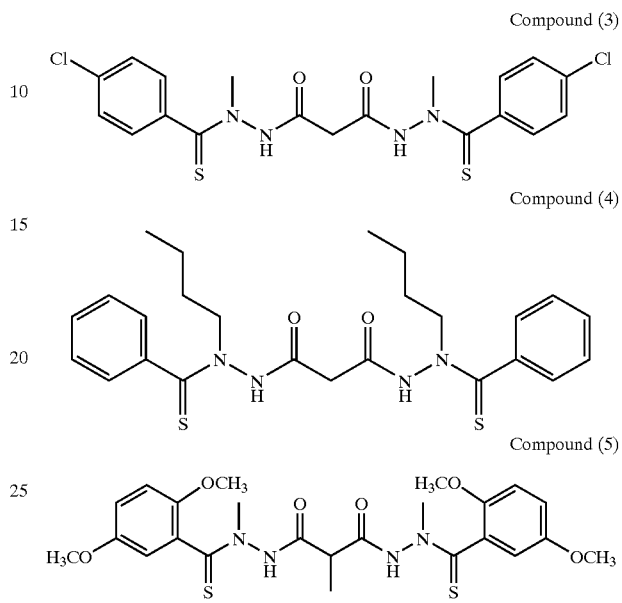

The protocol described in Example 12 was used to test Compounds (3)–(5) for their ability to enhance the anti-cancer activity of paclitaxel in mice, except modified as described below.

PROTOCOL

| Group | Compounds | (Dose) |
|---|---|---|
| 1 | Vehicle Only | |
| 2 | Paclitaxel | (5 mg/kg) |
| 3 | Paclitaxel | (5 mg/kg) + Compound (3) (50 mg/kg) |
| 4 | Paclitaxel | (5 mg/kg) + Compound (4) (100 mg/kg) |
| 5 | Paclitaxel | (5 mg/kg) + Compound (5) (100 mg/kg) |

Dosing Schedule:
3 times a week (Monday, Wednesday, Friday) for 3 weeks
5 mice were used for each group

RESULTS

| Group | Average % Tumor Growth Inhibition on Day 27 |
|---|---|
| 2 | 19 |
| 3 | 76 |
| 4 | 66 |
| 5 | 79 |

Compounds (3)–(5) demonstrated significant enhancing effects of Taxol anti-tumor activity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound represented by the following structural formula:

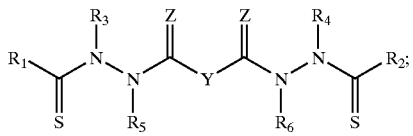

or a pharmaceutically acceptable salt thereof, wherein:
Y is a covalent bond, a phenylene group or a substituted or unsubstituted straight chained hydrocarbyl group, or, Y, taken together with both >C=Z groups to which it is bonded, is a substituted or unsubstituted aromatic group;
$R_1$ and $R_2$ are independently an aryl group or a substituted aryl group;
$R_3$ and $R_4$ are independently —H, an aliphatic group, a substituted aliphatic group, an aryl group or a substituted aryl group;
$R_5$–$R_6$ are independently —H, an aliphatic group, a substituted aliphatic group, an aryl group or a substituted aryl group; and
Z is =O or =S;
provided that when Y is —CH$_2$—, $R_3$ and $R_4$ are both phenyl and $R_5$–$R_6$ are all —H, then $R_1$ and $R_2$ are not both phenyl.

2. The compound of claim 1 wherein Y is a covalent bond or a substituted or unsubstituted straight chained hydrocarbyl group, or, Y, taken together with both >C=Z groups to which it is bonded, is a substituted or unsubstituted aromatic group.

3. The compound of claim 2 wherein Y, taken together with both >C=Z groups to which it is bonded, is a substituted or unsubstituted arylene group.

4. The compound of claim 3 wherein the compound is represented by the following structural formula;

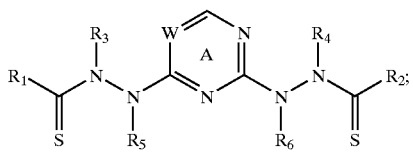

wherein Ring A is substituted or unsubstituted and W is —CH— or —N—.

5. The compound of claim 2 wherein Y is a covalent bond or a substituted or unsubstituted straight chained hydrocarbyl group.

6. The compound of claim 2 wherein the compound is represented by the following structural formula:

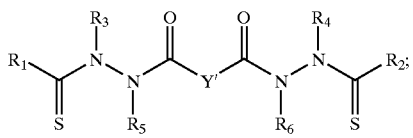

wherein Y' is a covalent bond or —CR$_7$R$_8$—and $R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2–C6 substituted or unsubstituted alkylene group.

7. The compound of claim 6 wherein at least one of $R_1$–$R_4$ is a heteroaryl group, a substituted heteroaryl group, or a phenyl group substituted with at least one group other than an aliphatic group when $R_5$–$R_8$ are all —H.

8. The compound of claim 6 wherein at least one of $R_1$–$R_4$ is a heteroaryl group, a substituted heteroaryl group, or a phenyl group substituted with at least one group other than an aliphatic group.

9. The compound of claim 8 wherein $R_3$ and $R_4$ are both methyl.

10. The compound of claim 6 wherein the compound is represented by the following structural formula:

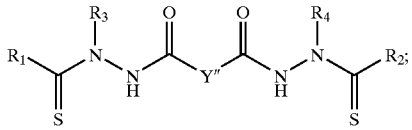

wherein Y" is a covalent bond or —CH$_2$—.

11. The compound of claim 10 wherein $R_1$ and $R_2$ are different and/or $R_3$ and $R_4$ are different.

12. The compound of claim 10 wherein $R_1$ and $R_2$ are the same and $R_3$ and $R_4$ are the same.

13. The compound of claim 12 wherein $R_3$ and $R_4$ are both a lower alkyl group or a substituted lower alkyl group.

14. The compound of claim 13 wherein $R_3$ and $R_4$ are both a lower alkyl group substituted with substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NR$^c$)—NH$_2$, —NR$^d$—C(=NH—NHR$^a$, —NR$^d$—C(=NH)—N(R$^a$R$^b$), —NR$^d$—C(=NR$^c$)—NH$_2$, NR$^d$—C(=NR$^c$)—NHR$^a$, —NR$^d$—C(=NR$^c$)—N(R$^a$R$^b$) —NHNH$_2$, —NHNHR$^a$, —NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, non-aromatic heterocyclic group, substituted non-aromatic heterocyclic group, benzyl group, substituted benzyl group, aryl group or substituted aryl group wherein R$^a$–R$^b$ are each independently an alkyl group, substituted alkyl group, benzyl, substituted benzyl, aromatic or substituted aromatic group, or, [[—NR$^a$R$^d$]]—N(R$^a$R$^b$), taken together, can also form a substituted or unsubstituted non-aromatic heterocyclic group.

15. The compound of claim 13 wherein $R_3$ and $R_4$ are both methyl or ethyl.

16. The compound of claim 15 wherein $R_1$ and $R_2$ are both a phenyl group substituted with at least one group other than an aliphatic group; or $R_1$ and $R_2$ are both heteroaryl or substituted heteroaryl groups.

17. The compound of claim 12 wherein $R_3$ and $R_4$ are both a heteroaryl group or a substituted heteroaryl group.

18. The compound of claim 17 wherein $R_1$ and $R_2$ are both a substituted or unsubstituted phenyl group; or $R_1$ and $R_2$ are both a substituted or unsubstituted heteroaryl group.

19. The compound of claim 12 wherein $R_3$ and $R_4$ are both a substituted phenyl group.

20. The compound of claim 19 wherein $R_3$ and $R_4$ are both a phenyl group substituted with at least one group other than an aliphatic group.

21. The compound of claim 20 wherein $R_1$ and $R_2$ are both heteroaryl or substituted heteroaryl groups; or $R_1$ and $R_2$ are both substituted or unsubstituted phenyl groups.

22. The compound of claim 19 wherein $R_3$ and $R_4$ are both a phenyl group substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$)—NR$^a$—C(=NR$^c$)—NH$_2$, —NR$^d$—C(=NR$^c$)—NHR$_a$, —NR$^d$—C(=NR$^c$)—N(R$^a$R$^b$), —NHNH$_2$, —NHNHR$^a$—NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl group, substituted alkyl group, non—aromatic heterocyclic group, substituted non—aromatic heterocyclic group, benzyl group, substituted benzyl group, aryl group or substituted aryl group wherein R$^a$–R$^d$ are each independently an alkyl group, substituted alkyl group, benzyl, substituted benzyl, aromatic or substituted aromatic group, or, [[—NR$^a$R$^d$]]—N(R$^a$R$^b$), taken together, can also form a substituted or unsubstituted non—aromatic heterocyclic group.

23. The compound of claim 12 wherein $R_1$ and $R_2$ are both a heteroaryl group or a substituted heteroaryl group.

24. The compound of claim 12 wherein $R_1$ and $R_2$ are both a substituted phenyl group.

25. The compound of claim 12 wherein $R_1$ and $R_2$ are both a phenyl group substituted with at least one group other than an aliphatic group.

26. The compound of claim 24 wherein $R_1$ and $R_2$ are both a phenyl group substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$)—NR$^a$—C(=NR$^c$)—NH$_2$, —NR$^d$—C(=NR$^c$)—NHR$_a$, —NR$^d$—C(=NR$^c$)—N(R$^a$R$^b$), —NHNH$_2$, —NHNHR$^a$—NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl group, susbstituted alkyl group, non-aromatic heterocyclic group, substituted non-aromatic heterocyclic group, benzyl group, substituted benzyl group, aryl group or substituted aryl group wherein R$^a$–R$^d$ are each independently an alkyl group, substituted alkyl group, benzyl, substituted benzyl, aromatic or substituted aromatic group, or, [[—NR$^a$R$^d$]]—N(R$^a$R$^b$), taken together, can also form a substituted or unsubstituted non-aromatic heterocyclic group.

27. The compound of claim 5 wherein the compound is represented by the following structural formula:

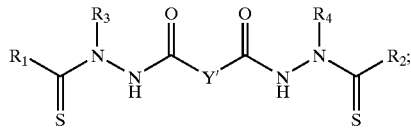

wherein Y' is a covalent bond or —CR$_7$R$_8$—.

28. The compound of claim 27 wherein $R_7$ and $R_8$ are different.

29. The compound of claim 27 where $R_1$ and $R_2$ are the same; and $R_3$ and $R_4$ are the same.

30. The compound of claim 27 wherein $R_1$ and $R_2$ are both aryl or substituted aryl groups and $R_3$ and $R_4$ are both a lower alkyl group or a substituted lower alkyl group.

31. The compound of claim 30 wherein $R_1$ and $R_2$ are both phenyl or substituted phenyl and $R_3$ and $R_4$ are both methyl, ethyl, phenyl, or thienyl.

32. The compound of claim 31 wherein $R_7$ and $R_8$ are both methyl or wherein $R_7$ and $R_8$, taken together, are propylene or butylene.

33. The compound of claim 31 wherein $R_7$ is —H and $R_8$ is lower alkyl, thienyl, phenyl or benzyl.

34. The compound of claim 31 wherein $R_1$ and $R_2$ are both phenyl substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$)—NR$^a$—C(=NR$^c$)—NH$_2$, —NR$^d$—C(=NR$^c$)—NHR$_a$, —NR$^d$—C(=NR$^c$)—N(R$^a$R$^b$), —NHNH$_2$, —NHNHR$^a$—NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl group, substituted alkyl group, non-aromatic heterocyclic group, substituted non-aromatic heterocyclic group, benzyl group, substituted benzyl group, aryl group or substituted aryl group wherein R$^a$–R$^d$ are each independently an alkyl group, substituted alkyl group, benzyl, substituted benzyl, aromatic or substituted aromatic group, or, [[—NR$^a$R$^d$]]—N(R$^a$R$^b$), taken together, can also form a substituted or unsubstituted non-aromatic heterocyclic group.

35. A compound represented by the following structural formula:

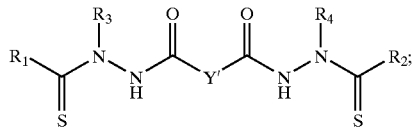

or a physiologically acceptable salt thereof, wherein:

Y' is a covalent bond or —CR$_7$R$^8$—;

R$_1$ and R$_2$ are both a substituted or unsubstituted aryl group;

R$_3$ and R$_4$ are both —H, methyl or ethyl; and

R$_7$ is —H and R$_8$ is —H or methyl.

36. The compound of claim 35 wherein R$_1$ and R$_2$ are both phenyl substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$—C(=NH)—N(R$^a$R$^b$)—NR$^a$—C(=NR$^c$)—NH$_2$, —NR$^d$—C(=NR$^c$)—NHR$_a$, —NR$^d$—C(=NR$^c$)—N(R$^a$R$^b$), —NHNH$_2$, —NHNHR$^a$—NHR$^a$R$^b$, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl group, substituted alkyl group, non-aromatic heterocyclic group, substituted non-aromatic heterocyclic group, benzyl group, substituted benzyl group, aryl group or substituted aryl group wherein R$^a$–R$^d$ are each independently an alkyl group, substituted alkyl group, benzyl, substituted benzyl, aromatic or substituted aromatic group, or, [[—NR$^a$R$^d$]]—(R$^a$R$^b$), taken together, can also form a substituted or unsubstituted non-aromatic heterocyclic group.

37. The compound of claim 6 wherein R$_5$ and R$_6$ are the same.

38. The compound of claim 37 wherein the compound is represented by the following structural formula:

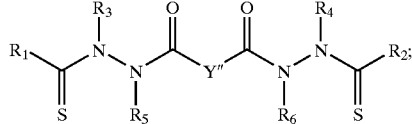

wherein Y″ is a covalent bond or —CH$_2$.

39. The compound of claim 38 wherein R$_5$ and R$_6$ are both a lower alkyl group or a phenyl group.

40. The compound of claim 39 wherein R$_5$ and R$_6$ are both a methyl group.

41. The compound of claim 39 wherein R$_1$ and R$_2$ are both phenyl or substituted phenyl; R$_3$ and R$_4$ are both a lower alkyl group; and R$_5$ and R$_6$ are both a lower alkyl group.

42. A compound represented by the following structural formula:

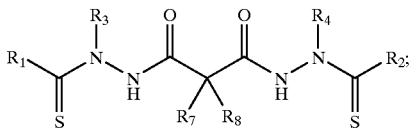

or a physiologically acceptable salt thereof, wherein a) R$_1$ and R$_2$ are both phenyl; R$_3$ and R$_4$ are both methyl; R$_7$ and R$_8$ are both —H;

b) R$_1$ and R$_2$ are both phenyl; R$_3$ and R$_4$ are both ethyl; R$_7$ and R$_8$ are both —H;

c) R$_1$ and R$_2$ are both 4-cyanophenyl; R$_3$ and R$_4$ are both methyl; R$_7$ is methyl; R$_8$ is —H;

d) R$_1$ and R$_2$ are both 4-methoxyphenyl; R$_3$ and R$_4$ are both methyl; R$_7$ and R$_8$ are both —H;

e) R$_1$ and R$_2$ are both phenyl; R$_3$ and R$_4$ are both methyl; R$_7$ is methyl; R$_8$ is —H;

f) R$_1$ and R$_2$ are both phenyl; R$_3$ and R$_4$ are both ethyl; R$_7$ is methyl; R$_8$ is —H;

g) R$_1$ and R$_2$ are both 4-cyanophenyl; R$_3$ and R$_4$ are both methyl; R$_7$ and R$_8$ are both —H;

h) R$_1$ and R$_2$ are both 2,5-dimethoxyphenyl; R$_3$ and R$_4$ are both methyl; R$_7$ and R$_8$ are both —H;

i) R$_1$ and R$_2$ are both 2,5-dimethoxyphenyl; R$_3$ and R$_4$ are both methyl; R$_7$ is methyl; R$_8$ is—H;

j) R$_1$ and R$_2$ are both 3-cyanophenyl; R$_3$ and R$_4$ are both methyl; R$_7$ and R$_8$ are both —H;

k) R$_1$ and R$_2$ are both 3-fluorophenyl; R$_3$ and R$_4$ are both methyl; R$_7$ and R$_8$ are both —H;

l) R$_1$ and R$_2$ are both 4-chlorophenyl; R$_3$ and R$_4$ are both methyl; R$_7$ is methyl; R$_8$ is —H;

m) R$_1$ and R$_2$ are both 2-dimethoxyphenyl; R$_3$ and R$_4$ are both methyl; R$_7$ and R$_8$ are both —H;

n) R$_1$ and R$_2$ are both 3-methoxyphenyl; R$_3$ and R$_4$ are both methyl; R$_7$ and R$_8$ are both —H;

o) R$_1$ and R$_2$ are both 2,3-dimethoxyphenyl; R$_3$ and R$_4$ are both methyl; R$_7$ and R$_8$ are both —H;

p) R$_1$ and R$_2$ are both 2,3-dimethoxyphenyl; R$_3$ and R$_4$ are both methyl; R$_7$ is methyl; R$_8$ is—H;

q) R$_1$ and R$_2$ are both 2,5-difluorophenyl; R$_3$ and R$_4$ are both methyl; R$_7$ and R$_8$ are both —H;

r) R$_1$ and R$_2$ are both 2,5-difluorophenyl; R$_3$ and R$_4$ are both methyl; R$_7$ is methyl; R$_8$ is —H;

s) R$_1$ and R$_2$ are both 2,5-dichlorophenyl; R$_3$ and R$_4$ are both methyl; R$_7$ and R$_8$ are both —H;

t) R$_1$ and R$_2$ are both 2,5-dimethyLphenyl; R$_3$ and R$_4$ are both methyl; R$_7$ and R$_8$ are both —H;

u) R$_1$ and R$_2$ are both 2,5-dimethoxyphenyl; R$_3$ and R$_4$ are both methyl; R$_7$ and R$_8$ are both —H;

v) R$_1$ and R$_2$ are both phenyl; R$_3$ and R$_4$ are both methyl; R$_7$ and R$_8$ are both —H; or w) R$_1$ and R$_2$ are both 2,5-dimethoxyphenyl; R$_3$ and R$_4$ are both methyl; R$_7$ is methyl; R$_8$ is —H.

43. A compound represented by the following structural formula:

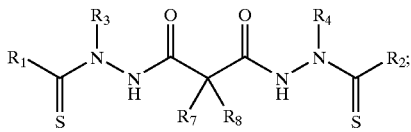

or a physiologically acceptable salt thereof wherein:

a) $R_1$ and $R_2$ are both 4-cyanophenyl; $R_3$ and $R_4$ are both methyl; $R_7$ is methyl; $R_8$ is —H;

b) $R_1$ and $R_2$ are both 2,5-dimethoxyphenyl; $R_3$ and $R_4$ are both methyl; $R_7$ and $R_8$ are both —H;

c) $R_1$ and $R_2$ are both 2,5-dimethoxyphenyl; $R_3$ and $R_4$ are both methyl; $R_7$ is methyl; $R_8$ is —H;

d) $R_1$ and $R_2$ are both 3-fluorophenyl; $R_3$ and $R_4$ are both methyl; $R_7$ and $R_8$ are both —H;

e) $R_1$ and $R_2$ are both 2,3-dimethoxyphenyl; $R_3$ and $R_4$ are both methyl; $R_7$ and $R_8$ are both —H; or f) $R_1$ and $R_2$ are both phenyl; $R_3$ and $R_4$ are both methyl; $R_7$ and $R_8$ are both —H.

44. A pharmaceutical composition comprising a pharmaceutically acceptable carrier or diluent and a compound represented by the following structural formula:

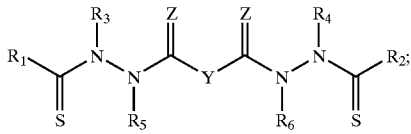

or a pharmaceutically acceptable salt thereof, wherein:

Y is a covalent bond, phenylene group or a substituted or unsubstituted straight chained hydrocarbyl group, or, Y, taken together with both >C=Z groups to which it is bonded, is a substituted or unsubstituted aromatic group;

$R_1$ and $R_2$ are independently an aryl group or a substituted aryl group, $R_3$ and $R_4$ are independently —H, an aliphatic group, a substituted aliphatic group, an aryl group or a substituted aryl group;

$R_5$—$R_6$ are independently —H, an aliphatic group, a substituted aliphatic group, an aryl group or a substituted aryl group; and Z is =O or =S.

45. The pharmaceutical composition of claim 44 wherein Y is a covalent bond, phenylene group or a substituted or unsubstituted straight chained hydrocarbyl group, or, Y, taken together with both >C=Z groups to which it is bonded, is a substituted or unsubstituted aromatic group.

46. The pharmaceutical composition of claim 45 wherein Y, taken together with both >C=Z groups to which it is bonded, is a substituted or unsubstituted aromatic group.

47. The pharmaceutical composition of claim 46 wherein the compound is represented by the following structural formula:

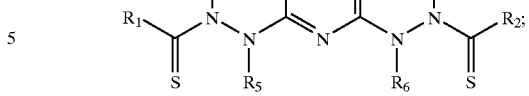

wherein Ring A is substituted or unsubstituted and W is —CH— or —N—.

48. The pharmaceutical composition of claim 45 wherein Y is a covalent bond or a substituted or unsubstituted hydrocarbyl group.

49. The pharmaceutical composition of claim 45 wherein the compound is represented by the following structural formula:

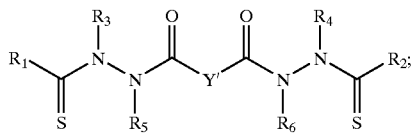

wherein Y' is a covalent bond or —$CR_7R_8$— and $R_7$ and $R_8$ are each independently —H, an aliphatic or substituted aliphatic group, or $R_7$ is —H and $R_8$ is a substituted or unsubstituted aryl group, or, $R_7$ and $R_8$, taken together, are a C2–C6 substituted or unsubstituted alkylene group.

50. The pharmaceutical composition of claim 45 wherein the compound is represented by the following structural formula:

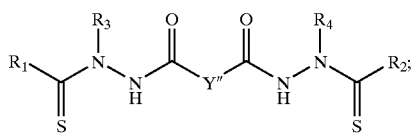

wherein Y" is a covalent bond or —$CH_2$—.

51. The pharmaceutical composition of claim 50 wherein $R_1$ and $R_2$ are different and/or $R_3$ and $R_4$ are different.

52. The pharmaceutical composition of claim 50 wherein $R_1$ and $R_2$ are the same and $R_3$ and $R_4$ are the same.

53. The pharmaceutical composition of claim 52 wherein $R_3$ and $R_4$ are both a lower alkyl group or a substituted lower alkyl group.

54. The pharmaceutical composition of claim 53 wherein $R_3$ and $R_4$ are both methyl or ethyl.

55. The pharmaceutical composition of claim 54 wherein $R_1$ and $R_2$ are both an aryl or substituted aryl group.

56. The pharmaceutical composition of claim 54 wherein $R_1$ and $R_2$ are both a phenyl group or a substituted phenyl group.

57. The pharmaceutical composition of claim 54 wherein $R_1$ and $R_2$ are both a phenyl group substituted with one or more groups selected from —OH, —Br, —Cl, —I, —F, —$OR^a$, —O—$COR^a$, —$COR^a$ —CN, —$NO_2$, —COON, —$SO_3H$, —$NHR^a$, —$N(R^aR^b)$, —$COOR^a$, —CHO, —$CONH_2$, —$CONHR^a$, —$CON(R^aR^b)$, —$NHCOR^a$—, —$NRCOR^a$, —$NHCONH_2$, —$NHCONR^aH$, —NHCON$(R^aR^b)$, —$NR^cCONH_2$, —$NR^cCONR^aH$, —$NR^cCON(R^aR^b)$, —C(=NH)—$NH_2$, —C(=NH)—$NHR_2$, —C(=NH)—N($R^aR^b$), —C(=$NR^c$)—$NH_2$, —C(=$NR^c$)—$NHR^a$, —C(=$NR^c$)—N($R^aR^b$), —NH—C(=NH)—$NH_2$, —NH—C(=NH)—$NHR^a$, —NH—C(=NH)—N($R^aR^b$), —NH—C(=$NR^c$)—$NH_2$, —NH—C (=NR$^c$)—NHR$^a$, —NH—C(=NR$^c$)—N—NR$^d$H—C(=NH)—NH$_2$, —NR$^d$—C(=NH)—NHR$^a$, —NR$_d$—C(=NH)—(R$^a$R$^b$), —NR$^d$—C(=NR$^c$)—NH$_2$, —NR$^d$—C(=NR$^c$)—NHR$^a$, —NR$^d$—C=NR$^c$)—N(R$^a$R$^b$)—NHNH$_2$, —NHNHR$^a$, —NHR$^a$R$^b$—, —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl group, substituted alkyl group, non-aromatic heterocyclic group, substituted non-aromatic heterocyclic group, benzyl group, substituted benzyl group, aryl group or substituted aryl group wherein R$^a$-R$^d$ are independently an alkyl group, substituted alkyl group, benzyl, substituted benzyl, aromatic or substituted aromatic group, or, [[—NR$^a$R$^d$]]—N(R$^a$R$^b$) taken together, can also form a substituted or unsubstituted non-aromatic heterocyclic group.

58. The pharmaceutical composition of claim 52 wherein R$_3$ and R$_4$ are both a phenyl group or a substituted phenyl group.

59. The pharmaceutical composition of claim 58 wherein R$_1$ and R$_2$ are both a phenyl or substituted phenyl group.

60. The pharmaceutical composition of claim 52 wherein R$_1$ and R$_2$ are both a substituted phenyl group.

61. The pharmaceutical composition of claim 49 wherein the compound is represented by the following structural formula:

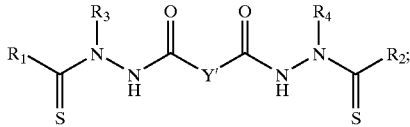

wherein Y' is a covalent bond or —CR$_7$R$_8$—.

62. The pharmaceutical composition of claim 61 wherein R$_7$ and R$_8$ are different.

63. The pharmaceutical composition of claim 61 where R$_1$ and R$_2$ are the same; R$_3$ and R$_4$ are the same; and R$_7$ and R$_8$ are the same.

64. The pharmaceutical composition of claim 61 wherein R$_1$ and R$_2$ are both aryl or substituted aryl groups and R$_3$ and R$_4$ are both a lower alkyl group or a substituted lower alkyl group.

65. The pharmaceutical composition of claim 61 wherein R$_1$ and R$_2$ are both phenyl or substituted phenyl and R$_3$ and R$_4$ are methyl, ethyl, phenyl, or thienyl.

66. The pharmaceutical composition of claim 65 wherein R$_7$ and R$_8$ are both methyl or wherein R$_7$ and R$_8$, taken together, are propylene or butylene.

67. The pharmaceutical composition of claim 65 wherein R$_7$ is —H and R$_8$ is lower alkyl, thienyl, phenyl or benzyl.

68. The pharmaceutical composition of claim 65 wherein R$_1$ and R$_2$ are both phenyl substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^a$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$C(=NH)—N(R$^a$R$^b$), —NR$^d$C(=NR$^c$)—NH$_2$, —NR$^d$—C(=NR$^c$)—NHR$^a$, —NR$^c$—C(=NR$^c$)—N(R$^a$R$^b$), —NHNH$_2$, —NHNHR$^a$, —NHR$^a$R$^b$, —SO$_{NH2}$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl groups, substituted alkyl group, non-aromatic heterocyclic group, substituted non-aromatic heterocyclic group, benzyl group, substituted benzyl group, aryl group or substituted aryl group wherein R$^a$-R$^d$ are each independently an alkyl group, substituted alkyl group, benzyl, substituted benzyl, aromatic or substituted aromatic group, or, [[—NR$^a$R$^d$]]—N(R$^a$R$^b$), taken together, can also form a substituted or unsubstituted non-aromatic heterocyclic group.

69. A pharmaceutical composition comprising a pharmaceutically acceptable carrier or diluent and a compound represented by the following structural formula:

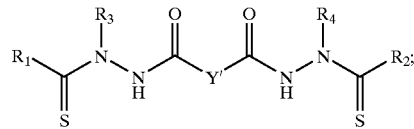

or a physiologically acceptable salt thereof, wherein:

Y' is a covalent bond or —CR$_7$R$_8$—;

R$_1$ and R$_2$ are both a substituted or unsubstituted aryl group;

R$_3$ and R$_4$ are both —H, methyl or ethyl; and

R$_7$ is —H and R$_8$ is —H or methyl.

70. The pharmaceutical composition of claim 69 wherein R$_1$ and R$_2$ are both phenyl substituted with one or more groups selected from —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^a$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$H—C(=NH)—NH$_2$, —NR$^d$—C(=NH)—NHR$^a$, —NR$^d$C(=NH)—N(R$^a$R$^b$), —NR$^d$C(=NR$^c$)—NH$_2$, —NR$^d$—C(=NR$^c$)—NHR$^a$, —NR$^c$—C(=NR$^c$)—N(R$^a$R$^b$), —NHNH$_2$, —NHNHR$^a$, —NHR$^a$R$^b$, —SO$_{NH2}$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, alkyl groups, substituted alkyl group, non-aromatic heterocyclic group, substituted non-aromatic heterocyclic group, benzyl group, substituted benzyl group, aryl group or substituted aryl group wherein R$^a$-R$^d$ are each independently an alkyl group, substituted alkyl group, benzyl, substituted benzyl, aromatic or substituted aromatic group, or, [[—NR$^a$R$^d$]]—N(R$^a$R$^b$), taken together, can also form a substituted or unsubstituted non-aromatic heterocyclic group.

71. The pharmaceutical composition of claim 49 wherein R$_5$ and R$_6$ are the same.

72. The pharmaceutical composition of claim 71 wherein the compound is represented by the following structural formula:

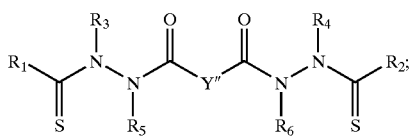

wherein Y" is a covalent bond or —CH$_2$—.

73. The pharmaceutical composition of claim 72 wherein R$_5$ and R$_6$ are both a lower alkyl group or a phenyl group.

74. The pharmaceutical composition of claim 73 wherein R$_5$ and R$_6$ are both a methyl group.

75. The pharmaceutical composition of claim 72 wherein R$_1$ and R$_2$ are both phenyl or substituted phenyl; R$_3$ and R$_4$ are both a lower alkyl group; and R$_5$ and R$_6$ are both a lower alkyl group.

76. A pharmaceutical composition comprising a pharmaceutically acceptable carrier or diluent and a compound represented by the following structural formula:

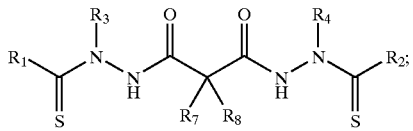

or physiologically acceptable salt thereof, wherein:

a) R$_1$ and R$_2$ are both phenyl; R$_3$ and R$_4$ are both phenyl; R$_7$ and R$_8$ are both —H;
b) R$_1$ and R$_2$ are both phenyl; R$_3$ and R$_4$ are both methyl; R$_7$ and R$_8$ are both —H;
c) R$_1$ and R$_2$ are both phenyl; R$_3$ and R$_4$ are both ethyl; R$_7$ and R$_8$ are both —H;
d) R$_1$ and R$_2$ are both 4-cyanophenyl; R$_3$ and R$_4$ are both methyl; R$_7$ is methyl; R$_8$ is —H;
e) R$_1$ and R$_2$ are both 4-methoxyphenyl; R$_3$ and R$_4$ are both methyl; R$_7$ and R$_8$ are both —H;
f) R$_1$ and R$_2$ are both phenyl; R$_3$ and R$_4$ are both methyl; R$_7$ is methyl; R$_8$ is —H;
g) R$_1$ and R$_2$ are both phenyl; R$_3$ and R$_4$ are both ethyl; R$_7$ is methyl; R$_8$ is —H;
h) R$_1$ and R$_2$ are both 4-cyanophenyl; R$_3$ and R$_4$ are both methyl; R$_7$ and R$_8$ are both —H;
i) R$_1$ and R$_2$ are both 2,5-dimethoxyphenyl; R$_3$ and R$_4$ are both methyl; R$_7$ and R$_8$ are both —H;
j) R$_1$ and R$_2$ are both 2,5-dimethoxyphenyl; R$_3$ and R$_4$ are both methyl; R$_7$ is methyl; R$_8$ is —H;
k) R$_1$ and R$_2$ are both 3-cyanophenyl; R$_3$ and R$_4$ are both methyl; R$_7$ and R$_8$ are both —H;
l) R$_1$ and R$_2$ are both 3-fluorophenyl; R$_3$ and R$_3$ are both methyl; R$_7$ and R$_8$ are both —H;
m) R$_1$ and R$_2$ are both 4-chlorophenyl; R$_3$ and R$_4$ are both methyl; R$_7$ is methyl; R$_8$ is —H;
n) R$_1$ and R$_2$ are both 2-dimethoxyphenyl; R$_3$ and R$_4$ are both methyl; R$_7$ and R$_8$ are both —H;
o) R$_1$ and R$_2$ are both 3-methoxyphenyl; R$_3$ and R$_4$ are both methyl; R$_7$ and R$_8$ are both —H;
p) R$_1$ and R$_2$ are both 2,3-dimethoxyphenyl; R$_3$ and R$_4$ are both methyl; R$_7$ and R$_8$ are both —H;
q) R$_1$ and R$_2$ are both 2,3-dimethoxyphenyl; R$_3$ and R$_4$ are both methyl; R$_7$ is methyl; R$_8$ is —H;
r) R$_1$ and R$_2$ are both 2,5-difluorophenyl; R$_3$ and R$_4$ are both methyl; R$_7$ and R$_8$ are both —H;
s) R$_1$ and R$_2$ are both 2,5-difluorophenyl; R$_3$ and R$_4$ are both methyl; R$_7$ is methyl; R$_8$ is —H;
t) R$_1$ and R$_2$ are both 2,5-dichlorophenyl; R$_3$ and R$_4$ are both methyl; R$_7$ and R$_8$ are both —H;
u) R$_1$ and R$_2$ are both 2,5-dimethylphenyl; R$_3$ and R$_4$ are both methyl; R$_7$ and R$_8$ are both —H;
v) R$_1$ and R$_2$ are both 2,5-dimethoxyphenyl; R$_3$ and R$_4$ are both methyl; R$_7$ and R$_8$ are both —H;
w) R$_1$ and R$_2$ are both phenyl; R$_3$ and R$_4$ are both methyl; R$_7$ and R$_8$ are both —H; or
x) R$_1$ and R$_2$ are both 2,5-dimethoxyphenyl; R$_3$ and R$_4$ are both methyl; R$_7$ is methyl; R$_8$ is —H.

77. A pharmaceutical composition comprising a pharmaceutically acceptable carrier or diluent and a compound represented by the following structural formula:

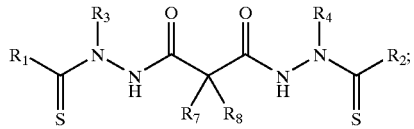

or a physiologically acceptable salt thereof, wherein:

a) R$_1$ and R$_2$ are both 4-cyanophenyl; R$_3$ and R$_4$ are both methyl; R$_7$ is methyl; R$_8$ is —H;
b) R$_1$ and R$_2$ are both 2,5-dimethoxyphenyl; R$_3$ and R$_4$ are both methyl; R$_7$ and R$_8$ are both —H;
c) R$_1$ and R$_2$ are both 2,5-dimethoxyphenyl; R$_3$ and R$_4$ are both methyl; R$_7$ is methyl; R$_8$ is —H;
d) R$_1$ and R$_2$ are both 3-fluorophenyl; R$_3$ and R$_4$ are both methyl; R$_7$ and R$_8$ are both —H;
e) R$_1$ and R$_2$ are both 2,3-dimethoxyphenyl; R$_3$ and R$_4$ are both methyl; R$_7$ and R$_8$ are both —H;
f) R$_1$ and R$_2$ are both phenyl; R$_3$ and R$_4$ are both methyl; R$_7$ and R$_8$ are both —H; or
g) R$_1$ and R$_2$ are both phenyl; R$_3$ and R$_4$ are both phenyl; R$_7$ and R$_8$ are both —H.

78. A method of treating a subject with cancer, said method comprising administering to the subject an effective amount of taxol or a taxol analog and an effective amount of a compound represented by the following structural formula:

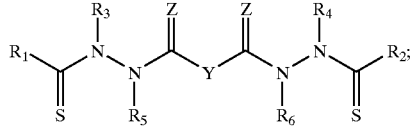

or a pharmaceutically acceptable salt thereof, wherein:

Y is a covalent bond, phenylene group or a substituted or unsubstituted hydrocarbyl group, or, Y, taken together with both >C=Z groups to which it is bonded, is a substituted or unsubstituted aromatic group;

R$_1$ and R$_2$ are independently an aryl group or a substituted aryl group;

R$_3$ and R$_4$ are independently —H, an aliphatic group, a substituted aliphatic group, an aryl group or a substituted aryl group;

R$_5$–R$_6$ are independently —H, an aliphatic group, a substituted aliphatic group, an aryl group or a substituted aryl group;

and Z is =O or =S.

79. The method of claim 78 wherein Y is a covalent bond, phenylene group or a substituted or unsubstituted hydrocarbyl group, or, Y, taken together with both >C=Z groups to which it is bonded, is a substituted or unsubstituted aromatic group.

80. The method of claim 79 wherein Y, taken together with both >C=Z groups to which it is bonded, is a substituted or unsubstituted aromatic group.

81. The method of claim 80 wherein the compound is represented by the following structural formula:

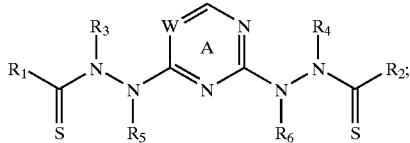

wherein Ring A is substituted or unsubstituted and W is —CH— or —N—.

82. The method of claim 79 wherein Y is a covalent bond or a substituted or unsubstituted straight chained hydrcarbyl group.

83. The method of claim 79 wherein the compound is represented by the following structural formula:

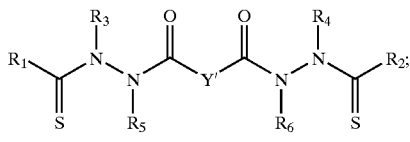

wherein Y' is a covalent bond or —CR$_7$R$_8$—and R$_7$ and R$_8$ are each independently —H, an aliphatic or substituted aliphatic group, or R$_7$ is —H and R$_8$ is a substituted or unsubstituted aryl group, or, R$_7$ and R$_8$, taken together, are a C2–C6 substituted or unsubstituted alkylene group.

84. The method of claim 83 wherein the taxol analog is represented by a structural formula selected from:

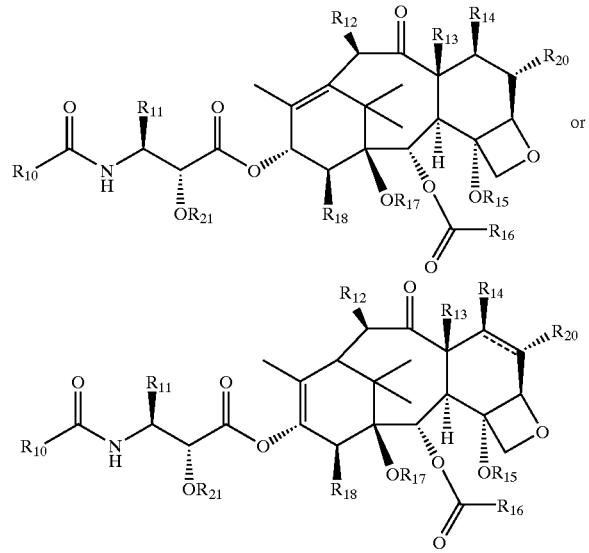

wherein:
R$_{10}$ is a lower alkyl group, a substituted lower alkyl group, a phenyl group, a substituted phenyl group, —SR$_{19}$, —NHR$_{19}$ or —OR$_{19}$;
R$_{11}$ is a lower alkyl group, a substituted lower alkyl group, an aryl group or a substituted aryl group;

R$_{12}$ is —H, —OH, lower alkyl, substituted lower alkyl, lower alkoxy, substituted lower alkoxy, —O—C(O)—(lower alkyl), —O—C(O)—(substituted lower alkyl), —O—CH$_2$—O—(lower alkyl)—S—CH$_2$—O—(lower alkyl);

R$_{13}$ is —H, —CH$_3$, or, taken together with R$_{14}$, —CH$_2$—;

R$_{14}$ is —H, —OH, lower alkoxy, —O—C(O)—(lower alkyl), substituted lower alkoxy, —O—C(O)-(substituted lower alkyl), —O—CH$_2$—O—P(O)(OH)$_2$, —O—CH$_2$—O— (lower alkyl), —O—CH$_2$—S—(lower alkyl) or, taken together with R$_{20}$, a double bond;

R$_{15}$ —H, lower acyl, lower alkyl, substituted lower alkyl, alkoxymethyl, alkthiomethyl, —OC(O)—O(lower alkyl), —OC(O)—O(substituted lower alkyl), —OC(O)—NH(lower alkyl) or —OC(O)—NH(substituted lower alkyl);

R$_{16}$ is phenyl or substituted phenyl;

R$_{17}$ is —H, lower acyl, substituted lower acyl, lower alkyl, substituted, lower alkyl, (lower alkoxy)methyl or (lower alkyl)thiomethyl;

R$_{18}$ —H, —CH$_3$ or, taken together with R$_{17}$ and the carbon atoms to which R$_{17}$ and R$_{18}$ are bonded, a five or six membered a non-aromatic heterocyclic ring;

R$_{19}$ is a lower alkyl group, a substituted lower alkyl group, a phenyl group, a substituted phenyl group;

R$_{20}$ is —H or a halogen; and

R$_{21}$ is —H, lower alkyl, substituted lower alkyl, lower acyl or substituted lower acyl.

85. The method of claim 84 wherein:

R$_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH=C(CH$_3$)$_2$ orpara—chlorophenyl;

R$_{11}$ is phenyl, (CH$_3$)$_2$CHCH$_2$—, —2-furanyl, cyclopropyl orpara-toluyl;

R$_{12}$ is —H, —OH, CH$_3$CO—or —(CH$_2$)$_2$—N—morpholino;

R$_{13}$ is methyl, or, R$_{13}$ and R$_{14}$, taken together, are R$_{14}$ is —H, —CH$_2$SCH$_3$ or —CH$_2$—O—P(O)(OH)$_2$;

R$_{15}$ is CH$_3$CO—;

R$_{16}$ is phenyl;

R$_{17}$ —H, or, R$_{17}$ and R$_{18}$, taken together, are —O—CO—O—;

R$_{18}$ is—H;

R$_{20}$ is —H or —F; and

R$_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

86. The method of claim 85 wherein the taxol analog is represented by a structure shown in any one of FIGS. 5–25.

87. The method of claim 79 wherein the taxol analog is the copolymer of N-(2-hydroxypropyl)methacrylamide, methacryloylglycine-2-hydroxypropylamide and [2aR[2α,4β,4β,6β,9α(2R,3S),11β, 12α, 12α, 12α]]-6,12b-diacetoxy-9-[3-benzamido-2-(methacryloyl-glycyl-L-phenylalanyl-L-leucyl.glycyloxy)-3-phenylpropionyloxy]-12-benzoyloxy-4,11-dihydroxy-4a,8,13,13-tetramethyl-2a,3,4,4a,5,6,9,10,11,12,12a, 12b-dodecahydro-1H-7,11-methanocyclodeca[3,4]benz[1,2-b]oxet-5-one.

88. The method of claim 79 wherein the subject is administered taxotere.

89. The method of claim 83 wherein the compound is represented by the following structural formula:

$$R_1-C(S)-N(R_3)-N(R_5)-C(O)-Y'-C(O)-N(R_6)-N(R_4)-C(S)-R_2;$$

wherein Y' is a covalent bond or —$CR_7R_8$—.

90. The method of claim 83 wherein the compound is represented by the following structural formula:

$$R_1-C(S)-N(R_3)-NH-C(O)-Y''-C(O)-NH-N(R_4)-C(S)-R_2;$$

wherein Y" is a covalent bond or —$CH_2$—.

91. The method of claim 90 wherein $R_1$ and $R_2$ are different and/or $R_3$ and $R_4$ are different.

92. The method of claim 90 wherein $R_1$ and $R_2$ are the same and $R_3$ and $R_4$ are the same.

93. The method of claim 92 wherein $R_3$ and $R_4$ are both a lower alkyl group or a substituted lower alkyl group.

94. The method of claim 93 wherein $R_3$ and $R_4$ are both methyl or ethyl.

95. The method of claim 94 wherein $R_1$ and $R_2$ are both an aryl or substituted aryl group.

96. The method of claim 94 wherein $R_1$ and $R_2$ are both a phenyl group or a substituted phenyl group.

97. The method of claim 94 wherein $R_1$ and $R_2$ are both a phenyl group substituted with one or more groups selected from —OH, —Br, —Cl, —I, —F, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^dH$—C(=NH)—$NH_2$, —$NR_d$—C(=NH)—$NHR^a$, $NR^dC$(=NH)—$N(R^aR^b)$, —$NR_d$C(=$NR^c$)—$NH_2$, —$NR^d$—C(=$NR^c$)—$NHR^a$, —$NR^d$—C(=$NR^c$)—$N(R^aR^b)$, —$NHNH_2$, $NHNHR^a$, —$NHR^aR^b$, —$SO_2NH_2$, —$SO_2NHR^a$, —$SO_2NR^aR^b$, —CH=$CHR^a$, —CH=$CHR^aR^b$, —$CR^c$=$CR^aR^b$, —$CR^c$=$CHR^a$, —$CR^c$=$CR^aR^b$ —$CCR^a$, —SH, —$SR^a$, —S(O)$R^a$, —S(O)$_2R^a$, alkyl group, substituted alkyl group, non-aromatic heterocyclic group, substituted non-aromatic heterocyclic group, benzyl group, substituted benzyl group, aryl group or substituted aryl group wherein $R^a$-$R^d$ are independently an alkyl group, substituted alkyl group, benzyl, substituted benzyl, aromatic or substituted aromatic group, or, [[—$NR^aR^d$]]—$N(R^aR^b)$, taken together, can also form a substituted or unsubstituted non-aromatic heterocyclic group.

98. The method of claim 94 wherein $R_3$ and $R_4$ are both a phenyl group or a substituted phenyl group.

99. The method of claim 98 wherein $R_1$ and $R_2$ are both a phenyl or substituted phenyl group.

100. The method of claim 92 wherein $R_1$ and $R_2$ are both a substituted phenyl group.

101. The method of claim 89 wherein the compound is represented by the following structural formula:

$$R_1-C(S)-N(R_3)-NH-C(O)-Y'-C(O)-NH-N(R_4)-C(S)-R_2;$$

wherein Y' is a covalent bond or —$CR_7R_8$—.

102. The method of claim 101 wherein $R_7$ and $R_8$ are different.

103. The method of claim 101 where $R_1$ and $R_2$ are the same; $R_3$ and $R_4$ are the same; and $R_7$ and $R_8$ are the same.

104. The method of claim 101 wherein $R_1$ and $R_2$ are both aryl or substituted aryl groups and $R_3$ and $R_4$ are both a lower alkyl group or a substituted lower alkyl group.

105. The method of claim 101 wherein $R_1$ and $R_2$ are both phenyl or substituted phenyl and $R_3$ and $R_4$ are methyl, ethyl, phenyl, or thienyl.

106. The method of claim 105 wherein $R_7$ and $R_8$ are both methyl or wherein $R_7$ and $R_8$, taken together, are propylene or butylene.

107. The method of claim 105 wherein $R_7$ is —H and $R_8$ is lower alkyl, thienyl, phenyl or benzyl.

108. The method of claim 105 wherein $R_1$ and $R_2$ are both phenyl substituted with one or more groups selected from —OH, —Br, —Cl, —I, —F, —$OR^a$, —O—$COR^a$, —$COR^a$, —CN, —$NO_2$, —COOH, —$SO_3H$, $H_2$, $NHR^a$, —$N(R^aR^b)$, —$COOR^a$, —CHO, —$CONH_2$, —$CONHR^a$, —CON($R^aR^b$), —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$CR^c$)—$NH_2$, —NH—C(=$NR^c$)—$NHR^a$, —NH—C(=$NR^c$)—$N(R^aR^b)$, —$NR^dH$—C(=NH)—$NH^2$, —$NR^d$—C(=NH)—$NHR^a$, —$NR^d$—C(=NH)—$N(R^aR^b)$, —$NR^d$—C(=$NR^c$)—$NH_2$, —$NR_d$—C(=$NR^c$)—$NHR^a$, —$NR^d$—C(=$NR^c$)—$N(R^aR^b)$, —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2R^a$, alkyl groups, substituted alkyl group, non-aromatic heterocyclic group, substituted non-aromatic heterocyclic group, benzyl group, substituted benzyl group, aryl group or substituted aryl group wherein $R^a$-$R^d$ are each independently an alkyl group, substituted alkyl group, benzyl, substituted benzyl, aromatic or substituted aromatic group, or, [[—$NR^aR^d$]]—$N(R^aR^b)$, taken together, can also form a substituted or unsubstituted non-aromatic heterocyclic group.

109. A method of treating a subject with cancer, said method comprising administering to the subject an effective amount of taxol or a taxol analog and an effective amount of a compound represented by the following structural formula:

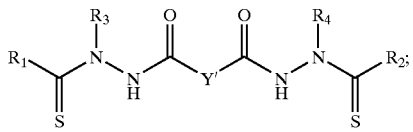

or a physiologically acceptable salt thereof, wherein:

Y' is a covalent bond or —$CR_7R_8$—;

$R_1$ and $R_2$ are both a substituted or unsubstituted aryl group;

$R_3$ and $R_4$ are both —H, methyl or ethyl; and $R_7$ is —H and $R_8$ is —H or methyl.

110. The method of claim 109 wherein $R_1$ and $R_2$ are both phenyl substituted with one or more groups selected from —OH, —Br, —Cl, —I, —F, —$OR^a$, —O—$COR^a$, —$COR^a$, —CN, —$NO_2$, —COOH, —$SO_3H$, $H_2$, $NHR^a$, —$N(R^aR^b)$, —$COOR^a$, —CHO, —$CONH_2$, —$CONHR^a$, —CON$(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$CR^c$)—$NH_2$, —NH—C(=$NR^c$)—$NHR^a$, —NH—C(=$NR^c$)—N$(R^aR^b)$, —$NR^dH$—C(=NH)—$NH^2$, —$NR^d$—C(=NH)—$NHR^a$, —$NR^d$—C(=NH)—$N(R^aR^b)$, —$NR^d$—C(=$NR^c$)—$NH_2$, —$NR_d$—C(=$NR^c$)—$NHR^a$, —$NR^d$—C(=$NR^c$)—$N(R^aR^b)$, —$NHNH_2$, —$NHNHR^a$, —$NHR^aR^b$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2R^a$, alkyl groups, substituted alkyl group, non-aromatic heterocyclic group, substituted non-aromatic heterocyclic group, benzyl group, substituted benzyl group, aryl group or substituted aryl group wherein $R^a$–$R^d$ are each independently an alkyl group, substituted alkyl group, benzyl, substituted benzyl, aromatic or substituted aromatic group, or, [[—$NR^aR^d$]]—$N(R^aR^b)$, taken together, can also form a substituted or unsubstituted non-aromatic heterocyclic group.

111. The method of claim 89 wherein $R_5$ and $R_6$ are the same.

112. The method of claim 111 wherein the compound is represented by the following structural formula:

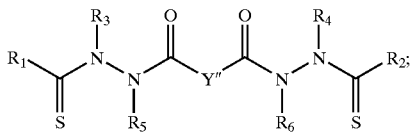

wherein Y" is a covalent bond or —$CH_2$—.

113. The method of claim 111 wherein $R_5$ and $R_6$ are both a lower alkyl group or a phenyl group.

114. The method of claim 113 wherein $R_5$ and $R_6$ are both a methyl group.

115. The method of claim 112 wherein $R_1$ and $R_2$ are both phenyl or substituted phenyl; $R_3$ and $R_4$ are both a lower alkyl group; and $R_5$ and $R_6$ are both a lower alkyl group.

116. A method of treating a subject with cancer, said method comprising administering to the subject an effective amount of taxol or a taxol analog and an effective amount of a compound represented by the following structural formula:

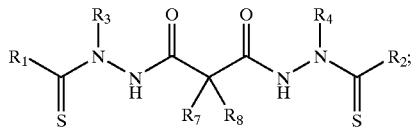

or physiologically acceptable salt thereof, wherein:

a) $R_1$ and $R_2$ are both phenyl; $R_3$ and $R_4$ are both phenyl; $R_7$ and $R_8$ are both —H;

b) $R_1$ and $R_2$ are both phenyl; $R_3$ and $R_4$ are both methyl; $R_7$ and $R_8$ are both —H;

c) $R_1$ and $R_2$ are both phenyl; $R_3$ and $R_4$ are both ethyl; $R_7$ and $R_8$ are both —H;

d) $R_1$ and $R_2$ are both 4-cyanophenyl; $R_3$ and $R_4$ are both methyl; $R_7$ is methyl; $R_8$ is —H;

e) $R_1$ and $R_2$ are both 4-methoxyphenyl; $R_3$ and $R_4$ are both methyl; $R_7$ and $R_8$ are both —H;

f) $R_1$ and $R_2$ are both phenyl; $R_3$ and $R_4$ are both methyl; $R_7$ is methyl; $R^8$ is —H;

g) $R_1$ and $R_2$ are both phenyl; $R_3$ and $R_4$ are both ethyl; $R_7$ is methyl; $R_8$ is —H;

h) $R_1$ and $R_2$ are both 4-cyanophenyl; $R_3$ and $R_4$ are both methyl; $R_7$ and $R_8$ are both —H;

i) $R_1$ and $R_2$ are both 2,5-dimethoxyphenyl; $R_3$ and $R_4$ are both methyl; $R_7$ and $R_8$ are both —H;

j) $R_1$ and $R_2$ are both 2,5-dimethoxyphenyl; $R_3$ and $R_4$ are both methyl; $R_7$ is methyl; $R_8$ is —H;

k) $R_1$ and $R_2$ are both 3-cyanophenyl; $R_3$ and $R_4$ are both methyl; $R_7$ and $R_8$ are both —H;

l) $R_1$ and $R_2$ are both 3-fluorophenyl; $R_3$ and $R_4$ are both methyl; $R_7$ and $R_8$ are both —H;

m) $R_1$ and $R_2$ are both 4-chlorophenyl; $R_3$ and $R_4$ are both methyl; $R_7$ is methyl; $R_8$ is —H;

n) $R_1$ and $R_2$ are both 2-dimethoxyphenyl; $R_3$ and $R_4$ are both methyl; $R_7$ and $R_8$ are both —H;

o) $R_1$ and $R_2$ are both 3-methoxyphenyl; $R_3$ and $R_4$ are both methyl; $R_7$ and $R_8$ are both —H;

p) $R_1$ and $R_2$ are both 2,3-dimethoxyphenyl; $R_3$ and $R_4$ are both methyl; $R_7$ and $R_8$ are both —H;

q) $R_1$ and $R_2$ are both 2,3-dimethoxyphenyl; $R_3$ and $R_4$ are both methyl; $R_7$ is methyl; $R_8$ is —H;

r) $R_1$ and $R_2$ are both 2,5-difluorophenyl; $R_3$ and $R_4$ are both methyl; $R_7$ and $R_8$ are both —H;

s) $R_1$ and $R_2$ are both 2,5-difluorophenyl; $R_3$ and $R_4$ are both methyl; $R_7$ is methyl; $R_8$ is —H;

t) $R_1$ and $R_2$ are both 2,5-dichlorophenyl; $R_3$ and $R_4$ are both methyl; $R_7$ and $R_8$ are both —H;

u) $R_1$ and $R_2$ are both 2,5-dimethylphenyl; $R_3$ and $R_4$ are both methyl; $R_7$ and $R_8$ are both —H;

v) $R_1$ and $R_2$ are both 2,5-dimethoxyphenyl; $R_3$ and $R_4$ are both methyl; $R_7$ and $R_8$ are both —H;

w) $R_1$ and $R_2$ are both phenyl; $R_3$ and $R_4$ are both methyl; $R_7$ and $R_8$ are both —H; or x) $R_1$ and $R_2$ are both 2,5-dimethoxyphenyl; $R_3$ and $R_4$ are both methyl; $R_7$ is methyl; $R_8$ is —H.

117. A method of treating a subject with cancer, said method comprising administering to the subject an effective amount of taxol or a taxol analog and an effective amount of a compound represented by the following structural formula:

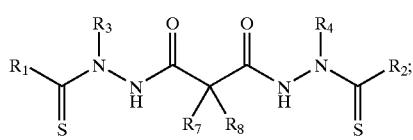

or a physiologically acceptable salt thereof, wherein:

a) $R_1$ and $R_2$ are both 4-cyanophenyl; $R_3$ and $R_4$ are both methyl; $R_7$ is methyl; $R_8$ is —H;

b) $R_1$ and $R_2$ are both 2,5-dimethoxyphenyl; $R_3$ and $R_4$ are both methyl; $R_7$ and $R_8$ are both —H;

c) $R_1$ and $R_2$ are both 2,5-dimethoxyphenyl; $R_3$ and $R_4$ are both methyl; $R_7$ is methyl; $R_8$ is —H;

d) $R_1$ and $R_2$ are both 3-fluorophenyl; $R_3$ and $R_4$ are both methyl; $R_7$ and $R_8$ are both —H;

e) $R_1$ and $R_2$ are both 2,3-dimethoxyphenyl; $R_3$ and $R_4$ are both methyl; $R_7$ and $R_8$ are both —H;

f) $R_1$ and $R_2$ are both phenyl; $R_3$ and $R_4$ are both methyl; $R_7$ and $R_8$ are both —H; and $R_1$ and $R_2$ are both phenyl; $R_3$ and $R_4$ are both phenyl; $R_7$ and $R_8$ are both —H.

* * * * *

UNITED STATES PATENT AND TRADEMARK OFFICE
CERTIFICATE OF CORRECTION

PATENT NO.        : 6,800,660 B2
APPLICATION NO. : 10/193075
DATED             : October 5, 2004
INVENTOR(S)      : Keizo Koya et al.

It is certified that error appears in the above-identified patent and that said Letters Patent is hereby corrected as shown below:

Column 38

Claim 14, line 27, delete "group substituted with substituted with" and insert --group substituted with--;

Claim 14, line 32, delete " -NRCOR$^a$," and insert -- -NR$^c$COR$^a$,--;

Claim 14, lines 40-41, delete " -NR$^d$H-C(=NR$^c$)-NH$_2$, -NR$^d$-C(=NH_-NHR$^a$," and insert -- -NR$^d$-C(=NH)-NH$_2$, -NR$^d$-C(=NH)-NHR$^a$,--;

Claim 14, lines 42-43, delete " -NR$^d$-C(=NR$^c$)-N(R$^a$R$^b$) -NHNH$_2$," and insert -- -NR$^d$-C(=NR$^c$)-N(R$^a$R$^b$), -NHNH$_2$,--;

Claim 14, line 46, delete "-CR$^c$=CR$^a$R$^b$, -CCR$^a$," and insert -- -CCR$^a$,--;

Claim 14, line 50, delete "R$^a$-R$^b$" and insert --R$^a$-R$^d$--;

Claim 14, line 52, delete "[[-NR$^a$R$^d$]]".

Column 39

Claim 22, line 13, delete " -NRCOR$^a$," and insert -- -NR$^c$COR$^a$,--;

Claim 22, line 21, delete " -NR$^d$H-C(=NH)-NH$_2$," and insert -- -NR$^d$-C(=NH)-NH$_2$,--;

Claim 22, line 22 delete " -NR$^d$-C(=NH)-N(R$^a$R$^b$)-NR$^a$-C(=NR$^c$)-NH$_2$," and insert -- -NR$^d$-C(=NH)-N(R$^a$R$^b$), -NR$^d$-C(=NR$^c$)-NH$_2$,--;

Claim 22, line 23, delete "-NR$^d$-C(=NR$^c$)-NHR$_a$," and insert -- -NR$^d$-C(=NR$^c$)-NHR$^a$,--;

Claim 22, line 24, delete " -NHNHR$^a$" and insert -- -NHNHR$^a$,--;

Claim 22, line 27, delete "-CR$^c$=CR$^a$R$^b$, -CCR$^a$," and insert -- -CCR$^a$,--;

Claim 22, line 34, delete "[[-NR$^a$R$^d$]]";

Claim 26, line 50, delete "-NRCOR$^a$," and insert -- NR$^c$COR$^a$,--;

UNITED STATES PATENT AND TRADEMARK OFFICE
CERTIFICATE OF CORRECTION

PATENT NO. : 6,800,660 B2
APPLICATION NO. : 10/193075
DATED : October 5, 2004
INVENTOR(S) : Keizo Koya et al.

It is certified that error appears in the above-identified patent and that said Letters Patent is hereby corrected as shown below:

Column 39 (cont'd)

Claim 26, line 58, delete " -$NR^dH$-C(=NH)-$NH_2$," and insert -- -$NR^d$-C(=NH)-$NH_2$,--;

Claim 26, line 59, delete " -$NR^d$-C(=NH)-N($R^aR^b$)-$NR^a$-C(=$NR^c$)-$NH_2$," and insert -- -$NR^d$-C(=NH)-N($R^aR^b$), -$NR^d$-C(=$NR^c$)-$NH_2$,--;

Claim 26, line 60, delete "-$NR^d$-C(=$NR^c$)-$NHR_a$," and insert -- -$NR^d$-C(=$NR^c$)-$NHR^a$,--;

Claim 26, line 61, delete " -$NHNHR^a$" and insert -- -$NHNHR^a$,--;

Claim 26, line 64, delete "-$CR^c$=$CR^aR^b$, -$CCR^a$," and insert -- -$CCR^a$,--.

Column 40

Claim 26, line 4, delete "[[-$NR^aR^d$]]";

Claim 34, line 42, delete " -$NRCOR^a$," and insert -- -$NR^cCOR^a$,--;

Claim 34, line 51, delete " -$NR^dH$-C(=NH)-$NH_2$," and insert -- -$NR^d$-C(=NH)-$NH_2$,--;

Claim 34, lines 52-53, delete " -$NR^d$-C(=NH)-N($R^aR^b$)-$NR^a$-C(=$NR^c$)-$NH_2$," and insert -- -$NR^d$-C(=NH)-N($R^aR^b$), -$NR^d$-C(=$NR^c$)-$NH_2$,--;

Claim 34, line 53, delete "-$NR^d$-C(=$NR^c$)-$NHR_a$," and insert -- -$NR^d$-C(=$NR^c$)-$NHR^a$,--;

Claim 34, line 54, delete "-$NHNHR^a$-$NHR^aR^b$," and insert -- -$NHNHR^a$, -$NHR^aR^b$,--;

Claim 34, line 57, delete "-$CR^c$=$CR^aR^b$, -$CCR^a$," and insert -- -$CCR^a$,--;

Claim 34, line 65, delete "[[-$NR^aR^d$]]".

UNITED STATES PATENT AND TRADEMARK OFFICE
CERTIFICATE OF CORRECTION

PATENT NO. : 6,800,660 B2
APPLICATION NO. : 10/193075
DATED : October 5, 2004
INVENTOR(S) : Keizo Koya et al.

It is certified that error appears in the above-identified patent and that said Letters Patent is hereby corrected as shown below:

Column 41

Claim 36, line 23, delete " -NRCOR$^a$," and insert -- -NR$^c$COR$^a$,--;

Claim 36, line 31, delete " -NR$^d$H-C(=NH)-NH$_2$," and insert -- -NR$^d$-C(=NH)-NH$_2$,--;

Claim 36, lines 32-33, delete " -NR$^d$-C(=NH)-N(R$^a$R$^b$)-NR$^a$-C(=NR$^c$)-NH$_2$," and insert -- -NR$^d$-C(=NH)-N(R$^a$R$^b$), -NR$^d$-C(=NR$^c$)-NH$_2$,--;

Claim 36, line 33, delete "-NR$^d$-C(=NR$^c$)-NHR$_a$," and insert -- -NR$^d$-C(=NR$^c$)-NHR$^a$,--;

Claim 36, line 34, delete " -NHNHR$^a$-NHR$^a$R$^b$," and insert -- -NHNHR$^a$, -NHR$^a$R$^b$,--;

Claim 36, line 37, delete "-CR$^c$=CR$^a$R$^b$, -CCR$^a$," and insert -- -CCR$^a$,--;

Claim 36, line 44, delete " [[-NR$^a$R$^d$]]-(R$^a$R$^b$)," and insert -- -N(R$^a$R$^b$),--.

Column 42

Claim 42, line 59, delete "both 2,5-dimethyLphenyl;" and insert --both 2,5-dimethylphenyl;--.

Column 43

Claim 44, line 51, delete "R$_5$-R$_6$ are" and insert --R$_5$ and R$_6$ are--.

Column 44

Claim 57, lines 58-59, delete " COR$^a$ -CN, -NO$_2$, -COON, -SO$_3$H, -NHR$^a$," and insert -- COR$^a$, -CN, -NO$_2$, -COOH, -SO$_3$H, -NH$_2$, -NHR$^a$,--;

Claim 57, line 60, delete " -NHCOR$^a$-," and insert -- -NHCOR$^a$,--;

Claim 57, line 61, delete " -NRCOR$^a$," and insert -- -NR$^c$COR$^a$,--;

Claim 57, line 63, delete " -C(=NH)-NHR$_2$," and insert -- -C(=NH)-NHR$^a$,--.

UNITED STATES PATENT AND TRADEMARK OFFICE
CERTIFICATE OF CORRECTION

PATENT NO.       : 6,800,660 B2
APPLICATION NO. : 10/193075
DATED            : October 5, 2004
INVENTOR(S)      : Keizo Koya et al.

It is certified that error appears in the above-identified patent and that said Letters Patent is hereby corrected as shown below:

Column 45

Claim 57, lines 1-2, delete " -NH-C(=NR$^c$)-N-NR$^d$H-C(=NH)-NH$_2$," and insert
-- -NH-C(=NR$^c$)-N(R$^a$R$^b$), -NR$^d$-C(=NH)-NH$_2$,--;

Claim 57, lines 2-3, delete " -NR$_d$-C(=NH)-(R$^a$R$^b$)" and insert
-- -NR$^d$-C(=NH)-N(R$^a$R$^b$),--;

Claim 57, line 4, delete "-NR$^d$-C=NR$^c$)-N(R$^a$R$^b$)-NHNH$_2$," and insert
-- -NR$^d$-C=NR$^c$)-N(R$^a$R$^b$), -NHNH$_2$,--;

Claim 57, line 5, delete " -NHR$^a$R$^b$ -," and insert -- -NHR$^a$R$^b$,--;

Claim 57, line 7, delete " -CR$^c$=CR$^a$R$^b$, -CR$^c$=CHR$^a$, -CR$^c$=CR$^a$R$^b$," and insert
-- -CR$^c$=CR$^a$R$^b$, -CR$^c$=CHR$^a$,--;

Claim 57, line 13, delete "[[-NR$^a$R$^d$]]";

Claim 68, line 58, delete " -NRCOR$^a$," and insert -- -NR$^c$COR$^a$,--;

Claim 68, line 66, delete " -NR$^d$H-C(=NH)-NH$_2$," and insert -- -NR$^d$-C(=NH)-NH$_2$,--.

Column 46

Claim 68, lines 1-2, delete " -NR$^c$-C(=NR$^c$)-N(R$^a$R$^b$)," and insert
-- -NR$^d$-C(=NR$^c$)-N(R$^a$R$^b$),--;

Claim 68, line 2, delete " -SO$_{NH2}$," and insert -- -SO$_2$NH$_2$,--;

Claim 68, line 5, delete "-CR$^c$=CR$^a$R$^b$, -CCR$^a$," and insert -- -CCR$^a$,--;

Claim 68, line 12, delete "[[-NR$^a$R$^d$]]";

Claim 70, line 39, delete " -NRCOR$^a$," and insert -- -NR$^c$COR$^a$,--;

Claim 70, line 47, delete " -NR$^d$H-C(=NH)-NH$_2$," and insert -- -NR$^d$-C(=NH)-NH$_2$,--;

UNITED STATES PATENT AND TRADEMARK OFFICE
CERTIFICATE OF CORRECTION

PATENT NO. : 6,800,660 B2
APPLICATION NO. : 10/193075
DATED : October 5, 2004
INVENTOR(S) : Keizo Koya et al.

It is certified that error appears in the above-identified patent and that said Letters Patent is hereby corrected as shown below:

Column 46 (cont'd)

Claim 70, line 50, delete " -$SO_{NH2}$," and insert -- -$SO_2NH_2$,--;

Claim 70, line 53, delete "-$CR^c=CR^aR^b$, -$CCR^a$," and insert -- -$CCR^a$,--;

Claim 70, line 60, delete "[[-$NR^aR^d$]]".

Column 47

Claim 76, line 40, delete "t) $R_1$" and insert --f) $R_1$--;

Claim 76, line 53, delete "$R_1$ and $R_2$ $^{are\,both}$ 3-fluorophenyl; $R_3$ and $R_3$ are both" and insert --$R_1$ and $R_2$ are both 3-fluorophenyl; $R_3$ and $R_4$ are both--.

Column 48

Claim 78, line 62, delete "$R_5$-$R_6$ are" and insert --$R_5$ and $R_6$ are--.

Column 49

Claim 82, line 19, delete "hydrcarbyl" and insert --hydrocarbyl--.

Column 50

Claim 84, line 14, delete "$R_{15}$-H," and insert --$R_{15}$ is -H,--;

Claim 84, line 22, delete "substituted, lower alkyl," and insert --substituted lower alkyl,--;

Claim 84, line 24, delete "$R_{18}$-H," and insert --$R_{18}$ is -H,--;

Claim 84, line 26, delete "six membered a non-aromatic" and insert --six membered non-aromatic--;

Claim 85, line 34, delete "tert-butoxy" and insert --*tert*-butoxy--;

UNITED STATES PATENT AND TRADEMARK OFFICE
CERTIFICATE OF CORRECTION

PATENT NO.       : 6,800,660 B2
APPLICATION NO.  : 10/193075
DATED            : October 5, 2004
INVENTOR(S)      : Keizo Koya et al.

It is certified that error appears in the above-identified patent and that said Letters Patent is hereby corrected as shown below:

Column 50 (cont'd)

Claim 85, lines 36-37, delete "orpara-chlorophenyl;" and insert --or *para*-chlorophenyl;--;

Claim 85, line 39, delete "orpara-toluyl;" and insert --or *para*-toluyl;--;

Claim 85, lines 43-44, delete "are $R_{14}$ is -H," and insert --are -$CH_2$-; $R_{14}$ is -H,--;

Claim 85, line 46, delete "$R_{16}$ ¡s phenyl;" and insert --$R_{16}$ is phenyl;--;

Claim 85, line 47, delete "$R_{17}$-H," and insert --$R_{17}$ is -H,--.

Column 51

Claim 97, line 40, delete " -$NRCOR^a$," and insert -- -$NR^cCOR^a$,--;

Claim 97, lines 48-49, delete " -$NR^dH$-C(=NH)-$NH_2$, $NR_d$-C(=NH)-$NHR^a$," and insert -- -$NR^d$-C(=NH)-$NH_2$, -$NR^d$-C(=NH)-$NHR^a$,--;

Claim 97, lines 49-50, delete " -$NR_d$-C(=$NR^c$)-$NH_2$," and insert -- -$NR^d$-C(=$NR^c$)-$NH_2$,--;

Claim 97, lines 50-51, delete " -$NR^d$-(=$NR^c$)-N($R^aR^b$), -$NHNH_2$, $NHNHR^a$," and insert -- -$NR^d$-C(=$NR^c$)-N($R^aR^b$), -$NHNH_2$, -$NHNHR^a$,--;

Claim 97, line 53, delete " -CH=$CHR^aR^b$," and insert -- -CH=$CR^aR^b$,--;

Claim 97, line 54, delete "-$CR^c$=$CR^aR^b$ -$CCR^a$," and insert -- -$CCR^a$,--;

Claim 97, line 61, delete "[[-$NR^aR^d$]]".

Column 52

Claim 108, line 35, delete " -$SO_3H$, $H_2$, $NHR^a$," and insert -- -$SO_3H$, -$NH_2$, -$NHR^a$,--;

Claim 108, line 37, delete " -$NRCOR^a$," and insert -- -$NR^cCOR^a$,--;

UNITED STATES PATENT AND TRADEMARK OFFICE
CERTIFICATE OF CORRECTION

PATENT NO. : 6,800,660 B2
APPLICATION NO. : 10/193075
DATED : October 5, 2004
INVENTOR(S) : Keizo Koya et al.

It is certified that error appears in the above-identified patent and that said Letters Patent is hereby corrected as shown below:

Column 52 (cont'd)

Claim 108, lines 44-45, delete " -NH-C(=CR$^c$)-NH$_2$," and insert
-- -NH-C(=NR$^c$)-NH$_2$,--;

Claim 108, line 46, delete "-NR$^d$H-C(=NH)-NH$_2$," and insert -- -NR$^d$-C(=NH)-NH$_2$,--;

Claim 108, line 48, delete " -NR$_d$-C(=NR$^c$)-NHR$^a$," and insert
-- -NR$^d$-C(=NR$^c$)-NHR$^a$,--;

Claim 108, line 53, delete "-CR$^c$=CR$^a$R$^b$, -CCR$^a$," and insert -- -CCR$^a$,--;

Claim 108, line 60, delete "[[-NR$^a$R$^d$]]".

Column 53

Claim 110, line 18, delete " -SO$_3$H, H$_2$, NHR$^a$," and insert -- -SO$_3$H, -NH$_2$, -NHR$^a$,--;

Claim 110, line 20, delete " -NRCOR$^a$," and insert -- -NR$^c$COR$^a$,--;

Claim 110, lines 26-27, delete " -NH-C(=CR$^c$)-NH$_2$," and insert
-- -NH-C(=NR$^c$)-NH$_2$,--;

Claim 110, line 28, delete "-NR$^d$H-C(=NH)-NH$_2$," and insert
-- -NR$^d$-C(=NH)-NH$_2$,--;

Claim 110, line 30, delete " -NR$_d$-C(=NR$^c$)-NHR$^a$," and insert
-- -NR$^d$-C(=NR$^c$)-NHR$^a$,--;

Claim 110, line 34, delete "-CR$^c$=CR$^a$R$^b$, -CCR$^a$," and insert -- -CCR$^a$,--;

Claim 110, line 41, delete "[[-NR$^a$R$^d$]]".

UNITED STATES PATENT AND TRADEMARK OFFICE
CERTIFICATE OF CORRECTION

| | |
|---|---|
| PATENT NO. | : 6,800,660 B2 |
| APPLICATION NO. | : 10/193075 |
| DATED | : October 5, 2004 |
| INVENTOR(S) | : Keizo Koya et al. |

It is certified that error appears in the above-identified patent and that said Letters Patent is hereby corrected as shown below:

<u>Column 56</u>

Claim 117, line 9, delete "both -H; and" and insert --both -H; or--;

Claim 117, line 10, delete "$R_1$ and $R_2$ are" and insert --g) $R_1$ and $R_2$ are--.

Signed and Sealed this

Fourth Day of December, 2007

JON W. DUDAS
*Director of the United States Patent and Trademark Office*